US007425611B2

(12) United States Patent
Lal et al.

(10) Patent No.: US 7,425,611 B2
(45) Date of Patent: Sep. 16, 2008

(54) IMMUNOGENIC HIV-1 MULTI-CLADE, MULTIVALENT CONSTRUCTS AND METHODS OF THEIR USE

(75) Inventors: Renu B. Lal, Dulles, VA (US); Sherry M. Owen, Douglasville, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 10/550,651

(22) PCT Filed: Mar. 26, 2004

(86) PCT No.: PCT/US2004/009767

§ 371 (c)(1),
(2), (4) Date: Sep. 26, 2005

(87) PCT Pub. No.: WO2004/085466

PCT Pub. Date: Oct. 7, 2004

(65) Prior Publication Data

US 2006/0216305 A1 Sep. 28, 2006

Related U.S. Application Data

(60) Provisional application No. 60/458,880, filed on Mar. 28, 2003.

(51) Int. Cl.
*C07K 5/00* (2006.01)
*A61K 39/00* (2006.01)
*C07H 21/04* (2006.01)

(52) U.S. Cl. .................. 530/350; 424/184.1; 536/23.1

(58) Field of Classification Search ........................ None
See application file for complete search history.

(56) References Cited

U.S. PATENT DOCUMENTS

| | | | |
|---|---|---|---|
| 5,633,234 | A | 5/1997 | August et al. |
| 6,319,503 | B1 | 11/2001 | Kenten et al. |
| 6,534,482 | B1 | 3/2003 | Fikes et al. |
| 2002/0119127 | A1 | 8/2002 | Sette et al. |
| 2002/0182222 | A1 | 12/2002 | Groot |
| 2003/0003440 | A1* | 1/2003 | Lopalco ............... 435/5 |
| 2003/0108562 | A1 | 6/2003 | Hanke et al. |

FOREIGN PATENT DOCUMENTS

| | | |
|---|---|---|
| EP | 1 130 289 A | 9/2001 |
| WO | WO 99/58658 | 11/1999 |
| WO | WO 00/29008 | 5/2000 |
| WO | WO 01/12216 | 2/2001 |
| WO | WO 01/19408 | 3/2001 |
| WO | WO 01/24810 | 4/2001 |
| WO | WO 01/47955 * | 7/2001 |
| WO | WO 02/36806 | 5/2002 |
| WO | WO 02/080851 | 10/2002 |
| WO | WO 03/029285 | 4/2003 |
| WO | WO 03/097675 | 11/2003 |

OTHER PUBLICATIONS

Duarte et al., Multiepitope polypeptide of the HIV-1 envelope induces neutralizing monoclonal antibodies against V3 loop, 1994, AIDS Research and Human Retroviruses, 10(3): 235-243.*
Carbone et al., The Use of Hydrophobic, a Helix-Defined Peptides in Delineating the T cell Determinant for Pigeon Cytochrome c, Journal of Immunology, 1987, 138(6):1838-1844.*
Suhrbier et al., Polytope vaccines for the codelivery of multiple CD8 T-cell epitopes, Expert Rev. Vaccines, 2002, 1(2):207-213.*
Velders et al., Defined Flanking Spacers and Enhanced Proteolysis Is Essential for Eradication of Established Tumors by an Epitope String DNA Vaccine, The Journal of Immunology, 2001, 166: 5366-5373.*
Amara et al., "Control of a Mucosal Challenge and Prevention of AIDS by a Multiprotein DNA/MVA Vaccine," *Science* 292:69-74 (Apr. 6, 2001).
Bonini et al., "Targeting Antigen in Mature Dendritic Cells for Simultaneous Stimulation of $CD4^+$ and $CD8^+$ T Cells," *J. Immunology* 166:5250-5257 (2001).
Boyer et al., "HIV-1 DNA based vaccine induces a CD8 meidated cross-clade CTL response," *Dev Biol Stand* 95:147-153 (1998) Abstract Only.
Fredericksen et al., "Inhibition of endosomal/lysosomal degradation increases the infectivity of human immunodeficiency virus," *J Virology* 72(22):11440-11446 (Nov. 2002) Abstract Only.
Fujita et al., "In vitro binding study of adaptor protein complex (AP-1) to lysosomal targeting motif (LI-motif)," *Biochem Biophys Res Commun* 255(1):54-58 (Feb. 1999) Abstract Only.
Hanke and McMichael, "Design and construction of an experimental HIV-1 vaccine for a year-2000 clinical trial in Kenya," *Nature Medicine* 6(9):951-955 (Sep. 2000).

(Continued)

*Primary Examiner*—Bruce Campell
*Assistant Examiner*—Nicole Kinsey White
(74) *Attorney, Agent, or Firm*—Klarquist Sparkman LLP

(57) ABSTRACT

Described herein are nucleic acid molecules which encode multiple highly conserved epitopes from HIV-1 proteins, and optionally also epitopes from CCR5; usually also included sequences that encode spacers between two or more of the epitopes. Some of the provided nucleic acid molecules further include sequences that encode targeting domains, useful for targeting the encoded protein into a pathway for enhancing epitope presentation in a vertebrate immune system. Also described are multivalent proteins encoded for by these nucleic acid molecules. The disclosure also encompasses immunogenic compositions that comprise one or more of the nucleic acid molecules, and/or one or more of the proteins encoded thereby, as well as methods of inducing an immune response against HIV-1 in a subject by administering to the subject an effective amount of a composition containing one or more of these molecules. Also provided are cultured host cells containing within them one or more of the described nucleic acid molecules.

10 Claims, 7 Drawing Sheets

OTHER PUBLICATIONS

Keating et al. "Cross-clade T lymphocyte-mediated immunity to HIV type 1: implications for vaccine design and immunodetection assays," *AIDS Res Hum Retroviruses* 18(14):1067-1079 (Sep. 20, 2000) Abstract Only.

Kong Wing-Pui et al, "Immunogenicity of Multiple gene and clade human immunodeficiency virus type 1 DNA vaccines," *J Virology* 77(23):12764-12772 (Dec. 2003).

Lacaille et al., "Targeting of HIV-1 Nef to the Centrosome: Implications for Antigen Processing," *Traffic* 1:884-891 (2000).

Lacasse et al., "Fusion-competent vaccines: Broad neutralization of primary isolates of HIV," *Science* 283(5400):357-362 (Jan. 15, 1999).

Livingston et al., "Optimization of epitope processing enhances immunogenicity of multiepitope DNA vaccines," *Vaccine* 19:4652-4660 (2001).

Lohnas et al., "Epitope-Specific Antibody and Suppression of Autoantibody Responses Against a Hybrid Self Protein," *J. Immunology* 161:6518-6525 (1998).

Lu, "HIV-1 Gag DNA Vaccine Chimera with Expression and Adjuvant Properties of the Lysosomal-Associated Membrane Protein (LAMP) and Dendritic Cell Multi-Lectin Receptor (DC-MLR) in an AAV-ITR Plasmid Vector," *Aids Vaccine Conference Abstract* URL: http://63.84.172.40/Posters/312.1.pdf> (Sep. 7, 2001).

Owen et al., "Susceptibility of diverse primary HIV isolates with varying co-receptor specificity's to CXCR4 antagonistic compounds," *J. Medical Virology* 68(2):147-155 (Oct. 2002).

Ruff et al., "The Enhanced Immune Response to the HIV gp160/LAMP Chimeric Gene Product Targeted to the Lysosome Membrane Protein Trafficking Pathway," *J. Biological Chemistry* 272(13):8671-8678 (1997).

Singh et al., "Generation of genome-wide CD8 T cell responses in HLA-A*0201 transgenic mice by an HIV-1 ubiquitin expression library immunization vaccine," *J Immunology* 168(1)379-391 (Jan. 1, 2002).

Suhrbier, "Multi-epitope DNA vaccines," *Immunol Cell Biol* 75(4):402-408 (1997) Abstract Only.

Sykes and Johnston, "Genetic live vaccines mimic the antigenicity but not pathogenicity of live viruses," *DNA Cell Biol* 18(7):521-531 (Jul. 1999).

Thomson et al., "Delivery of Multiple CD8 Cytotoxic T Cell Epitopes by DNA Vaccination," *J. Immunology* 160:1717-1723 (1998).

Thomson et al., "Targeting a Polyepitope Protein Incorporating Multiple Class II-Restricted Viral Epitopes to the Secretory/Endocytic Pathway Facilitates Immune Recognition by $CD4^+$ Cytotoxic T Lymphocytes: a Novel Approach to Vaccine Design," *J. Virology* 72(3):2246-2252 (Mar. 1998).

Tobery et al., "Targeting of HIV-1 Antigens for Rapid Intracellular Degradation Enhances Cytotoxic T Lymphocyte (CTL) Recognition and the Induction of De Novo CTL Responses In Vivo After Immunization," *J Exp Med* 185(5):909-920 (Mar. 3, 1997).

Tourdot et al., "Design of a polyepitope construct for the induction of HLA-A0201-restricted HIV 1-specific CTL responses using HLA-A*0201 transgenic, H-2 class 1 KO mice," *Eur J Immunol* 31(10):3064-3074 (Oct. 2001) Abstract Only.

Rowell et al., "Lysosome-Associated Membrane Protein-1-Mediated Targeting of the HIV-1 Envelope Protein to an Endosomal/Lysosomal Compartment Enhances its Presentation to MHC Class II-Restricted T Cells," *J Immunology* 155:1818-1828 (1995).

Woodberry et al., "Immunogenicity of a Human Immunodeficiency Virus (HIV) Polytope Vaccine Containing Multiple HLA A2 HIV $CD8^+$Cytotoxic T-Cell Epitopes," *J Virology* 73(7):5320-5325 (Jul. 1999).

* cited by examiner

IMMUNOGENIC HIV-1 MULTI-CLADE, MULTIVALENT CONSTRUCTS AND METHODS OF THEIR USE

PRIORITY CLAIM

This is the U.S. National Stage of International Application No. PCT/US2004/009767, filed Mar. 26, 2004, which was published in English under PCT Article 21(2), which in turn claims the benefit of U.S. Provisional application No. 60/458,990 filed Mar. 28, 2003. Both applications are incorporated herein in their entirety.

STATEMENT OF GOVERNMENT SUPPORT

This invention was made by the Centers for Disease Control and Prevention, an agency of the United States Government. Therefore, the U.S. Government has certain rights in this invention.

FIELD

This disclosure relates to compositions for induction of immune responses in vertebrates. More particularly, it relates to highly effective, broad spectrum multivalent constructs, both protein and nucleic acid, for inducing an immune response to an immunodeficiency virus, such as HIV-1. The disclosure further relates to vaccines comprising immunogenic compounds.

BACKGROUND

Vertebrates have developed a sophisticated system to protect themselves against a wide variety of hazards including various viruses and microorganisms, such as bacteria and fungi, as well as genetic diseases, neoplasia, and effects of a variety of toxins. The system has evolved based on the ability to recognize self as distinct from non-self or "foreign." A broad panoply of defense mechanisms are involved, including phagocytosis, lysis, such as complement mediated or perform mediated lysis, and killer cells, such as cytotoxic T-lymphocytes (CTLs; also known as cytotoxic/suppressor T-cells, Tc/s), natural killer cells, antibody dependent cytotoxic cells, and the like. Various cell types offer different mechanisms whereby the invader or endogenous diseased cell may be eliminated.

A key to the immune defensive mechanism is the T-cell. For instance, it is well known that the adaptive immune system shows a much stronger response on second, as compared to first, encounter with an antigen. This phenomenon is exploited in vaccination, which works by inducing a state of lasting immunity known as immunological memory. Immunological memory requires activation of T-lymphocytes specific for the vaccine antigen.

T-cells have been found to be "restricted" in that they respond to an antigen in relation to one or a few specific molecules (now called major histocompatibility or MHC molecules) associated with their natural host. In vitro, T-cells from a host of one haplotype respond to an antigen in relation to an MHC molecule of a different haplotype host. The T-cell receptor recognition repertoire appears to be narrower than the recognition repertoire of immunoglobulins produced by B-cells. In addition, rather than directly binding to an antigen as do antibodies and other immunoglobulins, the T-cell receptor appears to require concomitant binding to a foreign antigen and an MHC molecule.

MHC molecules are divided into two classes, Class I and Class II. The former class is relatively ubiquitous on vertebrate cells, while the latter is generally limited to lymphocytes, macrophages, and dendritic cells. Functionally different T-cells appear to be activated in relation to one or the other class of MHC molecules. The nature of the activity of a T-cell varies with the Class of the MHC molecule to which it is complementary. A T-cell clone recognizes a specific antigen in conjunction with a specific MHC allele. Furthermore, variation in the antigen structure affects the nature of the response when the T-cell, antigen, and antigen presenting cell are brought together. Depending upon the nature of the structural change, three possibilities are encountered: no change, increased stimulation or decreased stimulation of an immune response to the antigen.

T-lymphocytes detect foreign polypeptide antigens by recognizing—via the T-cell receptor ("TCR")—peptide fragments derived from the antigen. Most T-lymphocytes, however, are MHC restricted, that is, they recognize only complexes of peptides bound to the highly polymorphic membrane proteins encoded by Class I and Class II MHC genes and presented (displayed) on the surface of an accessory cell (designated an antigen-presenting cell or "APC"), in which the antigen has been processed.

Antigens can be processed by one of two pathways, depending on their origin, inside or outside the APC. In a first pathway, foreign material from outside a cell is engulfed by a specialized APC (often a macrophage or B-cell), which breaks down the material and complexes the processed antigen with Class II MHC molecules. In particular, MHC Class II molecules are synthesized in the endoplasmic reticulum with their antigenic peptide binding sites blocked by the invariant chain protein (Ii). These MHC Class II-Ii protein complexes are transported from the endoplasmic reticulum to a post-Golgi compartment where Ii is released by proteolysis and a specific antigenic peptide becomes bound to the MHC Class II molecule.

Class II MHC molecules are expressed primarily on cells involved in initiating and sustaining immune responses, such as T-lymphocytes, B-lymphocytes, and macrophages. Complexes of Class II MHC molecules and immunogenic peptides are recognized by helper T-lymphocytes (also known as helper/accessory T-cells, "Th") and induce proliferation of Th lymphocytes. Class II MHC complexes also stimulate secretion of cytokines by Th cells, resulting in amplification of the immune response to the particular immunogenic peptide that is displayed. Th1 cells produce interferon-γ and other cytokines that stimulate CTLs, while other cytokines produced by Th2 cells help B-cells to produce antibodies.

A second antigen processing pathway is generally involved with foreign or aberrant proteins made within cells, such as virus-infected or malignant cells. These proteins are subjected to partial proteolysis by the proteosome within such cells, so as to form peptide fragments that then associate with Class I MHC molecules and are transported to the cell surface for presentation to T-cells. Class I MHC molecules are expressed on almost all nucleated cells, and complexes of Class I MHC molecules and bound immunogenic peptides are recognized by CTLs, which then destroy the antigen-bearing cells. CTLs are particularly important in tumor rejection and in fighting viral infections.

For a CTL to recognize an antigen in the form of a peptide fragment bound to the MHC class I molecule, that antigen must normally be endogenously synthesized by the cell and a portion degraded into small peptide fragments in the cytoplasm. Some of these small peptides translocate into a pre-Golgi compartment and interact with Class I heavy chains to facilitate proper folding and association with the subunit 132 microglobulin. The peptide-MHC Class I complex is then routed to the cell surface for expression and potential recognition by specific CTLs.

By these dual antigen processing pathways, appropriate defenses are generated against both exogenous and internally produced antigens. Thus, antigens taken up from the extracellular environment eventually elicit B-cells to produce antibodies that protect the organism against a subsequent challenge by an agent comprising the exogenous antigen. On the other hand, antigens comprised of abnormal structures made within an abnormal or errant cell (for example a virus-infected or malignant cell) activate an immune response that eventually leads to killing of the errant cell. There is considerable interest in methods for better stimulating immune responses to antigens that are processed by either of these two pathways and presented by either MHC Class I or Class II molecules.

In view of the above knowledge, it is understandable that there has been substantial interest in using short peptides to affect an immune response in vivo and in vitro, to provide stimulation or inactivation of a particular response. Thus, appropriate immunogenic peptides might modulate a natural immune response to a particular event, either by activating particular lymphocytes to enhance a protective response or by deactivating particular lymphocytes to diminish or prevent an undesirable response.

The human immunodeficiency virus (HIV-1, also referred to as HTLV-III, LAV or HTLV-III/LAV) is the etiological agent of the acquired immune deficiency syndrome (AIDS) and related disorders (see, for example, Barre-Sinoussi et al., *Science* 220:868-871, 1983; Gallo et al., *Science* 224:500-503, 1984; Levy et al., *Science* 225:840-842, 1984; Siegal et al., *N. Engl. J. Med* 305:1439-1444, 1981). AIDS patients usually have a long asymptomatic period followed by the progressive degeneration of the immune system and the central nervous system. Replication of the virus is highly regulated, and both latent and lytic infection of the CD4 positive helper subset of T-lymphocytes occur in tissue culture (Zagury et al., *Science* 231:850-853, 1986). Molecular studies of HIV-1 show that it encodes a number of genes (Ratner et al., *Nature* 313:277-284, 1985; Sanchez-Pescador et al., *Science* 227:484-492, 1985), including three structural genes—gag, pol and env—that are common to all retroviruses. Nucleotide sequences from viral genomes of other retroviruses, particularly HIV-2 and simian immunodeficiency viruses (SIV; previously referred to as STLV-III), also contain these structural genes (Guyader et al., *Nature* 326: 662-669, 1987; Chakrabarti et al., *Nature* 328:543-547, 1987).

Development of an effective HIV vaccine is a major challenge due to antigenic variation and immune escape mechanisms. Strategies that include the use of recombinant DNA technology and novel antigen delivery methods are being applied to the development of HIV vaccines. Most HIV-1 vaccine constructs (DNA and recombinant protein vaccine) are subtype-specific and designed to prime only one arm of the immune system, that is, CTL responses or humoral B-cell responses. Emerging data suggest that broadly reactive T-cell responses, as well as neutralizing antibody responses are likely to be required for an effective immune response against HIV-1. Additionally, current human phase III vaccine trials using recombinant envelope proteins, suggest that immunity to HIV-1 envelope proteins is probably not sufficient for complete protection against HIV-1. Thus the results from multiple studies suggest that additional epitopes as well as activation of both arms of the immune system may be required for an effective HIV-1 vaccine.

By way of one example of peptide immunogens, Peter et al. (*Vaccine* 19:4121-4129, 2001) disclose induction of a CTL response against multiple CTL epitopes present in HIV proteins using short synthetic peptides. Four IHLA-A2.1 restricted peptides (RT 476-484, p17 77-85, gp41 814-823, RT 956-964) that showed stable binding to the HLA-A2.1 molecule in an in vitro binding assay were able to elicit a strong specific immune response in HLA-A2.1 transgenic mice when injected with a peptide ("P30") used as a universal T-cell helper epitope, in incomplete Freund adjuvant (IFA) or a nonionic emulsifier (Montanide™ ISA 720). The use of biodegradable poly-L-glutamic acid (PLGA) microspheres (MS) as adjuvant was also successfully tested for all peptides.

Many studies of cross-clade recognition of HIV epitopes have been carried out (see, for example, Wilson et al., *AIDS Res. Hum. Retroviruses* 14:925-937, 1998; McAdam et al., *AIDS* 12:571-579, 1998; Lynch et al., *J Infect Dis.* 178:1040-1046, 1998; Boyer et al. *Dev. Biol. Stand.* 95:147-53, 1998; Cao et al., *J. Virol.* 71:8615-8623, 1997; Durali et al., *Viral.* 72:3547 3553, 1998). These studies often used whole-gene, vaccinia-expressed constructs to probe CTL lines from HIV-1 infected or HIV-1 vaccinated volunteers for CTL responses. What appeared to be cross-clade recognition by CTLs in these experiments may have been recognition of CTL epitopes that are conserved within the large gene constructs cloned into the vaccinia constructs and into the vaccine strain (or the autologous strain). Where responses to specific peptides, and their altered sequences in other HIV strains, have been tested, and the peptides have been mapped, some studies have shown a lack of cross-strain recognition (Dorrel et al., HIV Vaccine Development Opportunities And Challenges Meeting, Abstract 109 (Keystone, Colo., January 1999)). Studies of virus escape from CTL recognition carried out on HIV-1 infected individuals have also shown that viral variation at the amino acid level may abrogate effective CTL responses (Koup, *J. Exp. Med.* 180:779-782, 1994; Dai et al., *J. Virol.* 66:3151-3154, 1992; Johnson et al., *J. Exp. Med.* 175:961-971, 1992).

Unfortunately, existing candidate HIV-1 vaccines are subtype specific, and are expected not protect against diverse natural HV-1 infections. This is true of both DNA vaccine constructs as well as recombinant protein vaccines. Furthermore, many of the existing constructs have focused on priming only one arm of the immune system, that is, cell mediated T-cell responses or humoral B-cell responses. In addition, while some DNA constructs have shown promising results in lowering viremia in animal model systems, none has been able to confer sterilizing immunity. These data suggest that both B-cell and T-cell responses may be needed for a protective immune response against HIV-1. Additionally, current human phase 3 vaccine trials using recombinant envelope proteins, suggests that immunity to HIV-1 envelope proteins is probably not sufficient for complete protection against HIV-1. Prime-boost strategy using recombinant envelope from HIV-1 subtype B also has not been successful in boosting the immune responses.

As the HIV epidemic continues to spread world wide, the need for effective immune-stimulatory compositions and vaccines remains urgent.

SUMMARY OF THE DISCLOSURE

Multi-clade multivalent (MCMV) (polyepitope; multi-epitope) polypeptides and mixtures of polypeptides have been developed, which can be used to stimulate immune responses to HIV-1 in vertebrates. In various embodiments, these polypeptides and polypeptide mixtures include immunogenic CTL, T- and/or B-cell determinants that are capable of eliciting broad and effective immune responses against diverse subtypes of HIV-1. Immunogens described herein are designed to be subtype-independent and will provide both prime and boost reagents for worldwide use.

Also described herein are recombinant MCMV constructs that can be used directly or indirectly to protect subjects against infection by multiple HIV-1 subtypes. These constructs are designed to elicit T-cell, B-cell, or both T-cell and B-cell responses against highly conserved epitopes within multiple HIV-1 subtypes. The constructs, when integrated into a vector, can be used as immunogens, can be used as DNA vaccines, and can be used as sources of recombinant protein for stimulation of immune responses in subjects, as well as for protein boosts to subjects who have received a nucleic acid construct previously.

Without being bound by theory, it is believed that the MCMV HIV-1 constructs and polypeptides provide universal immune stimulants and vaccines, capable of effective use in any part of the world affected by the HIV-1 epidemic.

The construction and design of specific provided constructs are particularly useful in that they allow convenient addition/deletion of epitopes, and contain specific cellular targeting domains that optimize antigen processing and recognition.

The provided constructs and proteins encoded thereby also can be combined with other epitope-based constructs to generate, for instance, multi-pathogen vaccines.

The foregoing and other features and advantages will become more apparent from the following detailed description of several embodiments, which proceeds with reference to the accompanying figures.

BRIEF DESCRIPTION OF THE FIGURES

FIG. 1 is a series of schematic drawings of embodiments of specific multi-clade, multivalent gene constructs.

SEQUENCE LISTING

Figure 1A:
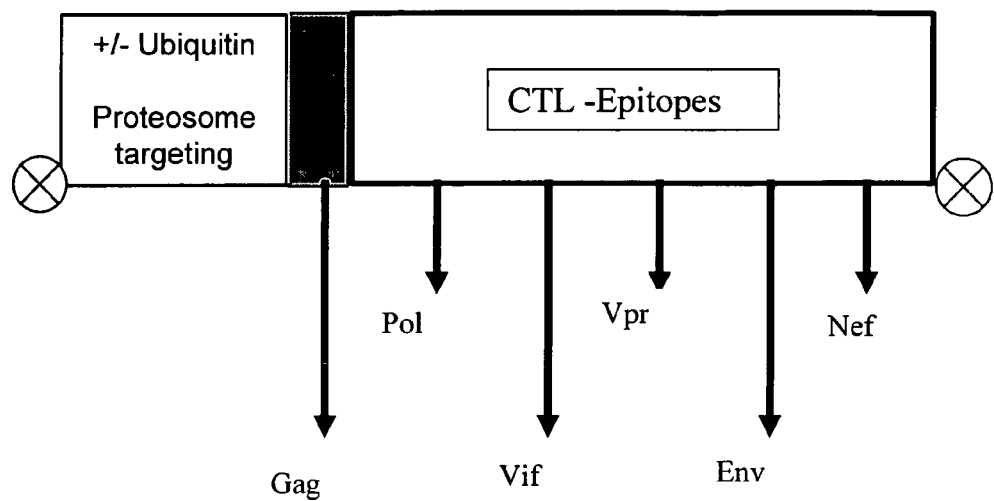
FIG. 1A shows one embodiment of a CTL-stimulating MCMV (MCMV-CTL) construct. Epitopes were chosen based on prior responses of HIV+ individuals, predicted HLA binding and sequence conservation among multiple HIV subtypes. In the Examples provided below, such a gene construct was assembled using synthetic single stranded oligonucleotides (100-130 mers) that contain strings of 3-6 CTL epitopes and linker amino acid sequences (exemplified by the tri-amino acid KAA), which were included to improve processing of epitopes. A modified human ubiquitin peptide is optionally added to the amino terminus of the molecule to further increase CTL epitope processing.
Figure 1B:
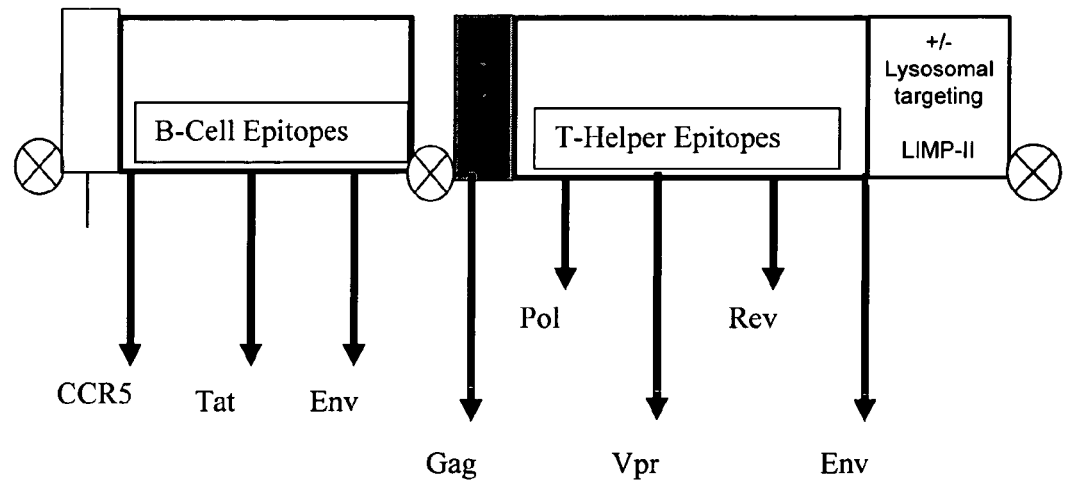
FIG. 1B shows one embodiment of a MCMV-AB/Th construct. Antibody and T-helper epitopes conserved among multiple subtypes of HIV-1 were chosen and single stranded oligos (100-120 mers) for these epitopes were synthesized. The lysosomal integral membrane protein-II (LIMP-II) signal sequence is optionally included to enhance processing of T-helper epitopes.
Figure 1C:
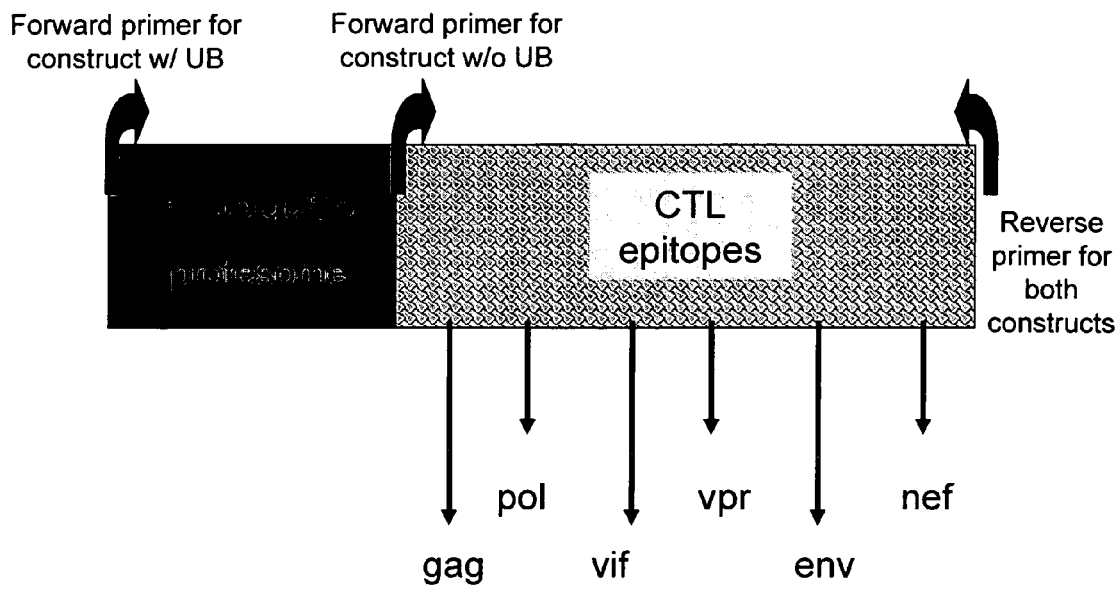
FIG. 1C is a schematic illustration of a MCMV-CTL, illustrating that the same nucleic acid construct can be used to generate both ubiquitin+ and ubiquitin-sequences by differential placement of the forward primer used to amplify the sequence.
Figure 1D:
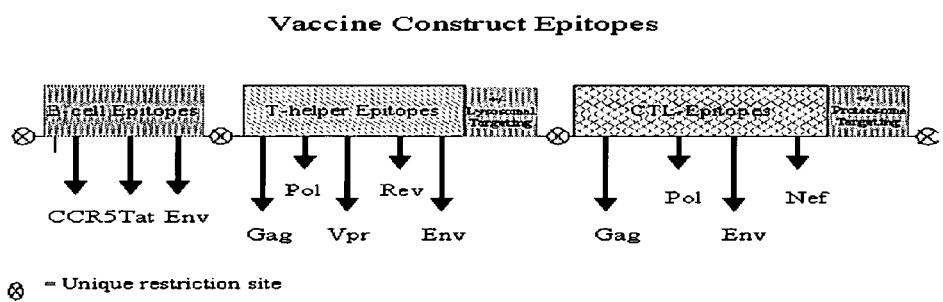
FIG. 1D shows an alternative embodiment, in which both the CTL and the AB/Th epitopes are provided in the same recombinant construct. In a combined construct such as this, the order of the different epitope sets can be rearranged.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows the nucleic acid sequence and amino acid sequence of MCMV-CTL-ubiquitin. The nucleic acid sequence includes unique restriction sites at positions 6-11 and 1548-1553. These restriction sites can be used to insert the epitope construct into different vectors.

SEQ ID NO: 2 shows the amino acid sequence of MCMV-CTL-ubiquitin. Ubiquitin is positions 1-76. The "KAA" spacer peptide appears (amino acid positions 117-119, 169-172, 242-244, 288-290, 317-319, 367-369, 417-419, and 466-468) throughout the remainder of the sequence between strings of three to five CTL epitopes.

SEQ ID NO: 3 shows the nucleic acid sequence and amino acid sequence of MCMV-CTL (no ubiquitin). The nucleic acid sequence includes unique restriction sites at positions 1-6 and 1318-1323. These restriction sites can be used to insert the epitope construct into different vectors.

SEQ ID NO: 4 shows the amino acid sequence of MCMV-CTL (no ubiquitin). The "KAA" spacer appears throughout the sequence, at positions analogous to those in SEQ ID NO: 2.

SEQ ID NO: 5 shows the amino acid sequence of CTLUbiquitinNC (without mouse and monkey control epitopes).

SEQ ID NO: 6 shows the amino acid sequence of CTLNC (no ubiquitin, without mouse and monkey control epitopes).

SEQ ID NO: 7 shows the nucleic acid sequence and amino acid sequence of MCMV-AB/Th with LIMP-II.

SEQ ID NO: 8 shows the amino acid sequence of MCMV-AB/Th with LIMP-II.

SEQ ID NO: 9 shows the nucleic acid sequence and amino acid sequence of MCMV-AB/Th without LIMP-II.

SEQ ID NO: 10 shows the amino acid sequence of MCMV-AB/Th without LIMP-II.

SEQ ID NOs: 11-22 show the amino acid sequences of additional HIV-1 CTL antigenic fragments/epitopes.

SEQ ID NOs: 23-45 show the amino acid sequences of control peptides.

SEQ ID NOs: 46-59 show the amino acid sequences of additional HIV-1 B-cell antigenic fragments/epitopes.

SEQ ID NOs: 60-64 show the amino acid sequences of additional HIV-1 T-helper cell antigenic fragments/epitopes.

DETAILED DESCRIPTION

I. Abbreviations

| | |
|---|---|
| HIV | human immunodeficiency virus |
| LIMP-II | lysosomal integral membrane protein II |
| MCMV | multi-clade multivalent |
| MCMV-AB/Th | B-cell/T-cell epitopes MCMV construct/polypeptide |
| MCMV-CTL | CTL epitopes MCMV construct/polypeptide |
| PCR | polymerase chain reaction |
| SOE | splicing overlap extension |

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the invention, the following explanations of specific terms are provided:

Adjuvant: A substance that non-specifically enhances the immune response to an antigen. Development of vaccine adjuvants for use in humans is reviewed in Singh et al., *Nat. Biotechnol.* 17:1075-1081, 1999, which discloses that, at the time of its publication, aluminum salts and the MF59 microemulsion are the only vaccine adjuvants approved for human use.

Binding or stable binding (of an oligonucleotide): An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. Binding may be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

A thorough treatment of the qualitative and quantitative considerations involved in establishing binding conditions that allow one skilled in the art to design appropriate oligonucleotides for use under the desired conditions is provided by Beltz et al., *Methods Enzymol.* 100:266-285, 1983, and by Sambrook et al. (ed), *Molecular Cloning: A Laboratory Manual*, 2nd ed., vol. 1-3, Cold Spring Harbor Laboratory Press, Cold Spring Harbor, N.Y., 1989.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a doublestranded DNA molecule. Thus, a reference to the nucleic acid molecule that encodes a particular MCMV construct, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA, the regions on either side of the removed sequence being joined together. Similar, this term can refer to the removal (for example, though genetic engineering means) of an amino acid sequence within a protein, the regions on either side of the removed sequence being joined together.

Epitope tags: Short stretches of amino acids to which a specific antibody can be raised, which in some embodiments allows one to specifically identify and track the tagged protein that has been added (for instance) to a living organism or to cultured cells. Detection of the tagged molecule can be achieved using a number of well known techniques. Examples of such techniques include (but are not limited to): immunohistochemistry, immunoprecipitation, flow cytometry, immunofluorescence microscopy, ELISA, immunoblotting ("western" blotting), and affinity chromatography. Examples of well known epitope tags include FLAG, T7, HA (hemagglutinin) and myc. The FLAG tag (DYKDDDDK) is beneficially used in some embodiments because high quality reagents are available to be used for its detection.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

Isolated: An "isolated" biological component (such as a nucleic acid molecule, protein or organelle) has been substantially separated or purified away from other biological components in the cell of the organism in which the component naturally occurs, that is, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Lysosomal compartment: Membrane-bound acidic vacuoles containing lysosomal-associated membrane protein (LAMP) molecules in the membrane, hydrolytic enzymes that function in antigen processing, and MHC class II molecules for antigen recognition and presentation. This compartment functions as a site for degradation of foreign materials internalized from the cell surface by any of a variety of mechanisms including endocytosis, phagocytosis and pinocytosis, and of intracellular material delivered to this compartment by specialized autolytic phenomena (de Duve, *Eur. J. Biochem.* 137:391, 1983).

The biosynthesis and vacuolar targeting mechanisms of the hydrolytic enzymes present in the lysosomal compartment have been extensively studied (Kornfeld & Mellman, *Ann. Rev. Cell Biol.,* 5:483, 1989). Newly synthesized hydrolases in the Golgi apparatus acquire mannose 6-phosphate groups that serve as specific recognition markers for the binding of these enzymes to mannose 6-phosphate receptors which are then targeted in some unknown manner to a prelysosomal vacuole. There the receptor-enzyme complex is dissociated by low pH, and the receptors recycle to the Golgi apparatus, while the enzyme-containing vacuole matures into a lysosome.

Studies of the structure and function of the lysosomal membrane were initiated in 1981 by August and colleagues with the discovery of major cellular glycoproteins that were subsequently termed LAMP-1 and LAMP-2 due to their predominant localization in the lysosomal membrane. Analogous proteins were subsequently identified in rat, chicken and human cells. Typically, LAMP-1, as deduced from a cDNA clone (Chen et al., *J. Biol. Chem.,* 263:8754, 1988) consists of a polypeptide core of about 382 amino acids (~42,000 Da) with a large (346-residue) intraluminal amino-terminal domain followed by a 24-residue hydrophobic transmembrane region and short (12-residue) carboxyl-terminal cytoplasmic tail. The intraluminal domain is highly glycosylated, being substituted with about 20 asparagine linked complex-type oligosaccharides and consists of two ~160-residue homology units that are separated by a proline/serine-rich region. Each of these homologous domains contains four uniformly spaced cysteine residues, disulfide bonded to form four 36-38-residue loops symmetrically placed within the two halves of the intraluminal domain (Arterburn et al., *J. Biol. Chem.*, 265:7419, 1990). The LAMP-2 molecule is highly similar to LAMP-1 in overall amino acid sequence (Cha et al., *J. Biol. Chem.*, 265:5008, 1990).

Another glycoprotein, described as CD63, MEA491 or LIMP-I, is also found in lysosomal membranes, as well as other in vacuolar structures (Azorza et al., *Blood,* 78:280, 1991). This molecule is distinctly different from the LAMPs, with a core polypeptide of about 25,000 Da and four transmembrane domains, but it has a cytoplasmic structure and sequence similar to the LAMP molecules. There is also extensive amino acid sequence similarity between this protein and a family of other molecules that also contain four membrane spanning domains, including the *Schistosoma mansoni* membrane protein SM23, CD37, the tumor-associated antigen CO-029, and the target of antiproliferative antibody-1.

LIMP-II is an additional glycoprotein present in the membrane of lysosomes and secretory granules with lysosomal properties (Vega et al., *J. Biol. Chem.*, 266:16818, 1991). A sequence near the amino-terminus with properties of an uncleavable signal peptide and a hydrophobic amine acid segment near the carboxyl end suggest that the protein is anchored in cell membranes at two sites by two short cytoplasmic tails at the amine and carboxyl-terminal ends of the protein. The molecule does not have sequence homology to any of the other described lysosomal membrane protein, but is highly similar to the cell surface protein CD36, which is involved in cell adhesion.

Nucleotide: This term includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include PNA molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide/polypeptide/protein.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: The pharmaceutically acceptable carriers useful with compositions described herein are conventional. Martin, *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Probes and primers: A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989 and Ausubel et al. *Short Protocols in Molecular Biology,* $4^{th}$ ed., John Wiley & Sons, Inc., 1999.

Primers are short nucleic acid molecules, for instance DNA oligonucleotides 10 nucleotides or more in length, for example that hybridize to contiguous complementary nucleotides or a sequence to be amplified. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the PCR or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Methods for preparing and using nucleic acid probes and primers are described, for example, in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989; Ausubel et al. *Short Protocols in Molecular Biol-*

*ogy*, 4th ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as Primer (Version 0.5, ©1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

Protein: A biological molecule, particularly a polypeptide, expressed by a gene and comprised of amino acids.

Purified: The term "purified" does not require absolute purity (for example, the absence of all other substances); rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

Specific binding agent: An agent that binds substantially only to a defined target. Thus a protein-specific binding agent binds substantially only the defined protein, or to a specific region within the protein. As used herein, a protein-specific binding agent includes antibodies and other agents that bind substantially to a specified polypeptide. The antibodies may be monoclonal or polyclonal antibodies that are specific for the polypeptide, as well as immunologically effective portions ("fragments") thereof.

Antibodies may be produced using standard procedures described in a number of texts, including Harlow and Lane, *Using Antibodies: A Laboratory Manual*, CSHL, New York, 1999. The determination that a particular agent binds substantially only to the target protein may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999). Western blotting may be used to determine that a given target protein binding agent, such as a monoclonal antibody, binds substantially only to the specified target protein.

Shorter fragments of antibodies can also serve as specific binding agents. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) FAb, the fragment which contains a monovalent antigen-binding fragment of an antibody molecule produced by digestion of whole antibody with the enzyme papain to yield an intact light chain and a portion of one heavy chain; (2) FAb', the fragment of an antibody molecule obtained by treating whole antibody with pepsin, followed by reduction, to yield an intact light chain and a portion of the heavy chain; two FAb' fragments are obtained per antibody molecule; (3) (FAb')$_2$, the fragment of the antibody obtained by treating whole antibody with the enzyme pepsin without subsequent reduction; (4) F(Ab')$_2$, a dimer of two FAb' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun or other acceleration techniques (for example, air gun).

Vaccine: A term used herein to mean a composition useful for stimulating a specific immune response (or immunogenic response) in a vertebrate. In some embodiments, the immunogenic response is protective or provides protective immunity, in that it enables the vertebrate animal to better resist infection with or disease progression from the organism against which the vaccine is directed. Without wishing to be bound by theory, it is believed that an immunogenic response may arise from the generation of neutralizing antibodies, T-helper, or cytotoxic cells of the immune system, or all of the above.

In some embodiments, an "effective amount" or "immune-stimulatory amount" of a vaccine or vaccinating composition is an amount which, when administered to a subject, is sufficient to engender a detectable immune response. Such a response may comprise, for instance, generation of an antibody specific to one or more of the epitopes provided in the vaccine. Alternatively, the response may comprise a T-helper or CTL-based response to one or more of the epitopes provided in the vaccine. All three of these responses may originate from naïve or memory cells. In other embodiments, a "protective effective amount" of a vaccine or vaccinating composition is an amount which, when administered to a subject, is sufficient to confer protective immunity upon the subject.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Virus: Microscopic infectious organism that reproduces inside living cells. A virus typically consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus type 1 and type 2, simian immunodeficiency virus, and feline immunodeficiency virus.

HIV is a retrovirus that causes immunosuppression in humans (HIV disease), and leads to a disease complex known as the acquired immunodeficiency syndrome. "HIV disease" refers to a well-recognized constellation of signs and symptoms (including the development of opportunistic infections) in persons who are infected by an HIV virus, as determined by antibody detection using ELISA or western blot studies. Alternatively, HIV infection can be detected by the presence of HIV RNA (for example, using RT-PCR) or HIV integrated DNA (for example, using PCR). Laboratory findings associated with this disease are a progressive decline in T-helper cells and a rise in viremia (viral load as determined by, for instance, RT-PCR).

Unless otherwise explained, all technical and scientific terms used herein have the same meaning as commonly understood by one of ordinary skill in the art to which this invention belongs. The singular terms "a", "an," and "the" include plural referents unless context clearly indicates otherwise. Similarly, the word "or" is intended to include "and" unless the context clearly indicates otherwise. Hence "comprising A or B" means including A, or B, or A and B. For example, the term "a cell" includes a plurality of cells, including mixtures of two or more types of cells. The term "a nucleic acid molecule" includes a plurality of nucleic acid molecules, or a mixture of different nucleic acid molecules. Similarly, the same holds for "a protein" or "a polypeptide."

As used herein, the term "comprising" shall mean that the compositions and methods include the recited elements, but do not exclude other elements. "Consisting essentially of" shall mean excluding other elements of any essential significance to the combination. Thus, a composition consisting essentially of the elements as defined herein would not exclude trace contaminants from the isolation and purification method and/or pharmaceutically acceptable carriers, such as phosphate buffered saline, preservatives, and the like. "Consisting of" shall mean excluding more than trace elements of other ingredients and/or excluding substantial additional method steps. Embodiments defined by each of these transition terms are within the scope.

It is further to be understood that all base sizes or amino acid sizes, and all molecular weight or molecular mass values, given for nucleic acids or polypeptides, are approximate and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein in various embodiments are multi-clade, multivalent recombinant polyepitope polypeptides, which are useful to induce immunogenic responses in vertebrate animals to HIV-1. These polypeptides include CTL-stimulatory epitopes, T-helper cell stimulatory epitopes, B-cell stimulatory epitopes, or combinations of two or more such types of epitopes. Epitopes in the polyepitope polypeptides are selected to provide multi-clade coverage. In particular, epitopes are selected to be at least 50% conserved across a plurality of HIV-1 subtypes, for instance, at least 2, 3, 4, 5, 6, or more HIV-1 subtypes. In particular embodiments, at least 30% of the epitopes included in a single polyepitope polypeptide are at least 60% conserved, at least 70% conserved, at least 80% conserved, or even more highly conserved across a plurality of HIV-1 subtypes.

In specific embodiments there are provided isolated polyepitope polypeptides, wherein adjacent polypeptide segments are linked by a spacer peptide. In some examples, the spacer peptide links multiple groups of polypeptide segments. Specific, non-limiting examples of the spacer peptide include the tri-amino acid lysine-alanine-alanine, or proline-glycine-proline.

In other examples, the isolated polyepitope polypeptides also include a targeting signal that targets the polyepitope polypeptides to a lysosome or to a proteosome. Specific, non-limiting, examples of the targeting signal include a targeting-competent fragment of lysosomal integral membrane protein-II or ubiquitin.

In still other examples, the isolated polyepitope polypeptides also include a plurality of amino acid segments from one or more HIV-1 coreceptors. A specific, non-limiting, example of a HIV-1 coreceptor is CCR5.

In further examples, the isolated polyepitope polypeptides include human cytotoxic T-lymphocyte stimulatory epitopes, human T-helper cell stimulatory epitopes, human B-cell stimulatory epitopes, or combinations of two or more epitopes thereof.

In additional embodiments there are provided isolated polyepitope polypeptides, which polypeptides comprise an amino acid sequence selected from the group consisting of sequences provided in SEQ ID NOs: 2, 4, 5, 6, 8 and 10. Also provided are mixtures of two or more isolated polyepitope polypeptides, including (but not limited to) mixtures of the polypeptides having sequences as shown in SEQ ID NOs: 2 and 8, 2 and 10, 4 and 8, 4 and 10, 5 and 8, 5 and 10, 6 and 8, and 6 and 10.

Other embodiments are isolated polynucleotides (nucleic acid molecules) which encode one of the polyepitope polypeptides described herein. Specific examples of such nucleic acid molecules comprise a sequence selected from the group consisting of sequences recited in SEQ ID NOs: 1, 3, 7, 9 and complements thereof. Other specific examples of nucleic acid molecules are the portions of each of SEQ ID NOs: 1, 3, 7, and 9 which correspond to and encode the polyepitope polypeptides shown in SEQ ID NOs: 2, 4, 8, and 10, respectively.

Also provided herein are genetic constructs that comprise at least one nucleic acid molecule encoding a polyepitope polypeptide, and host cells transformed with such a genetic construct.

Yet another embodiment is a composition comprising at least one polyepitope polypeptide or at least one nucleic acid molecule encoding a polyepitope polypeptide, and at least one component selected from the group consisting of pharmaceutically acceptable carriers and adjuvants. This disclosure further provides methods for eliciting and/or enhancing an immune response in a subject, which methods involve administering to the subject such a composition. In one specific, non-limiting example, the subject is infected with HIV-1

IV. Multi-Clade, Multivalent HIV-1 Constructs

The current disclosure provides multi-clade multivalent HIV-1 constructs useful for inducing immune responses in HIV-1-infected populations with diverse HLA alleles and HIV subtypes.

HIV-1 MCMV constructs comprise synthetic nucleic acid sequences to be used as HIV-1 immune-stimulatory and/or vaccine constructs to protect against multiple HIV-1 subtypes. These synthetic nucleic acid molecules or mixtures of nucleic acid molecules are designed to elicit both T-cell and B-cell responses against highly conserved epitopes within multiple HIV-1 subtypes. In specific embodiments, the synthetic genes are contained in plasmid constructs, which can be used as a DNA vaccine, as well as a source of recombinant protein for subsequent protein boosts.

Provided herein in various embodiments are multi-clade, multivalent polyepitope polypeptides, which are useful to induce immunogenic responses in vertebrate animals to HIV-1. These polypeptides include CTL-stimulatory epitopes, T-helper cell stimulatory epitopes, B-cell stimulatory epitopes, or combinations of two or more such types of epitopes. Epitopes in the polyepitope polypeptides are selected to provide multi-clade coverage. In particular, epitopes are selected to be at least 50% conserved across a plurality of HIV-1 subtypes, for instance, at least 2, 3, 4, 5, 6, or more HIV-1 subtypes. In particular embodiments, at least 30% of the epitopes included in a single polyepitope polypeptide are at least 60% conserved, at least 70% conserved, at least 80% conserved, or even more highly conserved across a plurality of HIV-1 subtypes.

One aspect of embodiments provided herein is that peptide sequences, each of which contains one or more antibody-binding or class I or class II MHC-binding epitopes, can be linked in tandem to form polyepitope polypeptides. These polyepitope polypeptides are proteolytically processed in cells to release the individual epitopes, and are useful for stimulating an immune response in a vertebrate animal.

When a MCMV polyepitope polypeptide is introduced into a cell, it is proteolytically processed into at least some of its constituent epitopes. At least some of the epitopes generated from the polypeptide can bind to MHC class I or MHC class II molecules present in the cell, though some of the epitopes may be specific for MHC class I or class II molecules present only on other cells. Included epitopes also may be B-cell epitopes, which elicit antibody-mediated immune responses upon binding to antibody receptors on the surface of a B-cell.

In one aspect, the disclosure features a nucleic acid encoding a polyepitope polypeptide that can include, in any order, a first, second, and third segment, each of which is at least nine amino acids in length. As used herein, a "segment" is an amino acid sequence which (a) corresponds to the sequence of a portion (that is, a fragment, less than all) of a naturally occurring protein, and (b) contains one or more epitopes. By "epitope" is meant a peptide which binds to the binding groove of an MHC class I or class II molecule, or to the antigen-binding region of an antibody. In addition, the polyepitope polypeptide can encode a targeting signal, for instance a peptide sequence that targets the protein to which it is fused to the lysosome or to the proteosome, as described in more detail herein.

In some embodiments, a segment of the polyepitope polypeptide has the amino acid sequence of a portion of (1) a naturally occurring HIV-1 protein or (2) a naturally occurring coreceptor (collectively referred to as "naturally occurring proteins"), that is at least nine amino acids in length. A second segment has the amino acid sequence of a second portion of the same or a different naturally occurring protein, is at least nine amino acids in length, and includes at least one epitope which is different from the epitope(s) of the first segment. Optionally, a third segment is included in the polyepitope polypeptide, and has the amino acid sequence of a third portion of the same or a different naturally occurring protein, is at least nine amino acids in length, and includes at least one epitope which is different from the epitope(s) of the first and second segments. Alternatively, the first, second and third portions may be portions of two or three different naturally occurring proteins (for example, two or three different HIV-1 proteins). The polyepitope polypeptide may optionally include additional segments, for example, it can include at least 4, 5, 10, 15, 20, 25, 30, 40, 50, 60, 75, 90 or even 100 or more segments, each being a portion of a naturally-occurring protein of a pathogenic agent and/or of a naturally occurring coreceptor which can be the same or different from the protein(s) from which the other segments are derived.

Each of these segments is at least nine amino acids in length, and each contains at least one epitope different from the epitope(s) of other segments in the polyepitope polypeptide. At least one (and in some embodiments, more) of the segments in the polyepitope polypeptide may contain class I or class II MHC-binding epitopes. Two, three, or more of the segments can be contiguous in the polyepitope polypeptide: that is, they are joined end-to-end, with no spacer between them. Alternatively, any two adjacent segments can be linked by a spacer amino acid or spacer peptide. In particular embodiments, the spacer comprises three amino acids. Specific non-limiting examples of spacers are the tri-amino acid KAA and the tri-amino acid PGP. Additionally, a spacer amino acid or spacer peptide can be used to link multiple groups of two, three, or more contiguous segments in the polyepitope polypeptide: that is, a spacer amino acid or spacer peptide is inserted between every two, three, or more segments.

A given segment of protein within the polyepitope polypeptide need not be any specified length, so long as it is sufficiently long to generate at least one epitope, for example, 2, 3, 4, 5, or more epitopes, and is at least 9 amino acids in length. For example, a given segment can have a length of at least 10 amino acids, for example, at least 11, 12, 13, 14, 15, 20, 25, 30, 40, or 50 amino acids. A given segment corresponds to a particular naturally occurring protein if any 9 (or more) consecutive amino acids of the segment are found in exactly the same order in a portion of the naturally occurring protein. In exemplary embodiments, the segments included in a polyepitope polypeptide are obtained from one or more HIV-1 proteins and/or coreceptors (for example, CCR5).

It is understood that the term "naturally occurring proteins" used above does not preclude modification of the sequence used in the polyepitope polypeptide, for instance by changing one or a few amino acids. In addition, it is understood that the nucleic acid molecule encoding the segment need not be identical to the "naturally occurring" sequence, as found in (for instance) the HV-1 genome. In particular, it is contemplated that the codon usage in the nucleic acid molecule can be modified, for instance to convert the encoding sequence to a codon optimized sequence. The codon optimization can be tailored for the host cell in which the construct will eventually be expressed. Thus, some constructs are engineered to be codon biased for expression in a prokaryotic cell, others to be expressed in a unicellular eukaryotic cell, and still others to be expressed in a cell of a multicellular eukaryote (for example, a vertebrate). Codon selection to take advantage of species biases is well known to those of ordinary skill.

The discovery of the HIV-1 coreceptors, together with a greater understanding of the Envelope-receptor mediated conformational changes resulting in the membrane fusion process, has identified several promising vaccine targets. These epitopes as well as others in the transmembrane envelope glycoprotein (gp41) have been identified as HIV-1 neutralizing epitopes. Likewise, epitopes in the CCR5 coreceptor have been identified as potential targets for interfering with receptor-env interactions. Any of these epitopes can be included in the polyepitope polypeptides described herein.

Construction of HIV-MCMV Immunogens

HIV-1-MCMV immunogen constructs comprised of a string of codon-optimized epitopes have been produced. The antigenic fragments/epitopes in examples of such constructs were selected using published studies including broad MHC allele recognition and were compiled from the Los Alamos sequence database. A representative pair of immunogen constructs (polyepitope polypeptides) contains multiple B-cell epitopes, CTL epitopes, and T-helper epitopes representing immunodominant regions for all subtypes of HIV-1 (see tables included in the examples, and FIGS. 1, 2, and 3). The epitopes chosen are >80% homologous across diverse HIV-1 subtypes. B-cell epitopes in the virus binding domain of the human HIV coreceptor CCR5 are also included.

Without intending to be limited to a single interpretation, it is believed that antibodies to CCR5 together with neutralizing antibodies directed against the HIV-1 envelope glycoprotein and strong T-cell immunity will interfere with the viral entry process and is expected to induce sterilizing immunity.

Example immunogen constructs are shown in SEQ ID NOs: 2, 4, 5, 6, 8, and 10. The constructs shown in SEQ ID NOs: 2, 4, 5, and 6 include CTL epitopes (and therefore can be referred to generally as MCMV-CTL constructs); those in SEQ ID NOs: 8 and 10 include B-cell and T-helper epitopes (and therefore can be referred to generally as MCMV-AB/Th constructs).

Unique restriction enzyme digestion sites have been included in the nucleic acid constructs encoding the provided polyepitope polypeptides. These facilitate addition/deletion of epitopes, as well as the shuttling of the polyepitope cassette between a number of DNA vectors, including DNA vaccine constructs (for example, pVax-1, Invitrogen, Carlsbad, Calif.), eukaryotic yeast expression vectors (for example, pYes, Invitrogen, Carlsbad, Calif.), and multi-cell type expression vectors (for example, pTriEX-4, Novagen, Madison, Wis.). This enables the production of both a DNA based immunogen and vaccine, and ready production recombinant polyepitope polypeptide, which can be used directly as an immunogen or as a boost. The synthetic genes (which encode one or more polyepitope polypeptides) also can be incorporated into attenuated viral vectors such as Modified Vaccinia or Adenovirus to serve as a boosting agent.

Delivery and Immunogenicity by Inclusion of Targeting Sequences

Recent studies suggest that peptide spacers between epitopes and/or targeting sequences may increase the immunogenicity of certain epitopes. Targeting sequences such as the LIMP-II targeting sequence (which directs proteins to lysosomes and enhances class-II recognition), or targeting-competent fragments thereof, are used in certain provided embodiments to help enhance T-helper response. Likewise, proteosome targeting sequences (for example, ubiquitin or targeting-competent fragments thereof) that help induce class I recognition are included in specific embodiments, to provide improved CTL production. The chosen epitopes were back translated and human codon optimized for increased expression from the DNA construct.

In any of the described nucleic acids encoding polyepitope polypeptides, a spacer amino acid or spacer peptide can be included between any two adjacent segments of the construct. Optionally, in some embodiments the spacer is included between each epitope; in other embodiments, a spacer is included between every two, every three, every four, every five epitopes, or even less often. In particular embodiments, the spacer comprises three amino acids. Specific non-limiting examples of spacers are the tri-amino acid KAA and the tri-amino acid PGP.

Recognition of Epitopes Contained in the Constructs

Most vaccine constructs under development are subtype-specific. This has led to development of a number of country-specific subtype-specific HIV-1 vaccines, however, such vaccines will be difficult to implement due to emerging diversity and changing epidemic of HIV-1.

In contrast, the constructs provided herein comprise highly conserved immunogenic regions of HIV-1 that result in cross-protective immune responses across HIV-1 subtypes. The immune responses to the immunogenic epitopes can be tested, for instance, in recently-infected HIV-1 infected persons (Primary HIV-1 infection; PHI) or individuals that have a slow progression to disease.

V. Uses of MCMV Immunogens

In order to function effectively in vivo as a DNA-based immunogen, it is advantageous to include within the MCMV nucleic acid construct a control sequence that has the effect of enhancing or promoting the translation of the sequences encoding the antigens. Use of such promoters is well known to those of skill in the fields of molecular biology, cell biology, and viral immunology (See, "Molecular Cloning: A Laboratory Manual", 2nd Ed., Sambrook, Fritsch and Maniatis, Cold Spring Harbor Laboratory, Cold Spring Harbor, N.Y., 1989; and "Current Protocols in Molecular Biology", Ausubel et al., John Wiley and Sons, New York 1987 (updated quarterly)).

In certain embodiments, the nucleic acid construct is intended for use as a vaccine in a mammalian host. Therefore it is advantageous to employ a promoter which operates effectively in mammalian cells. Particular embodiments relate to both prokaryotic and eukaryotic host cells. Many promoter sequences are known that are useful in either prokaryotic or eukaryotic host cells. A promoter is operably disposed with respect to the sequence(s) whose translation is to be promoted, so that it is capable of promoting translation. In certain embodiments, the promoter is the cytomegalovirus early promoter. In addition, in some embodiments, the sequences to be expressed are followed by a terminator sequence.

Preparation of the nucleic acids is readily accomplished by methods well known to workers of skill in the field of molecular biology. Procedures involved are set forth, for example, in Sambrook, Fritsch and Maniatis, Cold Spring Harbor Laboratory, Cold Spring Harbor, N.Y., 1989, and "Current Protocols in Molecular Biology", Ausubel et al., John Wiley and Sons, New York 1987 (updated quarterly). Incorporation of promoters, such as the cytomegalovirus promoter, and of the polyadenylation signal, is likewise well known to skilled practitioners in molecular biology and recombinant DNA engineering.

When a nucleic acid molecule harboring a MCMV epitope chain is prepared, it may be obtained in larger quantities by methods that amplify a nucleic acid fragment. Such methods are widely known to workers skilled in molecular biology and recombinant DNA engineering. Examples of these methods include incorporation of the nucleic acid fragment into a plasmid for replication by culturing in a cell (for example, a prokaryotic cell) and harvesting the plasmid after growth of the culture, as well as amplification of the nucleic acid fragment by nucleic acid amplification methods, such as the PCR. These methods are exemplary only, and not intended to limit the ways in which the nucleic acid construct may be obtained.

The MCMV nucleic acid constructs may be introduced into appropriate host cells in many ways well known to those of ordinary skill in the fields of molecular biology and viral immunology. By way of example, these include, but are not limited to, incorporation into a plasmid or similar nucleic acid vector which is taken up by the host cells, or encapsulation within vesicular lipid structures such as liposomes, especially liposomes comprising cationic lipids, or adsorption to particles that are incorporated into the host cell by endocytosis.

In general, a host cell is a prokaryotic or eukaryotic cell harboring a MCMV nucleic acid, or into which such a MCMV molecule has been introduced. The constructs described herein induce the intracellular biosynthesis of the encoded multivalent HIV-1 antigens. A suitable host cell is one which has the capability for the biosynthesis of the gene products as a consequence of the introduction of the nucleic acid. In particular embodiments, a suitable host cell is one which responds to a control sequence and to a terminator sequence, if any, which may be included within the construct. In order to respond in this fashion, such a host cell contains within it components which interact with a control sequence and with a terminator, and act to carry out the respective promoting and terminating functions. When the host cell is cultured in vitro, it may be a prokaryote, a single-celled eukaryote or a vertebrate cell. In particular embodiments, the host cell is a mammalian cell VI. Stimulation of Immunological Responses to HIV-1

With the provision herein of polyepitope polypeptide antigens specific to HIV-1, methods are now enabled for the stimulation of immune responses to such antigens in subjects. In certain embodiments, such immune responses will be protective against HIV-1 infection in the subject. MCMV polyepitope polypeptides (singly or in combination) can be used, for instance, as immunogenic agents in the inhibition, treatment, or amelioration of HIV-1. Subjects selected for this type of treatment are those who are known to have, or are suspected of having or are at risk of suffering, a HIV-1 infection.

The provided immunostimulatory MCMV polyepitope polypeptides, or constructs or vectors encoding such polypeptides, are combined with a pharmaceutically acceptable carrier or vehicle for administration as an immunostimulatory composition or a vaccine to human or animal subjects. In some embodiments, more than one polyepitope polypeptide may be combined to form a single preparation.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immunostimulatory agents or vaccines, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to about 1.0 ml. Those of ordinary skill in the art will know appropriate volumes for different routes of administration.

The amount of protein in each vaccine dose is selected as an amount that induces an immunostimulatory or immunoprotective response without significant, adverse side effects. Such amount will vary depending upon which specific immunogen is employed and how it is presented. Initial injections may range from about 1 µg to about 1 mg, with some embodiments having a range of about 10 µg to about 800 µg, and still other embodiments a range of from about 25 µg to about 500 µg. Following an initial vaccination, subjects may receive one or several booster immunizations, adequately spaced. Booster injections may range from about 1 µg to about 1 mg, with other embodiments having a range of about 10 µg to about 750 µg, and still others a range of about 50 µg to about 500 µg. Periodic boosters at intervals of 1-5 years, for instance three years, may be desirable to maintain the desired levels of protective immunity.

As described in WO 95/01441, the course of the immunization may be followed by in vitro proliferation assays of PBL (peripheral blood lymphocytes) co-cultured with ESAT6 or ST-CF, and especially by measuring the levels of IFN-released from the primed lymphocytes. The assays are well known and are widely described in the literature, including in U.S. Pat. Nos. 3,791,932; 4,174,384 and 3,949,064.

A relatively recent development in the field of immune stimulatory compounds (for example, vaccines) is the direct injection of nucleic acid molecules encoding peptide antigens (broadly described in Janeway & Travers, *Immunobiology: The Immune System In Health and Disease*, page 13.25, Garland Publishing, Inc., New York, 1997; and McDonnell & Askari, *N. Engl. J. Med.* 334:42-45, 1996). Plasmids (vectors) that include nucleic acid molecules described herein, or that include a nucleic acid sequence encoding an immunogenic MCMV polyepitope polypeptide may be utilized in such DNA vaccination methods.

Thus, the terms "immunostimulatory preparation" and "vaccine" as used herein also include nucleic acid vaccines in which a nucleic acid molecule encoding a MCMV polyepitope polypeptide is administered to a subject in a pharmaceutical composition. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264: 16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992; Eisenbraun et al., *DNA Cell Biol.* 12:791, 1993), and in vivo infection using cloned retroviral vectors (Seeger et al., *Proc. Natl. Acad. Sci.* 81:5849, 1984).

Similarly, nucleic acid vaccine preparations can be administered via viral carrier.

It is also contemplated that the provided immunostimulatory molecules and preparations can be administered to a subject indirectly, by first stimulating a cell in vitro, which stimulated cell is thereafter administered to the subject to elicit an immune response.

VII. Immunological and Pharmaceutical Compositions

Immunological compositions, including immunological elicitor compositions and vaccines, and other pharmaceutical compositions containing latency-specific polypeptides or antigenic fragments thereof are useful for reducing, ameliorating, treating, or possibly preventing HIV infection, particularly HIV-1 infection. One or more of the polypeptides are formulated and packaged, alone or in combination with adjuvants or other antigens, using methods and materials known to those skilled in the vaccine art. An immunological response of a subject to such an immunological composition may be used therapeutically or prophylactically, and in certain embodiments provides antibody immunity and/or cellular immunity such as that produced by T-lymphocytes, such as cytotoxic T-lymphocytes or $CD4^+$ T-lymphocytes.

The MCMV polyepitope polypeptides may be administered with an adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. (*J. Immunol* 147:410415, 1991), encapsulation of the conjugate within a proteoliposome as described by Miller et al. (*J. Exp. Med* 176:1739-1744, 1992), and encapsulation of the protein in lipid vesicles may also be useful.

The compositions provided herein, including those formulated to serve as vaccines, may be stored at temperatures of from about −100° C. to about 4° C. They may also be stored in a lyophilized state at different temperatures, including higher temperatures such as room temperature. The preparation may be sterilized through conventional means known to one of ordinary skill in the art. Such means include, but are not limited to, filtration, radiation and heat. The preparations also may be combined with bacteriostatic agents, such as thimerosal (ethyl(2-mercaptobenzoate-S)mercury sodium salt) (Sigma Chemical Co., St. Louis, Mo.), to inhibit bacterial growth.

A variety of adjuvants known to one of ordinary skill in the art may be administered in conjunction with the protein(s) in the provided vaccine composition. Such adjuvants include but are not limited to the following: polymers, co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; alum; QS 21, muramyl dipeptide; CpG oligonucleotide motifs and combinations of CpG oligonucleotide motifs; trehalose; bacterial extracts, including mycobacterial extracts; detoxified endotoxins; membrane lipids; or combinations thereof.

In a particular embodiment, a vaccine is packaged in a single dosage for immunization by parenteral (that is, intramuscular, intradermal or subcutaneous) administration or nasopharyngeal (that is, intranasal) administration. In certain embodiments, the vaccine is injected intramuscularly into the deltoid muscle. The vaccine may be combined with a pharmaceutically acceptable carrier to facilitate administration. The carrier is, for instance, water, or a buffered saline, with or without a preservative. The vaccine may be lyophilized for resuspension at the time of administration or in solution.

The carrier to which the polypeptide may be conjugated may also be a polymeric delayed release system. Synthetic polymers are particularly useful in the formulation of a vaccine to affect the controlled release of antigens.

Microencapsulation of the polypeptide will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters, polyamides, poly-(d,1-lactide-co-glycolide) (PLGA), and other biodegradable polymers.

Doses for human administration of a pharmaceutical composition or a vaccine may be from about 0.01 mg/kg to about 10 mg/kg, for instance about 1 mg/kg. Based on this range, equivalent dosages for heavier (or lighter) body weights can be determined. The dose may be adjusted to suit the individual to whom the composition is administered, and may vary with age, weight, and metabolism of the individual, as well as the health of the subject. Such determinations are left to the attending physician or another familiar with the subject and/or the specific situation. The vaccine may additionally contain stabilizers or physiologically acceptable preservatives, such as thimerosal.

The following examples are provided to illustrate certain particular features and/or embodiments. These examples should not be construed to limit the invention to the particular features or embodiments described.

EXAMPLES

Existing HIV-1 vaccine constructs are subtype specific. Though multiple sub-type specific candidate vaccines are under development, areas with high numbers of recombinant viruses would likely pose problems for subtype specific vaccines.

While the high degree of HIV variability has made vaccine design difficult, the proximity of populations with varying subtypes and the ease of travel have made a vaccine that can provide protection from multiple subtypes desirable. To address the problem of subtype variability, these examples illustrate production of constructs containing conserved B, T-helper, and CTL epitopes, with and without targeting domains. The chosen epitopes are expected to generate immune responses to multiple HIV-1 subtypes.

Selection of Epitopes

In order to assemble a set of CTL epitopes that were conserved across a wide range of HIV-1 subtypes and that would be recognized by a large percentage of the population, the following databases and sources of sequence were consulted: Los Alamos HIV Molecular Immunology Database, Described Epitopes, LTNPs, EU and the Los Alamos HIV Sequence Database. The literature was also consulted, to locate reported conserved epitopes.

The epitopes were selected based on conserved epitopes previously shown to be recognized by HIV-1-infected persons from published reports or the Los Alamos Data base. These antigenic fragments/epitopes were selected using the results of in vitro and in vivo protection studies compiled in the Los Alamos database, as well as using the Motifscan software program. The following table (Table 1) provides the list of the multiple epitopes in the highly conserved regions in gag (p17, p24) pol (Prt, RT and Int) as well as Nef, Vif, Vpr, and Env epitopes selected based on their MHC class I binding (CTLs).

Epitopes were selected that were greater than 50% conserved across all the available sequences. Of these, the majority of epitopes were >90% conserved for subtypes A/B/C/D/E/F/G. Also taken into consideration was the frequency of Class I alleles that would recognize each conserved epitope.

TABLE 1

| CTL | Region | Sequence | AA Position in SEQ ID NO:2 | HLA-alleles | Source |
|---|---|---|---|---|---|
| p17 | 18-29 | KIRLRPGGKKKY | 96-107 | A3, A3.1, B27, B42, Bw62 | Ferrari et al. ARHR |
| p17 | 36-44 | WASRELERF | 108-116 | B35 | 16: 1433-1443, |
| p17 | 74-92 | ELRSLYNTVATLYCVHQRI | 77-95 | B8, A2, A11 | 2000 |
| p24 | 15-27 | ISPRTLNAWVKVV | 120-132 | A2, B57 | |
| p24 | 30-55 | KAFSPEVIPMFSALSEGATPQDLNTM | 133-158 | B58, B44, B7 | |
| p24 | 108-117 | TSTLQEQIGW | 159-168 | B57 | |
| p24 | 121-150 | NPPIPVGDIYKRWIILGLNKIVRMYSPTSI | 172-201 | B8, B35, B27, B62, B52 | Ferrari et al. ARHR |
| p24 | 161-174 | FRDYVDRFYKTLRA | 202-215 | B18, B44, A24, B70, B14 | 16: 1433-1443, 2000, and Hanke et al., Nature Med 9: 951-955, 2000 |
| p24 | 191-205 | VQNANPDCKTILKAL | 216-230 | B51, B8, | Ferrari et al. ARHR |
| | 216-226 | ACQGVGGPGHK | 231-241 | A11 | 16: 1433-1443, 2000 |
| pol | 59-65 | ITLWQRPLV | 245-253 | A28, A6802 | Ferrari et al. ARHR 16: 1433-1443, 2000; Hanke et al., Nature Med 9: 951-955, 2000 |
| pol | 262-273 | TVLDVGDAYFSV | 254-265 | A2, A0201, B35 | Ferrari et al. ARHR 16: 1433-1443, 2000 |
| pol | 308-321 | WKGSPAIFQSSMTK (SEQ ID NO:11) | N/A | B7, B35, A11, A3, A33 | Ferrari et al. ARHR 16: 1433-1443, 2000; Hanke et al., Nature Med 9: 951-955, 2000 |
| pol | 464-472 | ILKEPVHGV | 308-316 | A2, A0201 | Ferrari et al. |
| pol | 495-507 | QIYQEPFKNLKTG | 320-332 | A11 | ARHR |
| pol | 587-602 | EPIVGAETFYVDGAAN | 333-348 | B35, B51, A28 | 16: 1433-1443, |
| pol | 956-964 | LLWKGEGAV | 358-366 | A2, A0201 | 2000 |
| pol | | VIYQYMDDL | 349-357 | A0201 | Hanke et al., Nature Med 9: 951-955, 2000 |
| vif | 48-57 | HPKVSSEVHI | 380-389 | B0702 | Altfeld et al, J. Immunology 167: 2743-2752 (non-B sequence was derived from sequence data contained in the Los Alamos HIV sequence database |

TABLE 1-continued

| CTL | Region | Sequence | AA Position in SEQ ID NO:2 | HLA-alleles | Source |
|---|---|---|---|---|---|
| Vif | 17-26 | RIRTWKSLVK | 370-379 | A0301 | Altfeld et al, J. Immunology 167: 2743-2752 |
| vprB | 29-42 | AVRHFPRIWLHSL (SEQ ID NO:12) | N/A | B5701 | |
| vpr nonB | 29-42 | AVRHFPRPWLHGL (SEQ ID NO:13) | N/A | B7301* | Altfeld et al, J. Immunology 167: 2743-2752 (non-B sequence was derived from sequence data contained in the Los Alamos HIV sequence database) |
| vpr | 58-66 | AIIRILQQL | 408-416 | A0201 | Altfeld et al, J. Immunology 167: 2743-2752 |
| nef | 64-95 | VGFPVRPQVPLRPMTY KGAVDLSHFLKEKGGL | 420-451 | A11, B8, B35, B7, A3, A2, | Ferrari et al. ARHR 2000 |
| nef | 127-141 | GPGVRYPLTFGWCY | 452-465 | B57 | 16: 1433-1443, Hanke et al., Nature Med 9: 951-955, 2000 |
| gp120 | 36-51 | TVYYGVPVWKEATTTL | 478-493 | A3, B35, B55 | Ferrari et al. |
| gp120 | 120-128 | KTLPLCVTL | 469-477 | A2 | ARHR |
| gp41 | 47-55 | RAIEAQQHL | 494-502 | B51 | 16: 1433-1443, 2000 |
| gp41 | | ERYLKDQQL (SEQ ID NO:14) | N/A | B14, A24, B8 | Hanke et al., Nature Med |
| SIV p27 | | ACTPYDINQML | 291-301 | MONKEY Mamu-A*01 | 9: 951-955, 2000 |
| gp120 | | RGPGRAFVTI | 278-287 | Mouse H-2D | |

These epitopes can be further characterized in summary as follows:

TABLE 2

| Epitope | # of Epitopes | HLA |
|---|---|---|
| p17 | 6 | A3, A3.1, B27, B42, Bw62, B35, B8, A2, A11 |
| p24 | 20 | B57, A2, B58, B44, B7, B57, B8, B35, B27, B2, B52, B18, B44, A24, B70, B14, B51, B8, B8, A11 |
| pol | 10 | A28, B35, A2, A0201, B7, B35, A11, A3, A2, A0201, A11, B35, B51, A28, A2, A0201 |
| nef | 8 | A1, B8, B35, B7, B35, A3, A11, A2, B35, A11, B8, B57 |
| gp120 | 4 | A3, B55, B35, A2 |
| gp-41 | 2 | B51, B14 |
| Vif | 2 | B0702, A0301 |
| Vpr | 3 | B5701, B7301, A0201 |
| SIVp27/gp120[1] | 2 | MAMU-A*01/Mouse H-2D |

[1]Control epitopes included for animal studies; SIVp27 is a simian epitope; the gp120 epitope is known to be recognized by the murine H-2D HLA.

CTL/Proteosome Constructs

FIG. 1A shows the schematic map of one synthetic construct prepared to encode the identified conserved CTL epitopes. Representative nucleotide and amino acid sequences of HIV-1-MCMV-CTL with and without ubiquitin are shown in the accompanying Sequence Listing.

Figure 2A:
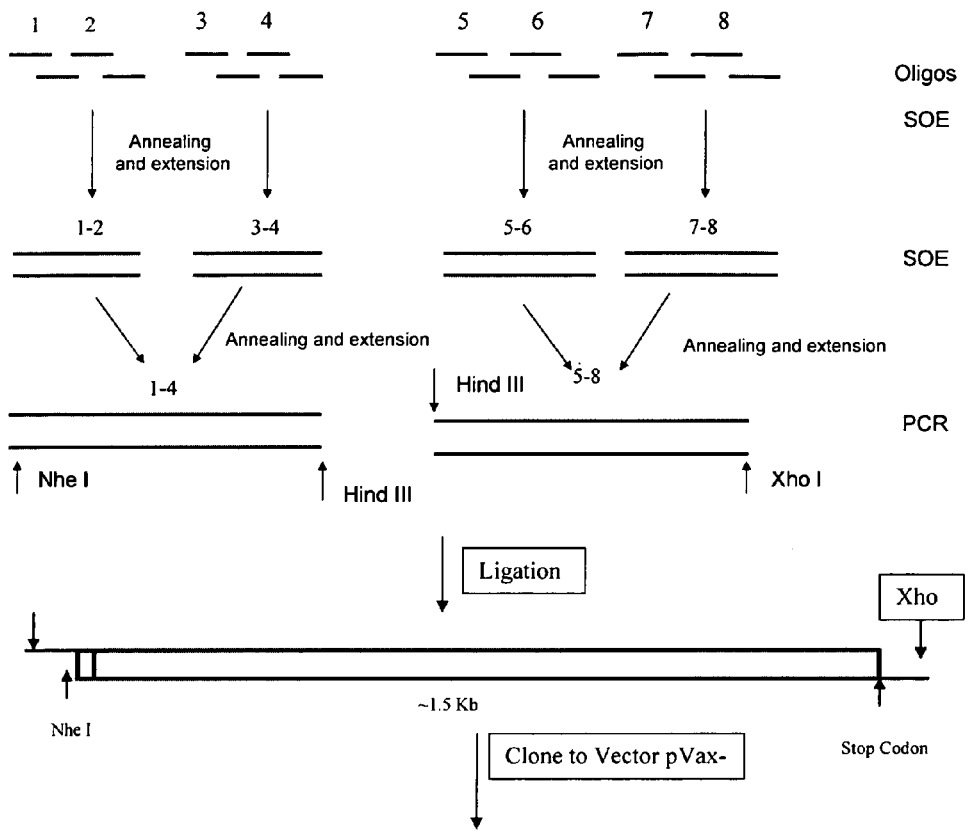
FIG. 2 is a schematic illustration of the assembly of representative MCMV construct. In the illustrated embodiment (FIG. 2A), overlapping single stranded oligonucleotides (100-130 mers), spanning the full length of the MCMV-CTL-ubiquitin construct (1.5 kb) were synthesized (eight forward and eight reverse). Through a series of splicing overlap extension (SOE), polymerase chain reaction (PCR) and cloning steps, a 1,553 base pair recombinant nucleic acid sequence was generated and then cloned into pVax-1 (Invitrogen, Carlsbad, Calif.) (FIG. 2B). Alternatively, the construct was also assembled without including ubiquitin (FIG. 2C).
Figure 2B:
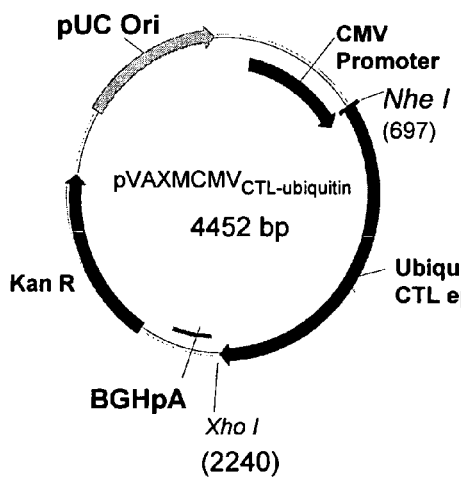
Figure 2C:
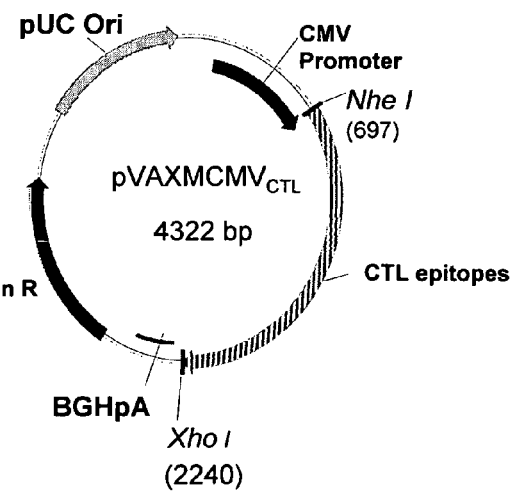
Figure 3:
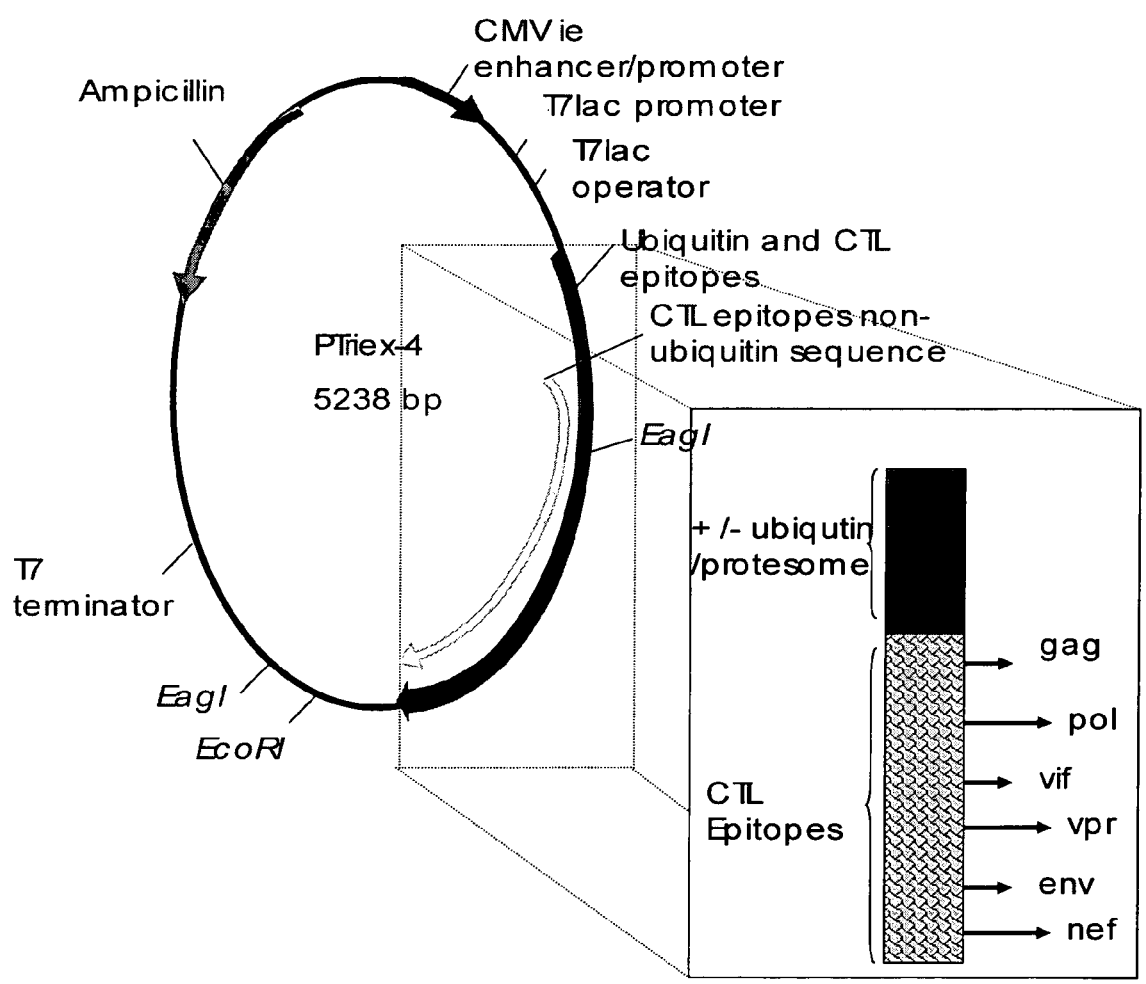
FIG. 3 is an schematic drawing of vector PTriex-4 (Novagen, Madison, Wis.), which contains a representative MCMV-CTL construct, which can be used for production of recombinant protein in either bacterial, mammalian or insect cells.
Figure 4:
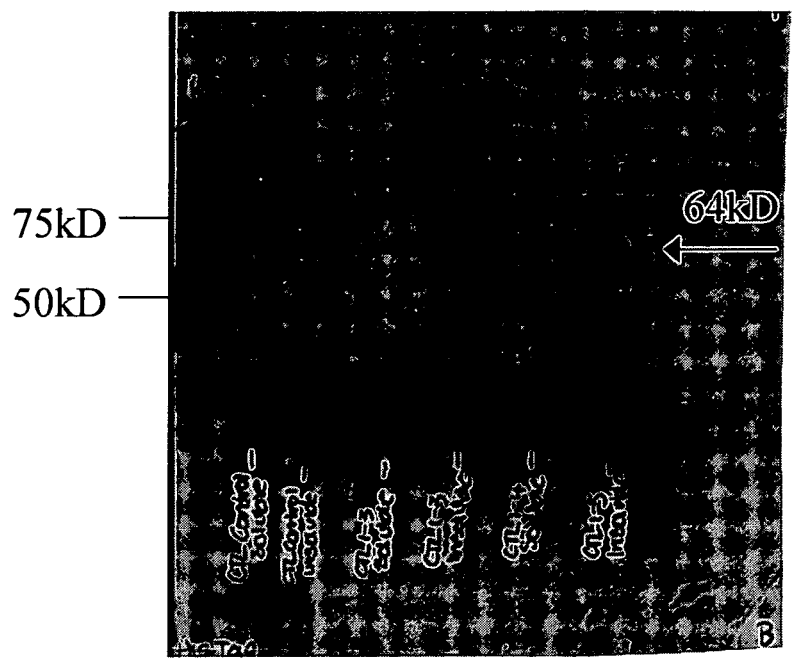
FIG. 4 is a western blot analysis showing expression of a MCMV-CTL-ubiquitin polypeptide fusion construct in $E.$ $coli.$ The fusion protein is predicted to be 64 kDa (57 kDa plus the 7 kDa expression tag); expressed protein is indicated in the right hand most lane.
Figure 5:
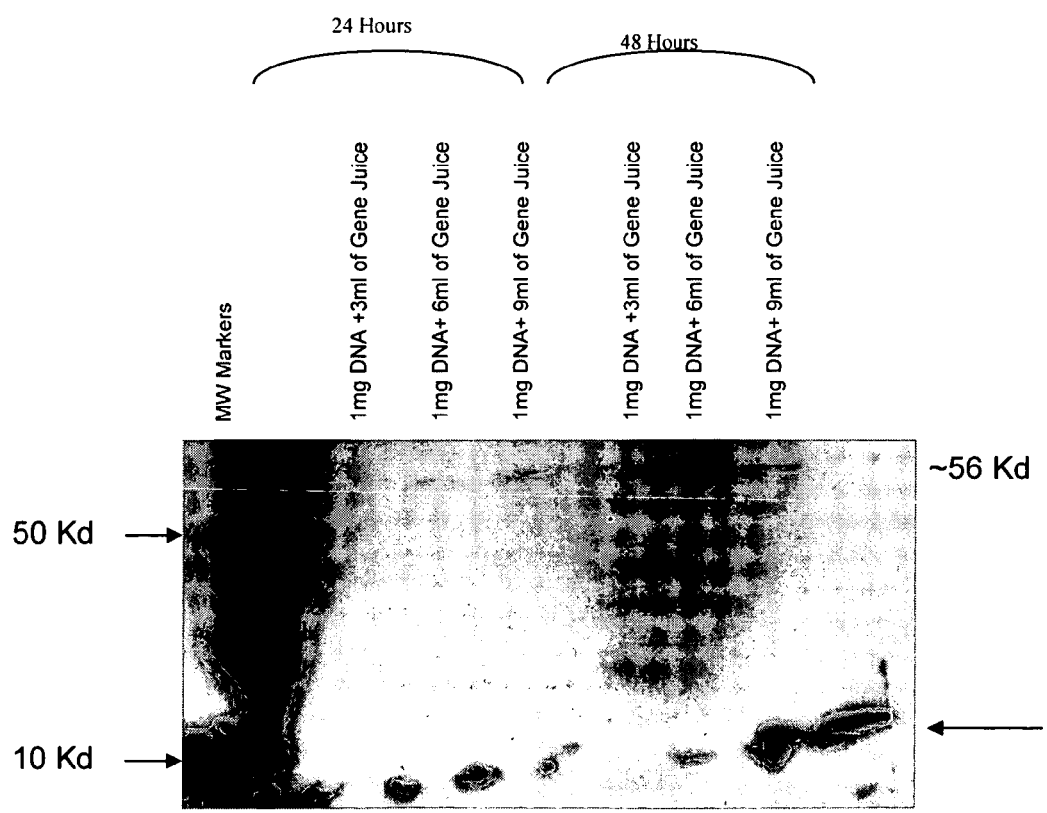
FIG. 5 is a western blot analysis of extract from HeLa cells transfected with pVax-1 (Invitrogen, Carlsbad, Calif.) containing the MCMV-CTL-ubiquitin sequence, using an anti-ubiquitin antibody for detection. Cells were transfected using various concentrations of GeneJuice reagent (Merck Biosciences, San Diego, Calif.) with 1 μg of DNA. Cells were harvested 24 and 48 hours post transfection. A ubiquitinated protein of the correct predicted molecular weight (~56 kDa) of the synthetic MCMV-CTL-ubiquitin construct is clearly visible, as is normal cellular ubiquitin (~10 kDa).

Using the 55 conserved CTL epitopes identified as described above, a synthetic gene was constructed using SOE followed by PCR. The synthesis is illustrated in FIG. 2A. A tri-amino acid spacer (KAA) was inserted between every 3-5 epitopes, to enhance peptide processing. Two parallel constructs were constructed, one with and one without ubiquitin (included to provide proteosomal targeting and further enhance peptide processing). pVAXMCMV-CTL (FIG. 2C) contains a 1.3 KB fragment coding for 55 CTL epitopes. pVAXMCMV-CTL-ubiquitin (FIG. 2B) contains a 1.5 KB fragment coding for 55 CTL epitopes, covalently linked (5') to a modified ubiquitin molecule.

Expression of Multivalent Polypeptide from a MCMV Construct

Recombinant proteins encoded by the synthetic genes have been produced in *E. coli* (FIG. 4). The expressed protein is larger, because the fusion tag attached to the protein is large. The fusion is detected (for example, in FIG. 4) with an anti-Histidine monoclonal antibody, which detects the fusion tag (poly-His) encoded by the vector.

Protein expression of Ubiquitin-CTL gene also has been confirmed in HeLa cells. A typical western blot analysis of HeLa Cells transfected with 1 μg of pVAX MCMV-CTL-ubiquitin is shown in FIG. 5. An anti-ubiquitin antibody was used for detection. These results indicate expression of an ubiquitinated protein of the correct predicted molecular weight as the synthetic CTL-ubiquitin gene. A band representing the normal cellular ubiquitin protein is also present on the blot.

Elispot Assays

To determine the biological relevance of epitopes used in the MCMV-CTL construct, epitopes contained in the construct were tested for recognition with PBMCs from HIV-1 infected individuals by doing Elispot assays. This example demonstrates that people infected with genetically different viruses could recognize epitopes included in the construct. Also since the individuals being tested are from different geographic locations, they are expected to have differences in their MHC molecules.

Epitope Testing (Elispot)

Chronically HIV-1-infected individuals infected with subtype B were selected from the HIV outpatient clinic at Johns Hopkins Hospital (Baltimore, Md.) for testing cellular immune responses to HIV-1 (Keating et al., *AIDS Research and Human Retroviruses* 18:1067-1079, 2002). Subject median age was 42 years, with a range of 25-58 years. Median viral load was 2,228 copies/ml with a range of less than 330 copies/ml to 37,716 copies/ml. Two of the subjects (Nos. 10 and 15) used in the analysis had viral loads of greater than 15,000 copies/ml, and were identified as non-responders to subtype B Gag peptides in the test of Keating et al. (*AIDS Research and Human Retroviruses* 18:1067-1079, 2002). The average number of years patients were HIV-1 infected was 9.46 years (range 5-17 years), and median CD4+ cell count was 534 cells/mm$^3$ with a range of 294-1009 cells/mm$^3$. These data represent a unique cohort of patients with strong immunological control as they have high CD4 values and have been HIV-1 infected for an average of nine years.

Peripheral blood was obtained by venipuncture and collected in heparin (Sigma, St. Louis, Mo.). PBMCs were isolated by Ficoll-Hypaque (Pharmacia-Amersham, Piscataway, N.J.) gradient centrifugation, frozen in fetal calf serum (FCS; Summit) with 10% DMSO (Sigma, St. Louis, Mo.) and stored at −140° C.

A 9×9 matrix (shown below) representing the 55 epitopes contained in the construct plus 23 control peptides from Flu, EBV and CMV was generated to study Elispot responses, using 1×10$^5$ cryopreserved PMBCs per well and 5 μg/ml peptide (below). Samples were run in duplicate, and the positive cutoff defined as wells that had 2× more spots than negative control wells and at least 10 spots. Responses identified in the matrix testing were confirmed with individual peptide testing. Elispot was carried out essentially as described in Keating et al., *AIDS Research and Human Retroviruses* 18:1067-1079, 2002.

TABLE 3

Peptide matrix

| | M1 | M2 | M3 | M4 | M5 | M6 | M7 | M8 | M9 |
|---|---|---|---|---|---|---|---|---|---|
| MA | 1-p17 | 2-p17 | 3-p17 | 4-p17 | 5-p17 | 6-p17 | 7-p24 | 8-p24 | 9-p24 |
| MB | 10-p24 | 11-p24 | 12-p24 | 13-p24 | 14-p24 | 15-p24 | 16-p24 | 17-p24 | 18-p24 |
| MC | 19-p24 | 20-p24 | 21-p24 | 22-p24 | 23-p24 | 24-p24 | 25-p24 | 26-p24 | 27-pol |
| MD | 28-pol | 29-pol | 30-pol | 31-pol | 32-pol | 33-pol | 34-pol | 35-pol | 36-pol |
| ME | 37-nef | 38-nef | 39-nef | 40-nef | 41-nef | 42-nef | 43-nef | 44-nef | 45-gp120 |
| MF | 46-gp120 | 47-gp120 | 48-gp120 | 49-gp41 | 50-gp41 | 51-vif | 52-vif | 53-vpr | 54-vpr |
| MG | 55-vpr | 56-flu | 57-flu | 58-EBV | 59-flu | 60-CMV | 61-flu | 62-EBV | 63-EBV |
| MH | 64-EBV | 65-EBV | 66-EBV | 67-Flu | 68-EBV | 69-CMV | 70-EBV | 71-EBV | 72-EBV |
| MI | 73-Flu | 74-Flu | 75-EBV | 76-EBV | 77-EBV | 78-CMV | | | |

TABLE 4

Peptides in the Matrix

| No. | Peptide list | Sequences | AA Position in SEQ ID NO:2 | HLA |
|---|---|---|---|---|
| 1 | p17-1 | KIRLRPGGK | 96-104 | A3, A3.1, B27 |
| 2 | p17-2 | RLRPGGKKKY | 98-107 | B42, Bw62 |
| 3 | p17-3 | WASRELERF | 108-116 | B35 |
| 4 | p17-4 | ELRSLYNTV | 77-85 | B8 |
| 5 | p17-5 | SLYNTVATL | 80-88 | A2 |
| 6 | p17-6 | TLYCVHQRI | 87-95 | A11 |
| 7 | p24-1 | ISPRTLNAW | 120-128 | B57 |
| 8 | p24-2 | TLNAWVKVV | 124-132 | A2 |
| 9 | p24-3 | KAFSPEVIPMF | 133-143 | B58 |
| 10 | p24-4 | IPMFSALSEGATPDQL (SEQ ID NO:15) | N/A | B44 |
| 11 | p24-5 | ATPQDLNTM | 150-158 | B7 |
| 12 | p24-6 | TSTLQEQIGW | 159-168 | B57 |
| 13 | p24-7 | NPPIPVGEIYKRWII (SEQ ID NO:16) | N/A | B8 |
| 14 | p24-8 | PPIPVGDIY | 173-181 | B35 |
| 15 | p24-9 | KRWIILGLNKIV | 182-193 | B27 |
| 16 | p24-10 | LGLNKIVRMYS | 187-197 | B62 |
| 17 | p24-11 | RMYSPTSI | 194-201 | B52 |
| 18 | p24-12 | FRDYVDRFYK | 202-211 | B18 |
| 19 | p24-13 | RDYVDRFYKTL | 203-213 | B44 |
| 20 | p24-14 | DYVDRFYKTL | 204-213 | A24 |

TABLE 4-continued

Peptides in the Matrix

| No. | Peptide list | Sequences | AA Position in SEQ ID NO:2 | HLA |
|---|---|---|---|---|
| 21 | p24-15 | YVDRFYKTL | 205-213 | B70 |
| 22 | p24-16 | DRFYKTLRA | 207-215 | B14 |
| 23 | p24-17 | VQNANPDCKTILKAL | 216-230 | B51 |
| 24 | p24-18 | NANPDCKTI | 218-226 | B8 |
| 25 | p24-19 | DCKTILKAL | 222-230 | B8 |
| 26 | p24-20 | ACQGVGGPGHK | 231-241 | A11 |
| 27 | POL-1 | ITLWQRPLV | 245-253 | A28 |
| 28 | POL-2 | TVLDVGDAY | 254-262 | B35 |
| 29 | POL-3 | VLDVGDAYFSV | 255-265 | A2, A0201 |
| 30 | POL-4 | WKGSPAIFQSSMT (SEQ ID NO:17) | N/A | B7, B35 |
| 31 | POL-5 | AIFQSSMTK (SEQ ID NO:18) | N/A | A11, A3 |
| 32 | POL-6 | ILKEPVHGV | 308-316 | A2, A0201 |
| 33 | POL-7 | QIYQEPFKNLKTG | 320-332 | A11 |
| 34 | POL-8 | EPIVGAETF | 333-341 | B35, B51 |
| 35 | POL-9 | AETFYVDGAAN | 338-348 | A28 |
| 36 | POL-10 | LLWKGEGAV | 358-366 | A2, A0201 |
| 37 | NEF-1 | VGFPVTPQVPLRPMT (SEQ ID NO:19) | N/A | A1, B8 |
| 38 | NEF-2 | FPVRPQVPL | 422-430 | B35 |
| 39 | NEF-3 | FPVRPQVPLR | 422-431 | B7 |
| 40 | NEF-4 | RPQVPLRPMTY | 425-435 | B35 |
| 41 | NEF-5 | QVPLRPMTYK | 427-436 | A3, A11, A2, B35 |
| 42 | NEF-6 | AVDLSHFLK | 438-446 | A11 |
| 43 | NEF-7 | FLKEKGGL | 444-451 | B8 |
| 44 | NEF-8 | GPGVRYPLTFGWCY | 452-465 | B57 |
| 45 | gp120-1 | TVYYGVPVWK | 478-487 | A3 |
| 46 | gp120-2 | VPVWKEATTT | 483-492 | B55, |
| 47 | gp120-3 | VPVWKEATTTL | 483-493 | B35 |
| 48 | gp120-4 | KTLPLCVTL | 469-477 | A2 |
| 49 | gp-41-1 | RAIEAQQHL | 494-502 | B51 |
| 50 | gp-41-1 | ERYLKDGGL | 503-511 | B14 |
| 51 | VIF-1 | HPKVSSEVHI | 380-389 | B0702 |
| 52 | VIF-2 | RIRTTWKSLVK (SEQ ID NO:20) | N/A | A0301 |
| 53 | VPRB-1 | AVRHFPRIWLHSL (SEQ ID NO:21) | N/A | B5701 |
| 54 | VPRNB-2 | AVRHFPRPWLHGL (SEQ ID NO:22) | N/A | B7301 |
| 55 | VPR-3 | AIIRILQQL | 408-416 | A0201 |
| 56 | Influenza A PB1 591-599 | VSDGGPNLY (SEQ ID NO:23) | N/A | A1 |
| 57 | Influenza A NP 44-52 | CTELKLSDY (SEQ ID NO:24) | N/A | A1 |
| 58 | EBV BMLF 259-267 | GLCTLVAML (SEQ ID NO:25) | N/A | A2 |
| 59 | Influenza A Matrix 1 58-66 | GILGFVFTL (SEQ ID NO:26) | N/A | A2 |
| 60 | HCMV Pp65 495-503 | NLVPMVATV (SEQ ID NO:27) | N/A | A2 |
| 61 | Influenza A NP 265-273 | ILRGSVAHK (SEQ ID NO:28) | N/A | A3 |
| 62 | EBV BMLF 259-267 | RVRAYTYSK (SEQ ID NO:29) | N/A | A3 |
| 63 | EBV EBNA3A 603-611 | RLRAEAQVK (SEQ ID NO:30) | N/A | A3 |
| 64 | EBV EBNA3B 416-424 | IVTDFSVIK (SEQ ID NO:31) | N/A | A11 |
| 65 | EBV BRLF1 134-143 | ATIGTAMYK (SEQ ID NO:32) | N/A | A11 |
| 66 | EBV BRLF1 28-37 | DYCNVLNKEF (SEQ ID NO:33) | N/A | A24 |
| 67 | Influenza A NP 91-99 | KTGGPIYKR (SEQ ID NO:34) | N/A | Aw68 |
| 68 | EBV EBNA3A 379-387 | RPPIFIRRL (SEQ ID NO:35) | N/A | B7 |
| 69 | HCMV Pp65 495-503 | TPRVTGGGAM (SEQ ID NO:36) | N/A | B7 |
| 70 | EBV EBNA3A 158-166 | QAKWRLQTL (SEQ ID NO:37) | N/A | B8 |
| 71 | EBV EBNA3A 325-333 | FLRGRAYGL (SEQ ID NO:38) | N/A | B8 |
| 72 | EBV BZLF1 190-197 | RAKFKQLL (SEQ ID NO:39) | N/A | B8 |
| 73 | Influenza A NP 380-388 | ELRSRYWAI (SEQ ID NO 40) | N/A | B8 |
| 74 | Influenza A NP 380-388 | SRYWAIRTR (SEQ ID NO:41) | N/A | B27 |
| 75 | EBV EBNA3C 258-266 | RRIYDLIEL (SEQ ID NO:42) | N/A | B27 |

TABLE 4-continued

Peptides in the Matrix

| No. | Peptide list | Sequences | AA Position in SEQ ID NO:2 | HLA |
|---|---|---|---|---|
| 76 | EBV EBNA3A 458-466 | YPLHEQHGM (SEQ ID NO:43) | N/A | B35 |
| 77 | EBV EBNA3C 281-290 | EENLLDFVRF (SEQ ID NO:44) | N/A | B44 |
| 78 | HCMV Pp65 495-503 | QEFFWDANDIYRIFA (SEQ ID NO:45) | N/A | B44 |

Results

Eleven individuals chronically infected with HIV-1 subtype B (the subtype found in the US) were tested. Preliminary testing of individuals form Ivory Coast, West Africa (subtype A/G viruses) was also conducted. These data indicate that the CTL epitopes contained in the construct are recognized by individuals infected with genetically distinct subtypes of HIV-1.

Figure 6:
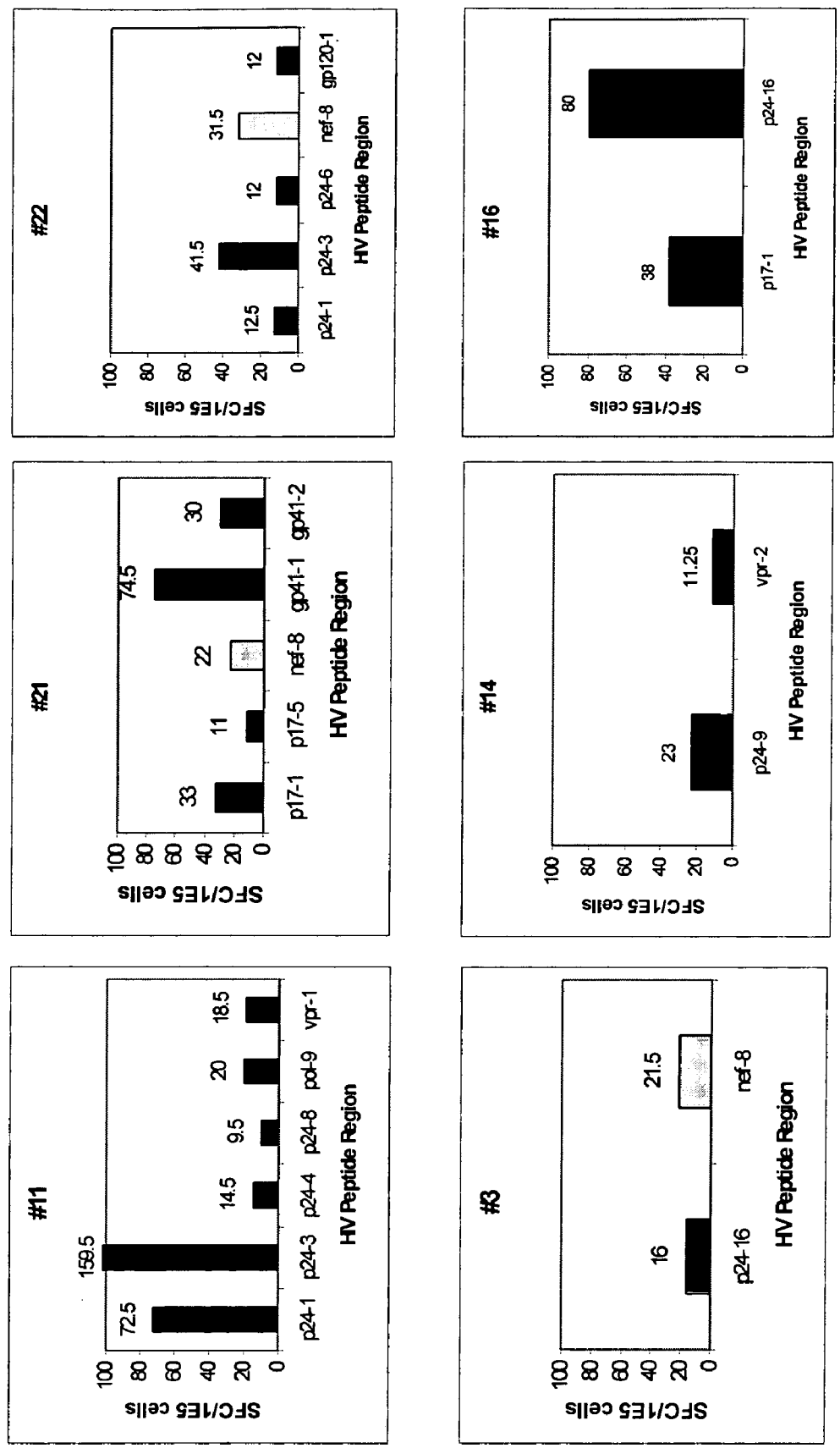
FIG. 6 is a series of bar graphs demonstrating breadth and magnitude of CTL responses observed to peptides contained in the MCMV-CTL construct with peripheral blood mononuclear cells (PBMCs) from individuals chronically infected with HIV-1 subtype B. The responses are reported as spot forming cells per 105 PBMCs.

The eleven patients had confirmed responses to multiple epitopes, in p17, p24, pol, vpr, gp41, gp120, and nef Representative bar graphs demonstrating breadth and magnitude of CTL responses generated from PBMCs of six of the eleven individuals chronically infected with subtype/clade B HIV-1 are shown in FIG. 6. These patient data are also summarized in the following table (which also includes data from the remaining five individuals), and indicate the viral load of the individual, their CD4 count, the known HLA type of the individual and the known HLA binding properties of the epitopes to which the individual responded.

TABLE 5

| Patient # | CD4 # | Viral load | Patient HLA | Response regions | Epitope HLA |
|---|---|---|---|---|---|
| 3 | 501 | 11,694 | A30, A33, B53, B14 | p24-6, Nef-8 | B57 |
| 7 | 349 | 6,177 | NA | Pol-6 | A2, A02201 |
| 10 | 700 | 37,716 | NA | Pol-9 | A28 |
| 11 | 924 | 1742 | A33, A68, B7, B57 | p24-1, p24-3, p24-4, VprB-1, Pol-9 | B57, B58, B44, B35, B5701 |
| 14 | 843 | <50 | A2, A30, B13, B27 | p24-9, VprNB-2 | B27, B7301 |
| 15 | 349 | 20,354 | NA | EBV Control only | B35 |
| 16 | 434 | 2714 | A3, A26, B49, B65 | p17-1, p24-16 | A3, B27, B14 |
| 18 | 493 | 5862 | A2, A29, B14, B72 | p17-5, p24-5, p24-16 | A2, B7, B14 |
| 19 | 822 | 1490 | NA | p24-1, p24-3 | B57, B58 |
| 21 | 567 | <29 | A3, A23, B35, B62 | P17-1, p17-5 Nef-8 gp41-1, gp41-2 | A3, B27, A2, B57, B14 |
| 22 | 1009 | <50 | A23, B57, B72 | p24-1, p24-3, p24-6, Nef-8, gp120-1 | B57, B58, B57, B57 |
| Neg Control | NA | Uninfected | NA | EBV Control only | B8 |

Ten of the eleven (10/11) patients (90.9%) responded to one or more peptides; 8/11 (72.7%) responded to two or more peptides in the multivalent construct. A summary of the peptides recognized from each gene region by the 11 chronically infected individuals (Subtype B) is provided in Table 6.

TABLE 6

| Gene Region | Peptides Recognized | Percentage |
|---|---|---|
| All peptides | 18/55 | 32.7 |
| Gag | 10/26 | 38.4 |

TABLE 6-continued

| Gene Region | Peptides Recognized | Percentage |
|---|---|---|
| Pol | 2/10 | 20 |
| Nef | 1/8 | 12.5 |
| Env | 3/6 | 50 |
| Vif | 0/2 | 0 |
| Vpr | 2/3 | 66 |

Figure 7:
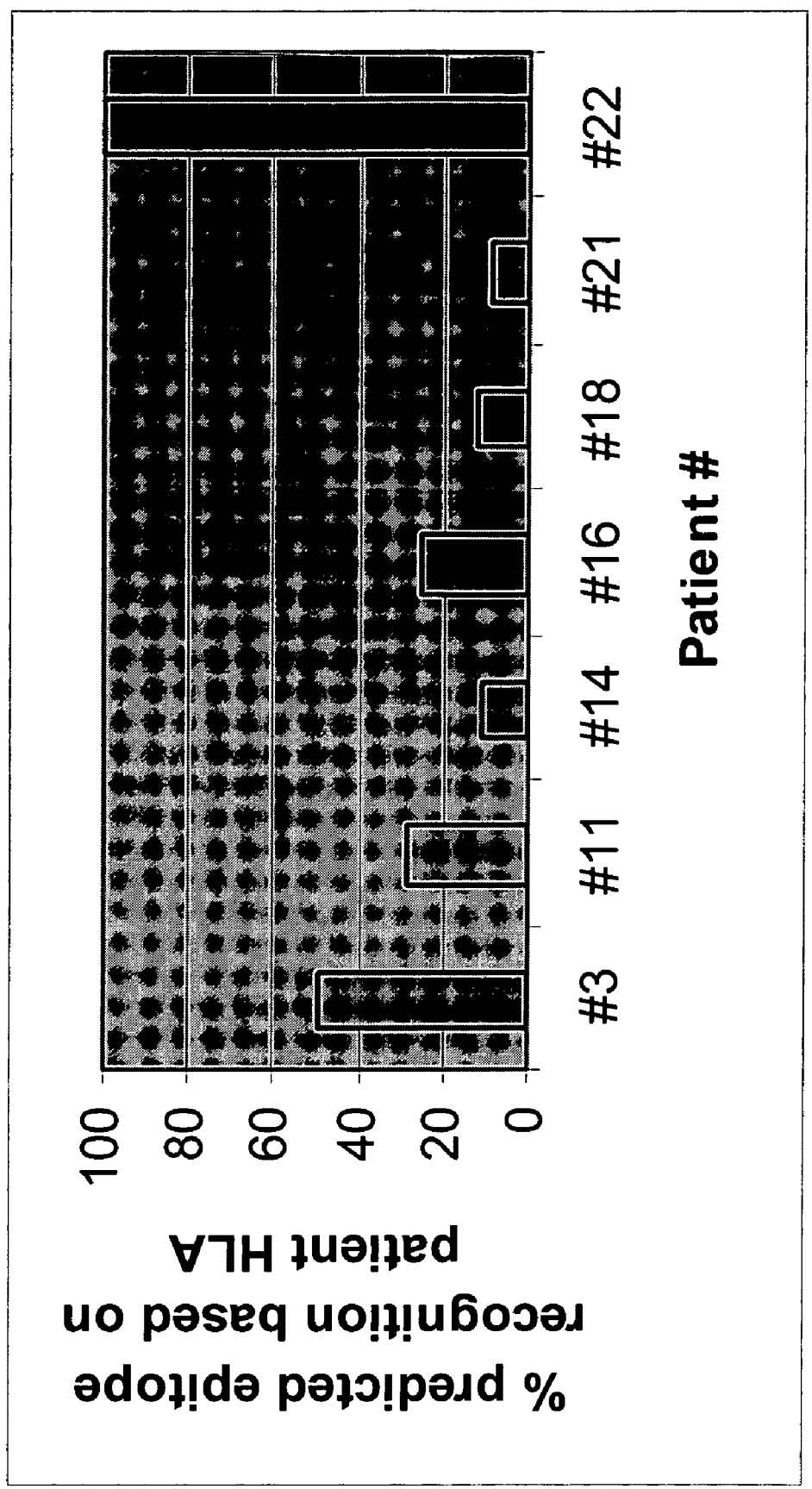
FIG. 7 is a bar graph demonstrating percentage predicted epitope recognition based on subject HLA type. The percentage of predicted epitopes that were targeted by patients' CD8+cells in the Elispot assay is shown.

Of the seven chronically HIV-infected study subjects who responded to HIV-1 individual peptides and had HLA typing made available, HLA specificities of the CTL epitopes were compared with the patient HLA types. All seven individuals responded to at least one of the predicted CTL epitopes according to the restricting HLA allele of that epitope. There was great variability as to whether patient cells could target those CTL epitopes predicted. FIG. 7 shows the percentage of predicted epitopes that were targeted by the patients' CD8+ cells in the Elispot assay. Patient number 21 responded to only one of the 12 peptides predicted to be targeted according to the patient's HLA type, whereas patient number 22 recognized all three of the peptides predicted to elicit Elispot responses. All of the 7 subject studies were capable of targeting epitopes outside of their respective HLA type. For example, patient number 3 who had been characterized for A30, A33, B53, and B14 HLA type, only recognized p24 peptide sequence TSTLQEQIGW, which is a B57 HLA restricted CTL epitope. Of the 7 peptides targeted by patient number 11, four were epitopes restricted to mismatched HLA haplotype. All five of the HLA restricted epitopes targeted by patient number 21 were disparate for that individual's HLA type.

Preliminary testing of individuals infected with other subtypes of virus (A from Kenya, C from India and A/E from Thailand) is underway.

Additional testing was carried out using PBMCs from HIV-1 positive blood donors from Ivory Coast. The testing was done as described for the subtype B individuals, in that the same peptide pool matrix was tested as describe above. The four Ivorian samples tested were from "healthy" blood donors and thus were presumed to be incident HIV-1 infections. Due to the high prevalence of recombinant subtype A/G viruses in this region, it is presumed these individuals were infected with A/G viruses. The four individuals had broad responses based on the results of the peptide matrix screen.

Individual 1 had predicted responses from the matrix to 46 peptides contained in MCMV. The gene regions represented by these peptides included p24, pol, nef, gp120, vpr, and vif. Individual 2 had predicted responses to 15 peptides (in pol, nef, gp41, and vif). Individual 3 had predicted responses to 10 peptides (in p24, nef, vpr, and gp120). Individual 4 had predicted responses to 47 epitopes contained in the following HIV-1 gene regions: p17, p24, pol, nef, gp120, gp41, vpr, and vif.

Overall, good CTL responses were observed to chosen epitopes (in gag, pol, env, nef, vpr, and vif) in subtype B infected individuals from the United States and presumed subtype A/G infected individuals from Ivory Coast.

Mouse Studies

Transgenic HLA mice studies can be carried out to detect immunologic responses induced by each construct (with and without ubiquitin). A comparison of the with and without ubiquitin constructs will enable characterization of the effects of ubiquitin on epitope processing and immunogenicity.

One HIV-1 epitope was included in the MCMV-CTL construct (located in the middle of the construct) which has previously been shown to be recognized by mice expressing MHC class I H-2D. The inclusion of this epitope allows limited immunogenicity studies with any mouse strain that expresses the H-2D allele. In addition, transgenic mice that express human MHC molecules (such as the C57BL/6-TgN (HLA-A2.1) strain) can be used to further look at all of the epitopes in the construct that are A2.1 restricted. By way of example, 1-3 doses of the DNA can be tested, likely 2-5 µg of DNA at a time, applying the DNA interdermally using a gene gun.

Mice will be sacrificed and splenocytes will be harvested 7-10 days after the last injection. The splenocytes will then be used in Elispot assays to determine if the mice recognize specific peptides contained within the construct. Parallel studies can be done with the construct with and without ubiquitin to demonstrate that the ubiquitin fusion increases CTL responses (breadth, A2.1 restricted epitopes, and magnitude).

Primate Studies

Due to the inclusion of the Mamu-A¤01 restricted epitope, monkeys that have this HLA can be used to study the effects of adding the ubiquitin tag, and to characterize the resultant changes in the magnitude of the immunogenic responses.

B-Cell/T-Helper Cell/Lysosome Constructs

The B-cell (Table 7) and T-helper (Table 8) epitopes were chosen by literature searches and information and software contained in the Los Alamos HIV Molecular Immunology database.

TABLE 7

| B epitopes | Clade | Region | Sequence | AA Position in SEQ ID NO:8 | Source |
|---|---|---|---|---|---|
| Tat | A | 21-40 | PCNKCYCKKCCYHCQVCFLN | 79-98 | Boykins et al. 2001 |
| Tat | B | 21-40 | ACTNCYCKKCCFHCQVCFTT | 2-21 | peptides 21: |
| Tat | C | 21-40 | ACNTCYCKKCSYHCLVCFQT | 146-165 | 1839/database |
| Tat | D | 21-40 | PCNKCYCKKCCYHCQVCFIT (SEQ ID NO:46) | N/A | |
| Tat | A/E | 21-40 | ACSKCYCKKCCWHCQLCFLK (SEQ ID NO:47) | N/A | |
| Tat | F | 21-40 | PCTKCYCKRCCFHCQWCFIT (SEQ ID NO:48) | N/A | |
| Tat | A/G | 21-40 | ACSKCYCHICCWHCQLCFLN (SEQ ID NO:49) | N/A | |
| Tat | A | 53-68 | KQRRGTPQSNKDHQNP | 102-117 | |
| Tat | B | 53-68 | RQRRAPQDSQTHQVS | 26-41 | |
| Tat | C | 53-68 | RQRRSAPPSSEDHQNL | 170-185 | |
| Tat | D | 53-68 | RQRRRPPQGGQAHQDP (SEQ ID NO:50) | N/A | |
| Tat | A/E | 53-68 | KHRRGTPQSSKDHQNP (SEQ ID NO:51) | N/A | |
| Tat | A/G | 53-68 | RRRRGTPQSRQDHQNP (SEQ ID NO:52) | N/A | |
| Tat | F | 53-68 | RQRHRTPQSSQIHQDP (SEQ ID NO:53) | N/A | |
| gp120 | | | HERSYMFSDLENRCI | 214-228 | 2001 Vaccine meeting #295 Menendez et al. |
| gp41 | A | 2F5-4E10 | NEQDLLALDKWANLWNWFDIS | 122-142 | Parker et al. J Virol. |
| gp41 | B | 2F5-4E10 | NEQELLELDKWASLWNWFDIT | 189-209 | 2001 75: 10906 |
| gp41 | C | 2F5-4E10 | NEKDLLALDKWQNLWSWFDIT | 229-249 | Non-B subtype |
| gp41 | D | 2F5-4E10 | NEKELLELDKWASLWNWFSIT (SEQ ID NO:54) | N/A | peptide sequences were determined |
| gp41 | F | 2F5-4E10 | NEQELLALDKWASLWNWFDIS (SEQ ID NO:55) | N/A | using the Los Alamos HIV sequence |

TABLE 7-continued

| B epitopes | Clade | Region | Sequence | AA Position in SEQ ID NO:8 | Source |
|---|---|---|---|---|---|
| gp41 | G | 2F5-4E10 | NEQDLLALDKWASLWTWFSIT (SEQ ID NO:56) | N/A | Database subtype consensus sequence data. |
| gp41 | | N1 | SGIVQQQNNLLRAIEAQQHLLQ LTVWGIKQLQARIL (SEQ ID NO:57) | N/A | Rosny et a. J Virol 2001 75: 8859-8863 |
| gp41 | | C1 | WMEWDREINNYTSLIHSLIEES QNQQEKNEQELL | 297-330 | |
| human CCR5 | | ECL1 89-102 | YAAAQWDFGNTMCQL (SEQ ID NO:58) | N/A | Barassi et al. AIDS Vaccine 2001 |
| human CCR5 | | ECL2 178-197 | CSSHFPYSQYQFWKNFQTLK (SEQ ID NO:59) | N/A | abstract #112/ Philadelphia, PA Sep. 5-8, 2001 |

TABLE 8

| T-helper | Region | Sequence | AA Position in SEQ ID NO:8 | Source |
|---|---|---|---|---|
| p24 | 111-132 | LQEQIGWMTNNPPIPVGEIYKR | 386-407 | Wilson et al. J Virol 2001 75: 4195 and Cosimi and Rosenberg, Los Alamos HIV Molecular Immunology Database, 2000 |
| p24 | 131-152 | KRWIILGLNKIVRMYSPTSILD | 406-427 | Wilson et al., J. Virol 2001 75: 4195 |
| p24 | 146-160 | SPVSILDIRQGPKEP (SEQ ID NO:60) | N/A | Cosimi and Rosenberg, Los Alamos HIV Molecular Immunology Database, 2000 |
| p24 | 1-22 | PIVQNIQGQMVHQAISPRTLNA | 360-381 | |
| p24 | 156-170 | GPKEPFRDYVDRFYK | 431-445 | |
| p24 | 31-52 | AFSPEVIPMFSALSEGATPQDL | 338-359 | |
| pol | 36-52 | EICTEMEKEGKISKIGP | 446-462 | |
| pol (rt) | 303-317 | FRKYTAFTIPSINNE | 467-481 | Wilson et al., J. Virol 2001 75: 4195 |
| pol (rt) | 335-349 | SPAIFQSSMTKILEP | 482-496 | |
| pol (rt) | 596-610 | WEFVNTPPLVKLWYQ | 497-511 | |
| pol (int) | 915-929 | KTAVQMAVFIHNFKR | 512-526 | |
| pol (int) | 956-970 | QKQITKIQNFRVYYR | 527-541 | |
| vpr | 66-80 | QLLFIHFRIGCRHSR (SEQ ID NO:61) | N/A | Cosimi and Rosenberg, Los Alamos HIV Molecular Immunology Database, 2000 |
| rev | 9-23 | DEELIRTVRLIKLLY (SEQ ID NO:62) | N/A | |
| rev | 41-56 | RRRRWRERQRQIHSIS (SEQ ID NO:63) | N/A | |
| env | 476-490 | DMRDNWRSELYKYKV | 596-610 | |
| env | 562-576 | QQHLLQLTVWGIKQL | 611-625 | |
| env | 667-681 | ASLWNWFDITNWLWY | 626-640 | |
| env | 682-696 | IKIFIMIVGGLIGLR | 641-655 | |
| env | 827-841 | HIPRRIRQGLERALL (SEQ ID NO:64) | N/A | |

Construction of a MCMV construct containing these B-cell and T-helper epitopes was carried out essentially similarly to the procedures used to generate the MCMV-CTL construct. Representative sequences of MCMV-AB/Th construct are shown in SEQ ID NOs: 7 and 9; the encoded multivalent antigen polypeptides are shown in SEQ ID NOs: 8 and 10. A tri-amino acid spacer (GPG) was inserted between each of the Ab epitopes and between every 3-5 T-helper epitopes, to provide additional flexibility in the molecule, and to enhance peptide presentation. In addition, the LIMP-II lysosomal targeting sequence was included at the C-terminus in one construct (SEQ ID NOs: 7 and 8), to enhance processing of the epitopes.

Synthetic peptides of the T-helper epitopes have been synthesized, using standard peptide synthesis protocols, for use in lymphocyte proliferation assays.

Targeting to Lysosome

Detection of targeting of a MCMV-AB/Th polypeptide to the lysosome can be accomplished using confocal microscopy. By way of example, HeLa cells can be transfected with the pVax-1 MCMV constructs (with and without and ubiquitin) followed by staining protocols to detect the lysosome (detection of LAMP-1 using a LAMP-1-specific antibody) and the expressed MCMV protein (for example, using polyclonal antibody generated by injection of the recombinant MCMV protein into mice). A detailed protocol for the detection of lysosomal targeting is found in Rodriguez et al., *J. Virology* 75:10421-10430, 2001.

Confirmation of Immunogenicity of Ab and T-Helper Construct(s)

In order to confirm the immunogenicity of the epitopes in a MCMV-AB/Th construct, T-helper assays (Lymphocyte proliferation assays) can be performed using PBMCs from HIV-1 infected individuals, using methods basically as described in Wilson et al. *J. Virology* 75:4195-4207, 2001.

For the antibody epitopes, sera/plasma from infected individuals can be used to test for the presence of antibodies that would react with the protein encoded by this construct. Additionally, mouse or monkey immunization studies with either the DNA construct or purified recombinant MCMV-AB/Th protein (practically any strain of mouse or primate routinely available) can be preformed to ascertain the production of antibodies. Animals would be injected with 1-3 doses of DNA (2-5 µg DNA for mice and 1-2 mg DNA for rhesus macaques) or purified recombinant protein (20-50 µg for mice or 50-500 µg for monkeys). Prior to the first injection and 1-2 weeks following each injection, blood will be drawn and tested for the presence of antibody specific to the MCMV-AB/Th epitopes by ELISA.

Other methods for testing the immunogenicity of Ab and T-helper epitopes will be known to those of ordinary skill in the art.

Determination of the Optimal Time Frame for Vaccination with the Recombinant Protein as an Immunologic "Boost"

Recombinant protein produced from the MCMV constructs described herein can be utilized in conjunction with the DNA immunogen(s), or other currently available DNA vaccines, as an immunological "boost".

Following the initial animal injections with the DNA construct(s) immune responses will be monitored (for instance, using CTLs, Elispot assays, T-helper/lymphocyte proliferation assays, and/or ELISA assays) to determine the peak of the immune response for each arm of the immune system (T-Cell and B-cell). Based on the observed responses, a series of boost injections of a MCMV polypeptide can be initiated. By studying the responses, the time frame to generate the maximum response from memory T or B-cells can be optimized. Systems for optimizing the boost effect will be known to those of ordinary skill in the art.

Clinical Trials

Following the production of the vaccine materials, Phase I safety trials can be performed in populations at risk for HIV. In the United States, target populations would include, for example, gay male cohorts or IV Drug using cohorts. In countries other than the United States, potential populations would include, for example, prenatal cohorts, IV drug use cohorts and prostitutes.

It will be apparent that the precise details of the constructs, compositions, and methods described herein may be varied or modified without departing from the spirit of the described invention. We claim all such modifications and variations that fall within the scope and spirit of the claims below.

We claim:

1. An isolated recombinant polyepitope polypeptide comprising an amino acid sequence selected from the group consisting of sequences recited in SEQ ID NOs: 2, 4, 5, 6, 8, 10, and combinations of two or more thereof.

2. An isolated nucleic acid molecule encoding a polypeptide of claim 1.

3. The isolated nucleic acid molecule of claim 2, wherein the nucleic acid molecule comprises a sequence selected from the group consisting of SEQ ID NOs: 1, 3, 7, and 9.

4. A vector comprising at least one nucleic acid molecule of claim 3.

5. A host cell transformed with a vector of claim 4.

6. A composition comprising at least one polypeptide of claim 1.

7. The composition of claim 6, further comprising at least one component selected from the group consisting of pharmaceutically acceptable carriers, adjuvants, and combinations of two or more thereof.

8. A method of eliciting an immune response against an antigenic epitope in a subject, comprising introducing into the subject the composition of claim 6.

9. A method for enhancing an immune response in a subject, comprising administering to the subject the composition of claim 6 and an adjuvant.

10. A composition comprising at least one nucleic acid molecule of claim 2.

* * * * *

UNITED STATES PATENT AND TRADEMARK OFFICE
CERTIFICATE OF CORRECTION

PATENT NO. : 7,425,611 B2
APPLICATION NO. : 10/550651
DATED : September 16, 2008
INVENTOR(S) : Lal and Owen It is certified that error appears in the above-identified patent and that said Letters Patent is hereby corrected as shown below:

In column 1, line 9, "2192)" should read --21(2)--.

In column 1, lines 10-11, "60/458,990" should read --60/458,880--.

In column 3, line 1, "132" should read --β2--.

In column 6, lines 1-2, "of representative" should read --of a representative--.

In column 9, line 38, "between to distinct" should read --between two distinct--.

In column 14, line 57, "cells'" should read --cell's--.

In column 18, line 55, "HV-1 genome" should read --HIV-1 genome--.

In column 33, line 25, "nef Representative" should read --nef. Representative--.

In column 36, line 25, "A˚01" should read --A*01--.

Signed and Sealed this

Fifth Day of May, 2009

JOHN DOLL
*Acting Director of the United States Patent and Trademark Office*

SEQUENCE LISTING

```
<160> NUMBER OF SEQ ID NOS: 64

<210> SEQ ID NO 1
<211> LENGTH: 1557
<212> TYPE: DNA
<213> ORGANISM: Artificial Sequence
<220> FEATURE:
<223> OTHER INFORMATION: Construct encoding polyepitope polypeptide.
<220> FEATURE:
<221> NAME/KEY: CDS
<222> LOCATION: (12)..(1547)
<223> OTHER INFORMATION: Sequence encoding MCMVCTL-ubiquitin
      polyepitope polypeptide.

<400> SEQUENCE: 1
ctaggctagc t atg cag atc ttc gtg aaa acc ctt acc ggc aag acc atc      50
             Met Gln Ile Phe Val Lys Thr Leu Thr Gly Lys Thr Ile
               1               5                  10 acc ctt gag gtg gag ccc agt gac acc atc gaa aat gtg aag gcc aag       98
Thr Leu Glu Val Glu Pro Ser Asp Thr Ile Glu Asn Val Lys Ala Lys
       15                  20                  25 atc cag gat aag gaa ggc att ccc ccc gac cag cag agg ctc atc ttt      146
Ile Gln Asp Lys Glu Gly Ile Pro Pro Asp Gln Gln Arg Leu Ile Phe
 30                  35                  40                  45 gca ggc aag cag ctg gaa gat ggc cgt act ctt tct gac tac aac atc      194
Ala Gly Lys Gln Leu Glu Asp Gly Arg Thr Leu Ser Asp Tyr Asn Ile
                 50                  55                  60 cag aag gag tcg acc ctg cac ctg gtc ctg cgt ctg aga ggt gct gag      242
Gln Lys Glu Ser Thr Leu His Leu Val Leu Arg Leu Arg Gly Ala Glu
             65                  70                  75 ctc cgc tcc ctc tac aac acc gtg gcc acc ctc tac tgc gtg cac cag      290
Leu Arg Ser Leu Tyr Asn Thr Val Ala Thr Leu Tyr Cys Val His Gln
         80                  85                  90 cgc atc aag atc cgc ctg cgc ccc ggc ggc aag aag aag tac tgg gcc      338
Arg Ile Lys Ile Arg Leu Arg Pro Gly Gly Lys Lys Lys Tyr Trp Ala
     95                  100                 105
```

```
                                                         -continued agc cgc gag ctg gag cgc ttc aag gcc gcc atc agc ccc cgc acc ctg      386
Ser Arg Glu Leu Glu Arg Phe Lys Ala Ala Ile Ser Pro Arg Thr Leu
110             115                 120                 125 aac gcc tgg gtg aag gtg gtg aag gcc ttc agc ccc gag gtg atc ccc      434
Asn Ala Trp Val Lys Val Val Lys Ala Phe Ser Pro Glu Val Ile Pro
            130                 135                 140 atg ttc agc gcc ctg agc gag ggc gcc acc ccc cag gac ctg aac acc      482
Met Phe Ser Ala Leu Ser Glu Gly Ala Thr Pro Gln Asp Leu Asn Thr
        145                 150                 155 atg acc agc acc ctg cag gag cag atc ggc tgg aag gcc gcc aac ccc      530
Met Thr Ser Thr Leu Gln Glu Gln Ile Gly Trp Lys Ala Ala Asn Pro
    160                 165                 170 ccc atc ccc gtg ggc gac atc tac aag cgc tgg atc atc ctg ggc ctg      578
Pro Ile Pro Val Gly Asp Ile Tyr Lys Arg Trp Ile Ile Leu Gly Leu
175                 180                 185 aac aag atc gtg cgc atg tac agc ccc acc agc atc ttc cgc gac tac      626
Asn Lys Ile Val Arg Met Tyr Ser Pro Thr Ser Ile Phe Arg Asp Tyr
190                 195                 200                 205 gtg gac cgc ttc tac aag acc ctg cgc gcc gtg cag aac gcc aac ccc      674
Val Asp Arg Phe Tyr Lys Thr Leu Arg Ala Val Gln Asn Ala Asn Pro
            210                 215                 220 gac tgc aag acc atc ctg aag gcc ctg gcc tgc cag ggc gtg ggc ggc      722
Asp Cys Lys Thr Ile Leu Lys Ala Leu Ala Cys Gln Gly Val Gly Gly
        225                 230                 235 ccc ggc cac aag aag gcc gcc atc acc ctg tgg cag cgc ccc ctg gtg      770
Pro Gly His Lys Lys Ala Ala Ile Thr Leu Trp Gln Arg Pro Leu Val
    240                 245                 250 acc gtg ctg gac gtg ggc gac gcc tac ttc agc gtg tgg aag ggc agc      818
Thr Val Leu Asp Val Gly Asp Ala Tyr Phe Ser Val Trp Lys Gly Ser
255                 260                 265 ccc gcc atc ttc cag agc aag ctt cgc ggc ccc ggc cgc gcc ttc gtg      866
Pro Ala Ile Phe Gln Ser Lys Leu Arg Gly Pro Gly Arg Ala Phe Val
270                 275                 280                 285 acc atc aag gcc gcc gcc tgc acc ccc tac gac atc aac cag atg ctg      914
Thr Ile Lys Ala Ala Ala Cys Thr Pro Tyr Asp Ile Asn Gln Met Leu
            290                 295                 300 ggt acc agc atg acc aag atc ctg aag gag ccc gtg cac ggc gtg aag      962
Gly Thr Ser Met Thr Lys Ile Leu Lys Glu Pro Val His Gly Val Lys
        305                 310                 315 gcc gcc cag atc tac cag gag ccc ttc aag aac ctg aag acc ggc gag     1010
Ala Ala Gln Ile Tyr Gln Glu Pro Phe Lys Asn Leu Lys Thr Gly Glu
    320                 325                 330 ccc atc gtg ggc gcc gag acc ttc tac gtg gac ggc gcc gcc aac gtg     1058
Pro Ile Val Gly Ala Glu Thr Phe Tyr Val Asp Gly Ala Ala Asn Val
335                 340                 345 atc tac cag tac atg gac gac ctg ctg ctg tgg aag ggc gag ggc gcc     1106
Ile Tyr Gln Tyr Met Asp Asp Leu Leu Leu Trp Lys Gly Glu Gly Ala
350                 355                 360                 365 gtg aag gcc gcc cgc atc cgc acc tgg aag agc ctg gtg aag cac ccc     1154
Val Lys Ala Ala Arg Ile Arg Thr Trp Lys Ser Leu Val Lys His Pro
            370                 375                 380 aag gtg agc agc gag gtg cac atc gcc gtg cgc cac ttc ccc cgc atc     1202
Lys Val Ser Ser Glu Val His Ile Ala Val Arg His Phe Pro Arg Ile
        385                 390                 395 tgg gcc gtg cgc cac ttc ccc cgc ccc tgg gcc atc atc cgc atc ctg     1250
Trp Ala Val Arg His Phe Pro Arg Pro Trp Ala Ile Ile Arg Ile Leu
    400                 405                 410 cag cag ctg aag gcc gcc gtg ggc ttc ccc gtg cgc ccc cag gtg ccc     1298
Gln Gln Leu Lys Ala Ala Val Gly Phe Pro Val Arg Pro Gln Val Pro
```

-continued

```
       415                 420                 425
ctg cgc ccc atg acc tac aag ggc gcc gtg gac ctg agc cac ttc ctg    1346
Leu Arg Pro Met Thr Tyr Lys Gly Ala Val Asp Leu Ser His Phe Leu
430                 435                 440                 445 aag gag aag ggc ggc ctg ggc ccc ggc gtg cgc tac ccc ctg acc ttc    1394
Lys Glu Lys Gly Gly Leu Gly Pro Gly Val Arg Tyr Pro Leu Thr Phe
            450                 455                 460 ggc tgg tgc tac aag gcc gcc aag acc ctg ccc ctg tgc gtg acc ctg    1442
Gly Trp Cys Tyr Lys Ala Ala Lys Thr Leu Pro Leu Cys Val Thr Leu
                465                 470                 475 acc gtg tac tac ggc gtg ccc gtg tgg aag gag gcc acc acc acc ctg    1490
Thr Val Tyr Tyr Gly Val Pro Val Trp Lys Glu Ala Thr Thr Thr Leu
            480                 485                 490 cgc gcc atc gag gcc cag cag cac ctg gag cgc tac ctg aag gac ggc    1538
Arg Ala Ile Glu Ala Gln Gln His Leu Glu Arg Tyr Leu Lys Asp Gly
        495                 500                 505 ggc ctg tag ctcgagtagc                                             1557
Gly Leu
510
```

<210> SEQ ID NO 2
<211> LENGTH: 511
<212> TYPE: PRT
<213> ORGANISM: Artificial Sequence
<220> FEATURE:
<223> OTHER INFORMATION: Construct encoding polyepitope polypeptide.

<400> SEQUENCE: 2

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Glu Leu Arg Ser
65                  70                  75                  80

Leu Tyr Asn Thr Val Ala Thr Leu Tyr Cys Val His Gln Arg Ile Lys
                85                  90                  95

Ile Arg Leu Arg Pro Gly Gly Lys Lys Tyr Trp Ala Ser Arg Glu
            100                 105                 110

Leu Glu Arg Phe Lys Ala Ala Ile Ser Pro Arg Thr Leu Asn Ala Trp
        115                 120                 125

Val Lys Val Lys Ala Phe Ser Pro Glu Val Ile Pro Met Phe Ser
    130                 135                 140

Ala Leu Ser Glu Gly Ala Thr Pro Gln Asp Leu Asn Thr Met Thr Ser
145                 150                 155                 160

Thr Leu Gln Glu Gln Ile Gly Trp Lys Ala Ala Asn Pro Pro Ile Pro
                165                 170                 175

Val Gly Asp Ile Tyr Lys Arg Trp Ile Ile Leu Gly Leu Asn Lys Ile
            180                 185                 190

Val Arg Met Tyr Ser Pro Thr Ser Ile Phe Arg Asp Tyr Val Asp Arg
        195                 200                 205

Phe Tyr Lys Thr Leu Arg Ala Val Gln Asn Ala Asn Pro Asp Cys Lys
    210                 215                 220

Thr Ile Leu Lys Ala Leu Ala Cys Gln Gly Val Gly Gly Pro Gly His
```

```
                225                 230                 235                 240
Lys Lys Ala Ala Ile Thr Leu Trp Gln Arg Pro Leu Val Thr Val Leu
                245                 250                 255

Asp Val Gly Asp Ala Tyr Phe Ser Val Trp Lys Gly Ser Pro Ala Ile
            260                 265                 270

Phe Gln Ser Lys Leu Arg Gly Pro Gly Arg Ala Phe Val Thr Ile Lys
        275                 280                 285

Ala Ala Ala Cys Thr Pro Tyr Asp Ile Asn Gln Met Leu Gly Thr Ser
290                 295                 300

Met Thr Lys Ile Leu Lys Glu Pro Val His Gly Val Lys Ala Ala Gln
305                 310                 315                 320

Ile Tyr Gln Glu Pro Phe Lys Asn Leu Lys Thr Gly Glu Pro Ile Val
                325                 330                 335

Gly Ala Glu Thr Phe Tyr Val Asp Gly Ala Ala Asn Val Ile Tyr Gln
            340                 345                 350

Tyr Met Asp Asp Leu Leu Leu Trp Lys Gly Glu Gly Ala Val Lys Ala
        355                 360                 365

Ala Arg Ile Arg Thr Trp Lys Ser Leu Val Lys His Pro Lys Val Ser
370                 375                 380

Ser Glu Val His Ile Ala Val Arg His Phe Pro Arg Ile Trp Ala Val
385                 390                 395                 400

Arg His Phe Pro Arg Pro Trp Ala Ile Ile Arg Ile Leu Gln Gln Leu
                405                 410                 415

Lys Ala Ala Val Gly Phe Pro Val Arg Pro Gln Val Pro Leu Arg Pro
            420                 425                 430

Met Thr Tyr Lys Gly Ala Val Asp Leu Ser His Phe Leu Lys Glu Lys
        435                 440                 445

Gly Gly Leu Gly Pro Gly Val Arg Tyr Pro Leu Thr Phe Gly Trp Cys
450                 455                 460

Tyr Lys Ala Ala Lys Thr Leu Pro Leu Cys Val Thr Leu Thr Val Tyr
465                 470                 475                 480

Tyr Gly Val Pro Val Trp Lys Glu Ala Thr Thr Thr Leu Arg Ala Ile
                485                 490                 495

Glu Ala Gln Gln His Leu Glu Arg Tyr Leu Lys Asp Gly Gly Leu
            500                 505                 510

<210> SEQ ID NO 3
<211> LENGTH: 1323
<212> TYPE: DNA
<213> ORGANISM: Artificial Sequence
<220> FEATURE:
<223> OTHER INFORMATION: Construct encoding polyepitope polypeptide.
<220> FEATURE:
<221> NAME/KEY: CDS
<222> LOCATION: (7)..(1317)
<223> OTHER INFORMATION: Sequence encoding MCMVCTL (no ubiquitin)
      polyepitope polypeptide.

<400> SEQUENCE: 3 gctagc atg gag ctc cgc tcc ctc tac aac acc gtg gcc acc ctc tac        48
       Met Glu Leu Arg Ser Leu Tyr Asn Thr Val Ala Thr Leu Tyr
       1               5                   10 tgc gtg cac cag cgc atc aag atc cgc ctg cgc ccc ggc ggc aag aag        96
Cys Val His Gln Arg Ile Lys Ile Arg Leu Arg Pro Gly Gly Lys Lys
15                  20                  25                  30 aag tac tgg gcc agc cgc gag ctg gag cgc ttc aag gcc gcc atc agc       144
Lys Tyr Trp Ala Ser Arg Glu Leu Glu Arg Phe Lys Ala Ala Ile Ser
                35                  40                  45
```

```
ccc cgc acc ctg aac gcc tgg gtg aag gtg gtg aag gcc ttc agc ccc      192
Pro Arg Thr Leu Asn Ala Trp Val Lys Val Val Lys Ala Phe Ser Pro
            50                  55                  60 gag gtg atc ccc atg ttc agc gcc ctg agc gag ggc gcc acc ccc cag      240
Glu Val Ile Pro Met Phe Ser Ala Leu Ser Glu Gly Ala Thr Pro Gln
 65                  70                  75 gac ctg aac acc atg acc agc acc ctg cag gag cag atc ggc tgg aag      288
Asp Leu Asn Thr Met Thr Ser Thr Leu Gln Glu Gln Ile Gly Trp Lys
     80                  85                  90 gcc gcc aac ccc ccc atc ccc gtg ggc gac atc tac aag cgc tgg atc      336
Ala Ala Asn Pro Pro Ile Pro Val Gly Asp Ile Tyr Lys Arg Trp Ile
 95             100                 105                 110 atc ctg ggc ctg aac aag atc gtg cgc atg tac agc ccc acc agc atc      384
Ile Leu Gly Leu Asn Lys Ile Val Arg Met Tyr Ser Pro Thr Ser Ile
                115                 120                 125 ttc cgc gac tac gtg gac cgc ttc tac aag acc ctg cgc gcc gtg cag      432
Phe Arg Asp Tyr Val Asp Arg Phe Tyr Lys Thr Leu Arg Ala Val Gln
            130                 135                 140 aac gcc aac ccc gac tgc aag acc atc ctg aag gcc ctg gcc tgc cag      480
Asn Ala Asn Pro Asp Cys Lys Thr Ile Leu Lys Ala Leu Ala Cys Gln
                145                 150                 155 ggc gtg ggc ggc ccc ggc cac aag aag gcc gcc atc acc ctg tgg cag      528
Gly Val Gly Gly Pro Gly His Lys Lys Ala Ala Ile Thr Leu Trp Gln
160                 165                 170 cgc ccc ctg gtg acc gtg ctg gac gtg ggc gac gcc tac ttc agc gtg      576
Arg Pro Leu Val Thr Val Leu Asp Val Gly Asp Ala Tyr Phe Ser Val
175                 180                 185                 190 tgg aag ggc agc ccc gcc atc ttc cag agc aag ctt cgc ggc ccc ggc      624
Trp Lys Gly Ser Pro Ala Ile Phe Gln Ser Lys Leu Arg Gly Pro Gly
                195                 200                 205 cgc gcc ttc gtg acc atc aag gcc gcc gcc tgc acc ccc tac gac atc      672
Arg Ala Phe Val Thr Ile Lys Ala Ala Ala Cys Thr Pro Tyr Asp Ile
            210                 215                 220 aac cag atg ctg ggt acc agc atg acc aag atc ctg aag gag ccc gtg      720
Asn Gln Met Leu Gly Thr Ser Met Thr Lys Ile Leu Lys Glu Pro Val
                225                 230                 235 cac ggc gtg aag gcc gcc cag atc tac cag gag ccc ttc aag aac ctg      768
His Gly Val Lys Ala Ala Gln Ile Tyr Gln Glu Pro Phe Lys Asn Leu
240                 245                 250 aag acc ggc gag ccc atc gtg ggc gcc gag acc ttc tac gtg gac ggc      816
Lys Thr Gly Glu Pro Ile Val Gly Ala Glu Thr Phe Tyr Val Asp Gly
255                 260                 265                 270 gcc gcc aac gtg atc tac cag tac atg gac gac ctg ctg ctg tgg aag      864
Ala Ala Asn Val Ile Tyr Gln Tyr Met Asp Asp Leu Leu Leu Trp Lys
                275                 280                 285 ggc gag ggc gcc gtg aag gcc gcc cgc atc cgc acc tgg aag agc ctg      912
Gly Glu Gly Ala Val Lys Ala Ala Arg Ile Arg Thr Trp Lys Ser Leu
            290                 295                 300 gtg aag cac ccc aag gtg agc agc gag gtg cac atc gcc gtg cgc cac      960
Val Lys His Pro Lys Val Ser Ser Glu Val His Ile Ala Val Arg His
                305                 310                 315 ttc ccc cgc atc tgg gcc gtg cgc cac ttc ccc cgc ccc tgg gcc atc     1008
Phe Pro Arg Ile Trp Ala Val Arg His Phe Pro Arg Pro Trp Ala Ile
                320                 325                 330 atc cgc atc ctg cag cag ctg aag gcc gcc gtg ggc ttc ccc gtg cgc     1056
Ile Arg Ile Leu Gln Gln Leu Lys Ala Ala Val Gly Phe Pro Val Arg
335                 340                 345                 350 ccc cag gtg ccc ctg cgc ccc atg acc tac aag ggc gcc gtg gac ctg     1104
Pro Gln Val Pro Leu Arg Pro Met Thr Tyr Lys Gly Ala Val Asp Leu
```

```
                 355                 360                 365
agc cac ttc ctg aag gag aag ggc ggc ctg ggc ccc ggc gtg cgc tac    1152
Ser His Phe Leu Lys Glu Lys Gly Gly Leu Gly Pro Gly Val Arg Tyr
        370                 375                 380 ccc ctg acc ttc ggc tgg tgc tac aag gcc gcc aag acc ctg ccc ctg    1200
Pro Leu Thr Phe Gly Trp Cys Tyr Lys Ala Ala Lys Thr Leu Pro Leu
            385                 390                 395 tgc gtg acc ctg acc gtg tac tac ggc gtg ccc gtg tgg aag gag gcc    1248
Cys Val Thr Leu Thr Val Tyr Tyr Gly Val Pro Val Trp Lys Glu Ala
        400                 405                 410 acc acc acc ctg cgc gcc atc gag gcc cag cag cac ctg gag cgc tac    1296
Thr Thr Thr Leu Arg Ala Ile Glu Ala Gln Gln His Leu Glu Arg Tyr
415                 420                 425                 430 ctg aag gac ggc ggc ctg tag ctcgag                                 1323
Leu Lys Asp Gly Gly Leu
                435

<210> SEQ ID NO 4
<211> LENGTH: 436
<212> TYPE: PRT
<213> ORGANISM: Artificial Sequence
<220> FEATURE:
<223> OTHER INFORMATION: Construct encoding polyepitope polypeptide.

<400> SEQUENCE: 4

Met Glu Leu Arg Ser Leu Tyr Asn Thr Val Ala Thr Leu Tyr Cys Val
1               5                   10                  15

His Gln Arg Ile Lys Ile Arg Leu Arg Pro Gly Gly Lys Lys Lys Tyr
            20                  25                  30

Trp Ala Ser Arg Glu Leu Glu Arg Phe Lys Ala Ala Ile Ser Pro Arg
        35                  40                  45

Thr Leu Asn Ala Trp Val Lys Val Val Lys Ala Phe Ser Pro Glu Val
    50                  55                  60

Ile Pro Met Phe Ser Ala Leu Ser Glu Gly Ala Thr Pro Gln Asp Leu
65                  70                  75                  80

Asn Thr Met Thr Ser Thr Leu Gln Glu Gln Ile Gly Trp Lys Ala Ala
                85                  90                  95

Asn Pro Pro Ile Pro Val Gly Asp Ile Tyr Lys Arg Trp Ile Ile Leu
            100                 105                 110

Gly Leu Asn Lys Ile Val Arg Met Tyr Ser Pro Thr Ser Ile Phe Arg
        115                 120                 125

Asp Tyr Val Asp Arg Phe Tyr Lys Thr Leu Arg Ala Val Gln Asn Ala
    130                 135                 140

Asn Pro Asp Cys Lys Thr Ile Leu Lys Ala Leu Ala Cys Gln Gly Val
145                 150                 155                 160

Gly Gly Pro Gly His Lys Lys Ala Ala Ile Thr Leu Trp Gln Arg Pro
                165                 170                 175

Leu Val Thr Val Leu Asp Val Gly Asp Ala Tyr Phe Ser Val Trp Lys
            180                 185                 190

Gly Ser Pro Ala Ile Phe Gln Ser Lys Leu Arg Gly Pro Gly Arg Ala
        195                 200                 205

Phe Val Thr Ile Lys Ala Ala Cys Thr Pro Tyr Asp Ile Asn Gln
    210                 215                 220

Met Leu Gly Thr Ser Met Thr Lys Ile Leu Lys Glu Pro Val His Gly
225                 230                 235                 240

Val Lys Ala Ala Gln Ile Tyr Gln Glu Pro Phe Lys Asn Leu Lys Thr
                245                 250                 255
```

-continued

```
Gly Glu Pro Ile Val Gly Ala Glu Thr Phe Tyr Val Asp Gly Ala Ala
            260                 265                 270

Asn Val Ile Tyr Gln Tyr Met Asp Asp Leu Leu Leu Trp Lys Gly Glu
        275                 280                 285

Gly Ala Val Lys Ala Ala Arg Ile Arg Thr Trp Lys Ser Leu Val Lys
    290                 295                 300

His Pro Lys Val Ser Ser Glu Val His Ile Ala Val Arg His Phe Pro
305                 310                 315                 320

Arg Ile Trp Ala Val Arg His Phe Pro Arg Pro Trp Ala Ile Ile Arg
                325                 330                 335

Ile Leu Gln Gln Leu Lys Ala Ala Val Gly Phe Pro Val Arg Pro Gln
            340                 345                 350

Val Pro Leu Arg Pro Met Thr Tyr Lys Gly Ala Val Asp Leu Ser His
        355                 360                 365

Phe Leu Lys Glu Lys Gly Gly Leu Gly Pro Gly Val Arg Tyr Pro Leu
    370                 375                 380

Thr Phe Gly Trp Cys Tyr Lys Ala Ala Lys Thr Leu Pro Leu Cys Val
385                 390                 395                 400

Thr Leu Thr Val Tyr Tyr Gly Val Pro Val Trp Lys Glu Ala Thr Thr
                405                 410                 415

Thr Leu Arg Ala Ile Glu Ala Gln Gln His Leu Glu Arg Tyr Leu Lys
            420                 425                 430

Asp Gly Gly Leu
        435

<210> SEQ ID NO 5
<211> LENGTH: 487
<212> TYPE: PRT
<213> ORGANISM: Artificial Sequence
<220> FEATURE:
<223> OTHER INFORMATION: Polyepitope polypeptide.

<400> SEQUENCE: 5

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Glu Leu Arg Ser
65                  70                  75                  80

Leu Tyr Asn Thr Val Ala Thr Leu Tyr Cys Val His Gln Arg Ile Lys
                85                  90                  95

Ile Arg Leu Arg Pro Gly Gly Lys Lys Lys Tyr Trp Ala Ser Arg Glu
            100                 105                 110

Leu Glu Arg Phe Lys Ala Ala Ile Ser Pro Arg Thr Leu Asn Ala Trp
        115                 120                 125

Val Lys Val Val Lys Ala Phe Ser Pro Glu Val Ile Pro Met Phe Ser
    130                 135                 140

Ala Leu Ser Glu Gly Ala Thr Pro Gln Asp Leu Asn Thr Met Thr Ser
145                 150                 155                 160

Thr Leu Gln Glu Gln Ile Gly Trp Lys Ala Ala Asn Pro Pro Ile Pro
                165                 170                 175
```

```
Val Gly Asp Ile Tyr Lys Arg Trp Ile Ile Leu Gly Leu Asn Lys Ile
            180                 185                 190

Val Arg Met Tyr Ser Pro Thr Ser Ile Phe Arg Asp Tyr Val Asp Arg
        195                 200                 205

Phe Tyr Lys Thr Leu Arg Ala Val Gln Asn Ala Asn Pro Asp Cys Lys
    210                 215                 220

Thr Ile Leu Lys Ala Leu Ala Cys Gln Gly Val Gly Pro Gly His
225                 230                 235                 240

Lys Lys Ala Ala Ile Thr Leu Trp Gln Arg Pro Leu Val Thr Val Leu
                245                 250                 255

Asp Val Gly Asp Ala Tyr Phe Ser Val Trp Lys Gly Ser Pro Ala Ile
            260                 265                 270

Phe Gln Ser Lys Leu Gly Thr Ser Met Thr Lys Ile Leu Lys Glu Pro
        275                 280                 285

Val His Gly Val Lys Ala Ala Gln Ile Tyr Gln Glu Pro Phe Lys Asn
    290                 295                 300

Leu Lys Thr Gly Glu Pro Ile Val Gly Ala Glu Thr Phe Tyr Val Asp
305                 310                 315                 320

Gly Ala Ala Asn Val Ile Tyr Gln Tyr Met Asp Asp Leu Leu Leu Trp
                325                 330                 335

Lys Gly Glu Gly Ala Val Lys Ala Ala Arg Ile Arg Thr Trp Lys Ser
            340                 345                 350

Leu Val Lys His Pro Lys Val Ser Ser Glu Val His Ile Ala Val Arg
        355                 360                 365

His Phe Pro Arg Ile Trp Ala Val Arg His Phe Pro Arg Pro Trp Ala
    370                 375                 380

Ile Ile Arg Ile Leu Gln Gln Leu Lys Ala Ala Val Gly Phe Pro Val
385                 390                 395                 400

Arg Pro Gln Val Pro Leu Arg Pro Met Thr Tyr Lys Gly Ala Val Asp
                405                 410                 415

Leu Ser His Phe Leu Lys Glu Lys Gly Gly Leu Gly Pro Gly Val Arg
            420                 425                 430

Tyr Pro Leu Thr Phe Gly Trp Cys Tyr Lys Ala Ala Lys Thr Leu Pro
        435                 440                 445

Leu Cys Val Thr Leu Thr Val Tyr Tyr Gly Val Pro Val Trp Lys Glu
    450                 455                 460

Ala Thr Thr Thr Leu Arg Ala Ile Glu Ala Gln Gln His Leu Glu Arg
465                 470                 475                 480

Tyr Leu Lys Asp Gly Gly Leu
                485

<210> SEQ ID NO 6
<211> LENGTH: 412
<212> TYPE: PRT
<213> ORGANISM: Artificial Sequence
<220> FEATURE:
<223> OTHER INFORMATION: Polyepitope polypeptide.

<400> SEQUENCE: 6

Met Glu Leu Arg Ser Leu Tyr Asn Thr Val Ala Thr Leu Tyr Cys Val
1               5                   10                  15

His Gln Arg Ile Lys Ile Arg Leu Arg Pro Gly Gly Lys Lys Lys Tyr
            20                  25                  30

Trp Ala Ser Arg Glu Leu Glu Arg Phe Lys Ala Ala Ile Ser Pro Arg
        35                  40                  45
```

```
Thr Leu Asn Ala Trp Val Lys Val Lys Ala Phe Ser Pro Glu Val
 50                  55                  60

Ile Pro Met Phe Ser Ala Leu Ser Glu Gly Ala Thr Pro Gln Asp Leu
 65                  70                  75                  80

Asn Thr Met Thr Ser Thr Leu Gln Glu Gln Ile Gly Trp Lys Ala Ala
                 85                  90                  95

Asn Pro Pro Ile Pro Val Gly Asp Ile Tyr Lys Arg Trp Ile Ile Leu
            100                 105                 110

Gly Leu Asn Lys Ile Val Arg Met Tyr Ser Pro Thr Ser Ile Phe Arg
        115                 120                 125

Asp Tyr Val Asp Arg Phe Tyr Lys Thr Leu Arg Ala Val Gln Asn Ala
130                 135                 140

Asn Pro Asp Cys Lys Thr Ile Leu Lys Ala Leu Ala Cys Gln Gly Val
145                 150                 155                 160

Gly Gly Pro Gly His Lys Lys Ala Ala Ile Thr Leu Trp Gln Arg Pro
                165                 170                 175

Leu Val Thr Val Leu Asp Val Gly Asp Ala Tyr Phe Ser Val Trp Lys
            180                 185                 190

Gly Ser Pro Ala Ile Phe Gln Ser Lys Leu Gly Thr Ser Met Thr Lys
        195                 200                 205

Ile Leu Lys Glu Pro Val His Gly Val Lys Ala Ala Gln Ile Tyr Gln
210                 215                 220

Glu Pro Phe Lys Asn Leu Lys Thr Gly Glu Pro Ile Val Gly Ala Glu
225                 230                 235                 240

Thr Phe Tyr Val Asp Gly Ala Ala Asn Val Ile Tyr Gln Tyr Met Asp
                245                 250                 255

Asp Leu Leu Leu Trp Lys Gly Glu Gly Ala Val Lys Ala Ala Arg Ile
            260                 265                 270

Arg Thr Trp Lys Ser Leu Val Lys His Pro Lys Val Ser Ser Glu Val
        275                 280                 285

His Ile Ala Val Arg His Phe Pro Arg Ile Trp Ala Val Arg His Phe
290                 295                 300

Pro Arg Pro Trp Ala Ile Ile Arg Ile Leu Gln Gln Leu Lys Ala Ala
305                 310                 315                 320

Val Gly Phe Pro Val Arg Pro Gln Val Pro Leu Arg Pro Met Thr Tyr
                325                 330                 335

Lys Gly Ala Val Asp Leu Ser His Phe Leu Lys Glu Lys Gly Gly Leu
            340                 345                 350

Gly Pro Gly Val Arg Tyr Pro Leu Thr Phe Gly Trp Cys Tyr Lys Ala
        355                 360                 365

Ala Lys Thr Leu Pro Leu Cys Val Thr Leu Thr Val Tyr Tyr Gly Val
370                 375                 380

Pro Val Trp Lys Glu Ala Thr Thr Thr Leu Arg Ala Ile Glu Ala Gln
385                 390                 395                 400

Gln His Leu Glu Arg Tyr Leu Lys Asp Gly Gly Leu
                405                 410
```

<210> SEQ ID NO 7
<211> LENGTH: 2126
<212> TYPE: DNA
<213> ORGANISM: Artificial Sequence
<220> FEATURE:
<223> OTHER INFORMATION: Construct encoding polyepitope polypeptide.
<220> FEATURE:
<221> NAME/KEY: CDS
<222> LOCATION: (7)..(2118)
<223> OTHER INFORMATION: Sequence encoding MCMVABTh-LIMPII polyepitope polypeptide.

<400> SEQUENCE: 7

```
gctagc atg gcc tgc acc aac tgc tac tgc aag aag tgc tgc ttc cac        48
       Met Ala Cys Thr Asn Cys Tyr Cys Lys Lys Cys Cys Phe His
       1               5                   10 tgc cag gtg tgc ttc acc acc ggc ccc ggc ccc cgc cag cgc cgc            96
Cys Gln Val Cys Phe Thr Thr Gly Pro Gly Pro Arg Gln Arg Arg
15                  20                  25                  30 gcc ccc cag gac agc cag acc cac cag gtg agc gta tac tac gcc gcc       144
Ala Pro Gln Asp Ser Gln Thr His Gln Val Ser Val Tyr Tyr Ala Ala
                35                  40                  45 gcc cag tgg gac ttc ggc aac acc atg tgc cag atc aat ccc ggc cgc       192
Ala Gln Trp Asp Phe Gly Asn Thr Met Cys Gln Ile Asn Pro Gly Arg
            50                  55                  60 agc cag aag gag ggc ctg cac tac acc tgc gta tac ggc ccc ggc ccc       240
Ser Gln Lys Glu Gly Leu His Tyr Thr Cys Val Tyr Gly Pro Gly Pro
65                  70                  75 ccc tgc aac aag tgc tac tgc aag aag tgc tgc tac cac tgc cag gtg       288
Pro Cys Asn Lys Cys Tyr Cys Lys Lys Cys Cys Tyr His Cys Gln Val
        80                  85                  90 tgc ttc ctg aac aat ccc ggc aag cag cgc cgc ggc acc ccc cag agc       336
Cys Phe Leu Asn Asn Pro Gly Lys Gln Arg Arg Gly Thr Pro Gln Ser
95                  100                 105                 110 aac aag gac cac cag aac ccc ggc cct gga ccc aac gag cag gac ctg       384
Asn Lys Asp His Gln Asn Pro Gly Pro Gly Pro Asn Glu Gln Asp Leu
                115                 120                 125 ctg gcc ctg gac aag tgg gcc aac ctg tgg aac tgg ttc gac atc agc       432
Leu Ala Leu Asp Lys Trp Ala Asn Leu Trp Asn Trp Phe Asp Ile Ser
            130                 135                 140 aat ccc ggc gcc tgc aac acc tgc tac tgc aag aag tgc agc tac cac       480
Asn Pro Gly Ala Cys Asn Thr Cys Tyr Cys Lys Lys Cys Ser Tyr His
            145                 150                 155 tgc ctg gtg tgc ttc cag acc ggc ccc ggc ccc cgc cag cgc cgc agc       528
Cys Leu Val Cys Phe Gln Thr Gly Pro Gly Pro Arg Gln Arg Arg Ser
160                 165                 170 gcc ccc ccc agc agc gag gac cac cag aac ctg aat ccc ggc aac gag       576
Ala Pro Pro Ser Ser Glu Asp His Gln Asn Leu Asn Pro Gly Asn Glu
175                 180                 185                 190 cag gag ctg ctg gag ctg gac aag tgg gcc agc ctg tgg aac tgg ttc       624
Gln Glu Leu Leu Glu Leu Asp Lys Trp Ala Ser Leu Trp Asn Trp Phe
                195                 200                 205 gac atc acc ggc cca gga ccc cac gag cgc agc tac atg ttc agc gac       672
Asp Ile Thr Gly Pro Gly Pro His Glu Arg Ser Tyr Met Phe Ser Asp
            210                 215                 220 ctg gag aac cgc tgc atc aac gag aag gac ctg ctg gcc ctg gac aag       720
Leu Glu Asn Arg Cys Ile Asn Glu Lys Asp Leu Leu Ala Leu Asp Lys
            225                 230                 235 tgg cag aac ctg tgg agc tgg ttc gac atc acc aac cct ggc agc ggc       768
Trp Gln Asn Leu Trp Ser Trp Phe Asp Ile Thr Asn Pro Gly Ser Gly
240                 245                 250 atc gtg cag cag cag aac aac ctg ctg cgc gcc atc gag gcc cag cag       816
Ile Val Gln Gln Gln Asn Asn Leu Leu Arg Ala Ile Glu Ala Gln Gln
255                 260                 265                 270 cac ctg ctg cag ctg acc acc gtg tgg ggc atc aag cag ctg cag gcc       864
His Leu Leu Gln Leu Thr Thr Val Trp Gly Ile Lys Gln Leu Gln Ala
                275                 280                 285 cgc atc ctg aat ccc ggc ggt cct gga cca tgg atg gag tgg gac cgc       912
```

```
Arg Ile Leu Asn Pro Gly Gly Pro Gly Pro Trp Met Glu Trp Asp Arg
            290                 295                 300 gag atc aac aac tac acc agc ctg atc cac agc ctg atc gag gag agc    960
Glu Ile Asn Asn Tyr Thr Ser Leu Ile His Ser Leu Ile Glu Glu Ser
        305                 310                 315 cag aac cag cag gag aag aac gag cag gag ctg ctg tct aga ccc ggg   1008
Gln Asn Gln Gln Glu Lys Asn Glu Gln Glu Leu Leu Ser Arg Pro Gly
320                 325                 330 ggt acc atg gcc ttc agc ccc gag gtg atc ccc atg ttc agc gcc ctg   1056
Gly Thr Met Ala Phe Ser Pro Glu Val Ile Pro Met Phe Ser Ala Leu
335                 340                 345                 350 agc gag ggc gcc acc ccc cag gac ctg ccc atc gtg cag aac atc cag   1104
Ser Glu Gly Ala Thr Pro Gln Asp Leu Pro Ile Val Gln Asn Ile Gln
            355                 360                 365 ggc cag atg gtg cac cag gcc atc agc ccc cgc acc ctg aac gcc ggc   1152
Gly Gln Met Val His Gln Ala Ile Ser Pro Arg Thr Leu Asn Ala Gly
        370                 375                 380 ccc ggc ccc ctg cag gag cag atc ggc tgg atg acc aac aac ccc ccc   1200
Pro Gly Pro Leu Gln Glu Gln Ile Gly Trp Met Thr Asn Asn Pro Pro
    385                 390                 395 atc ccc gtg ggc gag atc tac aag cgc tgg atc atc ctg ggc ctg aac   1248
Ile Pro Val Gly Glu Ile Tyr Lys Arg Trp Ile Ile Leu Gly Leu Asn
400                 405                 410 aag atc gtg cgc atg tac agc ccc acc agc atc ctg gac atc cgc cag   1296
Lys Ile Val Arg Met Tyr Ser Pro Thr Ser Ile Leu Asp Ile Arg Gln
415                 420                 425                 430 ggc ccc aag gag ccc ttc cgc gac tac gtg gac cgc ttc tac aag gag   1344
Gly Pro Lys Glu Pro Phe Arg Asp Tyr Val Asp Arg Phe Tyr Lys Glu
            435                 440                 445 atc tgc acc gag atg gag aag gag ggc aag atc agc aag atc ggc ccc   1392
Ile Cys Thr Glu Met Glu Lys Glu Gly Lys Ile Ser Lys Ile Gly Pro
        450                 455                 460 ggc ccc ggc ccc ttc cgc aag tac acc gcc ttc acc atc ccc agc atc   1440
Gly Pro Gly Pro Phe Arg Lys Tyr Thr Ala Phe Thr Ile Pro Ser Ile
    465                 470                 475 aac aac gag agc ccc gcc atc ttc cag agc agc atg acc aag atc ctg   1488
Asn Asn Glu Ser Pro Ala Ile Phe Gln Ser Ser Met Thr Lys Ile Leu
480                 485                 490 gag ccc tgg gag ttc gtg aac acc ccc ccc ctg gtg aag ctg tgg tac   1536
Glu Pro Trp Glu Phe Val Asn Thr Pro Pro Leu Val Lys Leu Trp Tyr
495                 500                 505                 510 cag aag acc gcc gtg cag atg gcc gtg ttc atc cac aac ttc aag cgc   1584
Gln Lys Thr Ala Val Gln Met Ala Val Phe Ile His Asn Phe Lys Arg
            515                 520                 525 cag aag cag atc acc aag atc cag aac ttc cgc gtg tac tac cgc ggc   1632
Gln Lys Gln Ile Thr Lys Ile Gln Asn Phe Arg Val Tyr Tyr Arg Gly
        530                 535                 540 ccc ggc ccc cag ctg ctg ttc atc cac ttc cgc tcg cgc cag cgg cgg   1680
Pro Gly Pro Gln Leu Leu Phe Ile His Phe Arg Ser Arg Gln Arg Arg
    545                 550                 555 cgg cgg tac agc agc ttg atc agg cgc acg gtg cgg atc agc tcc tcg   1728
Arg Arg Tyr Ser Ser Leu Ile Arg Arg Thr Val Arg Ile Ser Ser Ser
560                 565                 570 tcg cgg ctg tgg cgg cag ccg atg cgg aag tgg atg aac agc agc atc   1776
Ser Arg Leu Trp Arg Gln Pro Met Arg Lys Trp Met Asn Ser Ser Ile
575                 580                 585                 590 agc ggc ccc ggc ccc gac atg cgc gac aac tgg cgc agc gag ctg tac   1824
Ser Gly Pro Gly Pro Asp Met Arg Asp Asn Trp Arg Ser Glu Leu Tyr
            595                 600                 605
```

```
aag tac aag gtg cag cag cac ctg ctg cag ctg acc gtg tgg ggc atc    1872
Lys Tyr Lys Val Gln Gln His Leu Leu Gln Leu Thr Val Trp Gly Ile
            610                 615                 620 aag cag ctg gcc agc ctg tgg aac tgg ttc gac atc acc aac tgg ctg    1920
Lys Gln Leu Ala Ser Leu Trp Asn Trp Phe Asp Ile Thr Asn Trp Leu
        625                 630                 635 tgg tac atc aag atc ttc atc atg atc gtg ggc ggc ctg atc ggc ctg    1968
Trp Tyr Ile Lys Ile Phe Ile Met Ile Val Gly Gly Leu Ile Gly Leu
    640                 645                 650 cgc cac atc ccc cgc cgc atc cgc cag ggc ctg gag cgc gcc ctg agg    2016
Arg His Ile Pro Arg Arg Ile Arg Gln Gly Leu Glu Arg Ala Leu Arg
655                 660                 665                 670 gca gca tgg acg agg gca ccg ccg acg agc gcg ccc ccc cgc ggc cag    2064
Ala Ala Trp Thr Arg Ala Pro Pro Thr Ser Ala Pro Pro Arg Gly Gln
                675                 680                 685 ggc agc atg gac gag ggc acc gcc gac gag cgc gcc ccc ctg atc cgc    2112
Gly Ser Met Asp Glu Gly Thr Ala Asp Glu Arg Ala Pro Leu Ile Arg
        690                 695                 700 acc tga gtttaaac                                                    2126
Thr

<210> SEQ ID NO 8
<211> LENGTH: 703
<212> TYPE: PRT
<213> ORGANISM: Artificial Sequence
<220> FEATURE:
<223> OTHER INFORMATION: Construct encoding polyepitope polypeptide.

<400> SEQUENCE: 8

Met Ala Cys Thr Asn Cys Tyr Cys Lys Lys Cys Cys Phe His Cys Gln
1               5                   10                  15

Val Cys Phe Thr Thr Gly Pro Gly Pro Arg Gln Arg Arg Ala Pro
            20                  25                  30

Gln Asp Ser Gln Thr His Gln Val Ser Val Tyr Tyr Ala Ala Ala Gln
        35                  40                  45

Trp Asp Phe Gly Asn Thr Met Cys Gln Ile Asn Pro Gly Arg Ser Gln
    50                  55                  60

Lys Glu Gly Leu His Tyr Thr Cys Val Tyr Gly Pro Gly Pro Pro Cys
65                  70                  75                  80

Asn Lys Cys Tyr Cys Lys Lys Cys Cys Tyr His Cys Gln Val Cys Phe
                85                  90                  95

Leu Asn Asn Pro Gly Lys Gln Arg Arg Gly Thr Pro Gln Ser Asn Lys
            100                 105                 110

Asp His Gln Asn Pro Gly Pro Gly Pro Asn Glu Gln Asp Leu Leu Ala
        115                 120                 125

Leu Asp Lys Trp Ala Asn Leu Trp Asn Trp Phe Asp Ile Ser Asn Pro
    130                 135                 140

Gly Ala Cys Asn Thr Cys Tyr Cys Lys Lys Cys Ser Tyr His Cys Leu
145                 150                 155                 160

Val Cys Phe Gln Thr Gly Pro Gly Pro Arg Gln Arg Arg Ser Ala Pro
                165                 170                 175

Pro Ser Ser Glu Asp His Gln Asn Leu Asn Pro Gly Asn Glu Gln Glu
            180                 185                 190

Leu Leu Glu Leu Asp Lys Trp Ala Ser Leu Trp Asn Trp Phe Asp Ile
        195                 200                 205

Thr Gly Pro Gly Pro His Glu Arg Ser Tyr Met Phe Ser Asp Leu Glu
    210                 215                 220
```

-continued

```
Asn Arg Cys Ile Asn Glu Lys Asp Leu Leu Ala Leu Asp Lys Trp Gln
225                 230                 235                 240

Asn Leu Trp Ser Trp Phe Asp Ile Thr Asn Pro Gly Ser Gly Ile Val
            245                 250                 255

Gln Gln Gln Asn Asn Leu Leu Arg Ala Ile Glu Ala Gln Gln His Leu
        260                 265                 270

Leu Gln Leu Thr Thr Val Trp Gly Ile Lys Gln Leu Gln Ala Arg Ile
    275                 280                 285

Leu Asn Pro Gly Gly Pro Gly Pro Trp Met Glu Trp Asp Arg Glu Ile
290                 295                 300

Asn Asn Tyr Thr Ser Leu Ile His Ser Leu Ile Glu Glu Ser Gln Asn
305                 310                 315                 320

Gln Gln Glu Lys Asn Glu Gln Glu Leu Leu Ser Arg Pro Gly Gly Thr
            325                 330                 335

Met Ala Phe Ser Pro Glu Val Ile Pro Met Phe Ser Ala Leu Ser Glu
        340                 345                 350

Gly Ala Thr Pro Gln Asp Leu Pro Ile Val Gln Asn Ile Gln Gly Gln
    355                 360                 365

Met Val His Gln Ala Ile Ser Pro Arg Thr Leu Asn Ala Gly Pro Gly
370                 375                 380

Pro Leu Gln Glu Gln Ile Gly Trp Met Thr Asn Asn Pro Pro Ile Pro
385                 390                 395                 400

Val Gly Glu Ile Tyr Lys Arg Trp Ile Ile Leu Gly Leu Asn Lys Ile
            405                 410                 415

Val Arg Met Tyr Ser Pro Thr Ser Ile Leu Asp Ile Arg Gln Gly Pro
        420                 425                 430

Lys Glu Pro Phe Arg Asp Tyr Val Asp Arg Phe Tyr Lys Glu Ile Cys
    435                 440                 445

Thr Glu Met Glu Lys Glu Gly Lys Ile Ser Lys Ile Gly Pro Gly Pro
450                 455                 460

Gly Pro Phe Arg Lys Tyr Thr Ala Phe Thr Ile Pro Ser Ile Asn Asn
465                 470                 475                 480

Glu Ser Pro Ala Ile Phe Gln Ser Ser Met Thr Lys Ile Leu Glu Pro
            485                 490                 495

Trp Glu Phe Val Asn Thr Pro Pro Leu Val Lys Leu Trp Tyr Gln Lys
        500                 505                 510

Thr Ala Val Gln Met Ala Val Phe Ile His Asn Phe Lys Arg Gln Lys
    515                 520                 525

Gln Ile Thr Lys Ile Gln Asn Phe Arg Val Tyr Tyr Arg Gly Pro Gly
530                 535                 540

Pro Gln Leu Leu Phe Ile His Phe Arg Ser Arg Gln Arg Arg Arg Arg
545                 550                 555                 560

Tyr Ser Ser Leu Ile Arg Arg Thr Val Arg Ile Ser Ser Ser Ser Arg
            565                 570                 575

Leu Trp Arg Gln Pro Met Arg Lys Trp Met Asn Ser Ser Ile Ser Gly
        580                 585                 590

Pro Gly Pro Asp Met Arg Asp Asn Trp Arg Ser Glu Leu Tyr Lys Tyr
    595                 600                 605

Lys Val Gln Gln His Leu Leu Gln Leu Thr Val Trp Gly Ile Lys Gln
610                 615                 620

Leu Ala Ser Leu Trp Asn Trp Phe Asp Ile Thr Asn Trp Leu Trp Tyr
625                 630                 635                 640

Ile Lys Ile Phe Ile Met Ile Val Gly Gly Leu Ile Gly Leu Arg His
```

```
                          645                 650                 655
Ile Pro Arg Arg Ile Arg Gln Gly Leu Glu Arg Ala Leu Arg Ala Ala
            660                 665                 670

Trp Thr Arg Ala Pro Pro Thr Ser Ala Pro Pro Arg Gly Gln Gly Ser
        675                 680                 685

Met Asp Glu Gly Thr Ala Asp Glu Arg Ala Pro Leu Ile Arg Thr
    690                 695                 700

<210> SEQ ID NO 9
<211> LENGTH: 2063
<212> TYPE: DNA
<213> ORGANISM: Artificial Sequence
<220> FEATURE:
<223> OTHER INFORMATION: Construct encoding polyepitope polypeptide.
<220> FEATURE:
<221> NAME/KEY: CDS
<222> LOCATION: (7)..(2061)
<223> OTHER INFORMATION: Sequence encoding MCMVABTh polyepitope
      polypeptide.

<400> SEQUENCE: 9 gctagc atg gcc tgc acc aac tgc tac tgc aag aag tgc tgc ttc cac        48
       Met Ala Cys Thr Asn Cys Tyr Cys Lys Lys Cys Cys Phe His
       1               5                   10 tgc cag gtg tgc ttc acc acc ggc ccc ggc ccc cgc cag cgc cgc           96
Cys Gln Val Cys Phe Thr Thr Gly Pro Gly Pro Arg Gln Arg Arg
15                  20                  25                  30 gcc ccc cag gac agc cag acc cac cag gtg agc gta tac tac gcc gcc      144
Ala Pro Gln Asp Ser Gln Thr His Gln Val Ser Val Tyr Tyr Ala Ala
                35                  40                  45 gcc cag tgg gac ttc ggc aac acc atg tgc cag atc aat ccc ggc cgc      192
Ala Gln Trp Asp Phe Gly Asn Thr Met Cys Gln Ile Asn Pro Gly Arg
            50                  55                  60 agc cag aag gag ggc ctg cac tac acc tgc gta tac ggc ccc ggc ccc      240
Ser Gln Lys Glu Gly Leu His Tyr Thr Cys Val Tyr Gly Pro Gly Pro
        65                  70                  75 ccc tgc aac aag tgc tac tgc aag aag tgc tgc tac cac tgc cag gtg     288
Pro Cys Asn Lys Cys Tyr Cys Lys Lys Cys Cys Tyr His Cys Gln Val
    80                  85                  90 tgc ttc ctg aac aat ccc ggc aag cag cgc cgc ggc acc ccc cag agc     336
Cys Phe Leu Asn Asn Pro Gly Lys Gln Arg Arg Gly Thr Pro Gln Ser
95                  100                 105                 110 aac aag gac cac cag aac ccc ggc cct gga ccc aac gag cag gac ctg     384
Asn Lys Asp His Gln Asn Pro Gly Pro Gly Pro Asn Glu Gln Asp Leu
                115                 120                 125 ctg gcc ctg gac aag tgg gcc aac ctg tgg aac tgg ttc gac atc agc     432
Leu Ala Leu Asp Lys Trp Ala Asn Leu Trp Asn Trp Phe Asp Ile Ser
            130                 135                 140 aat ccc ggc gcc tgc aac acc tgc tac tgc aag aag tgc agc tac cac     480
Asn Pro Gly Ala Cys Asn Thr Cys Tyr Cys Lys Lys Cys Ser Tyr His
        145                 150                 155 tgc ctg gtg tgc ttc cag acc ggc ccc ggc ccc cgc cag cgc cgc agc     528
Cys Leu Val Cys Phe Gln Thr Gly Pro Gly Pro Arg Gln Arg Arg Ser
    160                 165                 170 gcc ccc ccc agc agc gag gac cac cag aac ctg aat ccc ggc aac gag     576
Ala Pro Pro Ser Ser Glu Asp His Gln Asn Leu Asn Pro Gly Asn Glu
175                 180                 185                 190 cag gag ctg ctg gag ctg gac aag tgg gcc agc ctg tgg aac tgg ttc     624
Gln Glu Leu Leu Glu Leu Asp Lys Trp Ala Ser Leu Trp Asn Trp Phe
                195                 200                 205
```

```
gac atc acc ggc cca gga ccc cac gag cgc agc tac atg ttc agc gac      672
Asp Ile Thr Gly Pro Gly Pro His Glu Arg Ser Tyr Met Phe Ser Asp
        210                 215                 220 ctg gag aac cgc tgc atc aac gag aag gac ctg ctg gcc ctg gac aag      720
Leu Glu Asn Arg Cys Ile Asn Glu Lys Asp Leu Leu Ala Leu Asp Lys
                225                 230                 235 tgg cag aac ctg tgg agc tgg ttc gac atc acc aac cct ggc agc ggc      768
Trp Gln Asn Leu Trp Ser Trp Phe Asp Ile Thr Asn Pro Gly Ser Gly
    240                 245                 250 atc gtg cag cag cag aac aac ctg ctg cgc gcc atc gag gcc cag cag      816
Ile Val Gln Gln Gln Asn Asn Leu Leu Arg Ala Ile Glu Ala Gln Gln
255                 260                 265                 270 cac ctg ctg cag ctg acc acc gtg tgg ggc atc aag cag ctg cag gcc      864
His Leu Leu Gln Leu Thr Thr Val Trp Gly Ile Lys Gln Leu Gln Ala
                275                 280                 285 cgc atc ctg aat ccc ggc ggt cct gga cca tgg atg gag tgg gac cgc      912
Arg Ile Leu Asn Pro Gly Gly Pro Gly Pro Trp Met Glu Trp Asp Arg
            290                 295                 300 gag atc aac aac tac acc agc ctg atc cac agc ctg atc gag gag agc      960
Glu Ile Asn Asn Tyr Thr Ser Leu Ile His Ser Leu Ile Glu Glu Ser
305                 310                 315 cag aac cag cag gag aag aac gag cag gag ctg ctg tct aga ccc ggg     1008
Gln Asn Gln Gln Glu Lys Asn Glu Gln Glu Leu Leu Ser Arg Pro Gly
    320                 325                 330 ggt acc atg gcc ttc agc ccc gag gtg atc ccc atg ttc agc gcc ctg     1056
Gly Thr Met Ala Phe Ser Pro Glu Val Ile Pro Met Phe Ser Ala Leu
335                 340                 345                 350 agc gag ggc gcc acc ccc cag gac ctg ccc atc gtg cag aac atc cag     1104
Ser Glu Gly Ala Thr Pro Gln Asp Leu Pro Ile Val Gln Asn Ile Gln
                355                 360                 365 ggc cag atg gtg cac cag gcc atc agc ccc cgc acc ctg aac gcc ggc     1152
Gly Gln Met Val His Gln Ala Ile Ser Pro Arg Thr Leu Asn Ala Gly
            370                 375                 380 ccc ggc ccc ctg cag gag cag atc ggc tgg atg acc aac aac ccc ccc     1200
Pro Gly Pro Leu Gln Glu Gln Ile Gly Trp Met Thr Asn Asn Pro Pro
        385                 390                 395 atc ccc gtg ggc gag atc tac aag cgc tgg atc atc ctg ggc ctg aac     1248
Ile Pro Val Gly Glu Ile Tyr Lys Arg Trp Ile Ile Leu Gly Leu Asn
    400                 405                 410 aag atc gtg cgc atg tac agc ccc acc agc atc ctg gac atc cgc cag     1296
Lys Ile Val Arg Met Tyr Ser Pro Thr Ser Ile Leu Asp Ile Arg Gln
415                 420                 425                 430 ggc ccc aag gag ccc ttc cgc gac tac gtg gac cgc ttc tac aag gag     1344
Gly Pro Lys Glu Pro Phe Arg Asp Tyr Val Asp Arg Phe Tyr Lys Glu
                435                 440                 445 atc tgc acc gag atg gag aag gag ggc aag atc agc aag atc ggc ccc     1392
Ile Cys Thr Glu Met Glu Lys Glu Gly Lys Ile Ser Lys Ile Gly Pro
            450                 455                 460 ggc ccc ggc ccc ttc cgc aag tac acc gcc ttc acc atc ccc agc atc     1440
Gly Pro Gly Pro Phe Arg Lys Tyr Thr Ala Phe Thr Ile Pro Ser Ile
        465                 470                 475 aac aac gag agc ccc gcc atc ttc cag agc agc atg acc aag atc ctg     1488
Asn Asn Glu Ser Pro Ala Ile Phe Gln Ser Ser Met Thr Lys Ile Leu
    480                 485                 490 gag ccc tgg gag ttc gtg aac acc ccc ccc ctg gtg aag ctg tgg tac     1536
Glu Pro Trp Glu Phe Val Asn Thr Pro Pro Leu Val Lys Leu Trp Tyr
495                 500                 505                 510 cag aag acc gcc gtg cag atg gcc gtg ttc atc cac aac ttc aag cgc     1584
Gln Lys Thr Ala Val Gln Met Ala Val Phe Ile His Asn Phe Lys Arg
                515                 520                 525
```

```
cag aag cag atc acc aag atc cag aac ttc cgc gtg tac tac cgc ggc    1632
Gln Lys Gln Ile Thr Lys Ile Gln Asn Phe Arg Val Tyr Tyr Arg Gly
            530                 535                 540 ccc ggc ccc cag ctg ctg ttc atc cac ttc cgc tcg cgc cag cgg cgg    1680
Pro Gly Pro Gln Leu Leu Phe Ile His Phe Arg Ser Arg Gln Arg Arg
        545                 550                 555 cgg cgg tac agc agc ttg atc agg cgc acg gtg cgg atc agc tcc tcg    1728
Arg Arg Tyr Ser Ser Leu Ile Arg Arg Thr Val Arg Ile Ser Ser Ser
    560                 565                 570 tcg cgg ctg tgg cgg cag ccg atg cgg aag tgg atg aac agc agc atc    1776
Ser Arg Leu Trp Arg Gln Pro Met Arg Lys Trp Met Asn Ser Ser Ile
575                 580                 585                 590 agc ggc ccc ggc ccc gac atg cgc gac aac tgg cgc agc gag ctg tac    1824
Ser Gly Pro Gly Pro Asp Met Arg Asp Asn Trp Arg Ser Glu Leu Tyr
                595                 600                 605 aag tac aag gtg cag cag cac ctg ctg cag ctg acc gtg tgg ggc atc    1872
Lys Tyr Lys Val Gln Gln His Leu Leu Gln Leu Thr Val Trp Gly Ile
            610                 615                 620 aag cag ctg gcc agc ctg tgg aac tgg ttc gac atc acc aac tgg ctg    1920
Lys Gln Leu Ala Ser Leu Trp Asn Trp Phe Asp Ile Thr Asn Trp Leu
        625                 630                 635 tgg tac atc aag atc ttc atc atg atc gtg ggc ggc ctg atc ggc ctg    1968
Trp Tyr Ile Lys Ile Phe Ile Met Ile Val Gly Gly Leu Ile Gly Leu
    640                 645                 650 cgc cac atc ccc cgc cgc atc cgc cag ggc ctg gag cgc gcc ctg agg    2016
Arg His Ile Pro Arg Arg Ile Arg Gln Gly Leu Glu Arg Ala Leu Arg
655                 660                 665                 670 gca gca tgg acg agg gca ccg ccg acg agc gcg ccc ccc gtt taa ac     2063
Ala Ala Trp Thr Arg Ala Pro Pro Thr Ser Ala Pro Pro Val
                675                 680

<210> SEQ ID NO 10
<211> LENGTH: 684
<212> TYPE: PRT
<213> ORGANISM: Artificial Sequence
<220> FEATURE:
<223> OTHER INFORMATION: Construct encoding polyepitope polypeptide.

<400> SEQUENCE: 10

Met Ala Cys Thr Asn Cys Tyr Cys Lys Lys Cys Cys Phe His Cys Gln
1               5                   10                  15

Val Cys Phe Thr Thr Gly Pro Gly Pro Arg Gln Arg Arg Arg Ala Pro
            20                  25                  30

Gln Asp Ser Gln Thr His Gln Val Ser Val Tyr Tyr Ala Ala Ala Gln
        35                  40                  45

Trp Asp Phe Gly Asn Thr Met Cys Gln Ile Asn Pro Gly Arg Ser Gln
    50                  55                  60

Lys Glu Gly Leu His Tyr Thr Cys Val Tyr Gly Pro Gly Pro Cys
65                  70                  75                  80

Asn Lys Cys Tyr Cys Lys Lys Cys Cys Tyr His Cys Gln Val Cys Phe
                85                  90                  95

Leu Asn Asn Pro Gly Lys Gln Arg Arg Gly Thr Pro Gln Ser Asn Lys
            100                 105                 110

Asp His Gln Asn Pro Gly Pro Gly Pro Asn Glu Gln Asp Leu Leu Ala
        115                 120                 125

Leu Asp Lys Trp Ala Asn Leu Trp Asn Trp Phe Asp Ile Ser Asn Pro
    130                 135                 140

Gly Ala Cys Asn Thr Cys Tyr Cys Lys Lys Cys Ser Tyr His Cys Leu
```

```
                145                 150                 155                 160
Val Cys Phe Gln Thr Gly Pro Gly Pro Arg Gln Arg Ser Ala Pro
                    165                 170                 175
Pro Ser Ser Glu Asp His Gln Asn Leu Asn Pro Gly Asn Gln Glu
                    180                 185                 190
Leu Leu Glu Leu Asp Lys Trp Ala Ser Leu Trp Asn Trp Phe Asp Ile
                    195                 200                 205
Thr Gly Pro Gly Pro His Glu Arg Ser Tyr Met Phe Ser Asp Leu Glu
                    210                 215                 220
Asn Arg Cys Ile Asn Glu Lys Asp Leu Leu Ala Leu Asp Lys Trp Gln
225                 230                 235                 240
Asn Leu Trp Ser Trp Phe Asp Ile Thr Asn Pro Gly Ser Gly Ile Val
                    245                 250                 255
Gln Gln Gln Asn Asn Leu Leu Arg Ala Ile Glu Ala Gln Gln His Leu
                    260                 265                 270
Leu Gln Leu Thr Thr Val Trp Gly Ile Lys Gln Leu Gln Ala Arg Ile
                    275                 280                 285
Leu Asn Pro Gly Pro Gly Pro Trp Met Glu Trp Asp Arg Glu Ile
290                 295                 300
Asn Asn Tyr Thr Ser Leu Ile His Ser Leu Ile Glu Glu Ser Gln Asn
305                 310                 315                 320
Gln Gln Glu Lys Asn Glu Gln Glu Leu Leu Ser Arg Pro Gly Gly Thr
                    325                 330                 335
Met Ala Phe Ser Pro Glu Val Ile Pro Met Phe Ser Ala Leu Ser Glu
                    340                 345                 350
Gly Ala Thr Pro Gln Asp Leu Pro Ile Val Gln Asn Ile Gln Gly Gln
                    355                 360                 365
Met Val His Gln Ala Ile Ser Pro Arg Thr Leu Asn Ala Gly Pro Gly
                    370                 375                 380
Pro Leu Gln Glu Gln Ile Gly Trp Met Thr Asn Asn Pro Pro Ile Pro
385                 390                 395                 400
Val Gly Glu Ile Tyr Lys Arg Trp Ile Ile Leu Gly Leu Asn Lys Ile
                    405                 410                 415
Val Arg Met Tyr Ser Pro Thr Ser Ile Leu Asp Ile Arg Gln Gly Pro
                    420                 425                 430
Lys Glu Pro Phe Arg Asp Tyr Val Asp Arg Phe Tyr Lys Glu Ile Cys
                    435                 440                 445
Thr Glu Met Glu Lys Glu Gly Lys Ile Ser Lys Ile Gly Pro Gly Pro
                    450                 455                 460
Gly Pro Phe Arg Lys Tyr Thr Ala Phe Thr Ile Pro Ser Ile Asn Asn
465                 470                 475                 480
Glu Ser Pro Ala Ile Phe Gln Ser Ser Met Thr Lys Ile Leu Glu Pro
                    485                 490                 495
Trp Glu Phe Val Asn Thr Pro Pro Leu Val Lys Leu Trp Tyr Gln Lys
                    500                 505                 510
Thr Ala Val Gln Met Ala Val Phe Ile His Asn Phe Lys Arg Gln Lys
                    515                 520                 525
Gln Ile Thr Lys Ile Gln Asn Phe Arg Val Tyr Tyr Arg Gly Pro Gly
                    530                 535                 540
Pro Gln Leu Leu Phe Ile His Phe Arg Ser Arg Gln Arg Arg Arg
545                 550                 555                 560
Tyr Ser Ser Leu Ile Arg Arg Thr Val Arg Ile Ser Ser Ser Ser Arg
                    565                 570                 575
```

```
Leu Trp Arg Gln Pro Met Arg Lys Trp Met Asn Ser Ser Ile Ser Gly
        580                 585                 590

Pro Gly Pro Asp Met Arg Asp Asn Trp Arg Ser Glu Leu Tyr Lys Tyr
        595                 600                 605

Lys Val Gln Gln His Leu Leu Gln Leu Thr Val Trp Gly Ile Lys Gln
        610                 615                 620

Leu Ala Ser Leu Trp Asn Trp Phe Asp Ile Thr Asn Trp Leu Trp Tyr
625                 630                 635                 640

Ile Lys Ile Phe Ile Met Ile Val Gly Gly Leu Ile Gly Leu Arg His
                645                 650                 655

Ile Pro Arg Arg Ile Arg Gln Gly Leu Glu Arg Ala Leu Arg Ala Ala
                660                 665                 670

Trp Thr Arg Ala Pro Pro Thr Ser Ala Pro Pro Val
                675                 680

<210> SEQ ID NO 11
<211> LENGTH: 14
<212> TYPE: PRT
<213> ORGANISM: Artificial Sequence
<220> FEATURE:
<223> OTHER INFORMATION: HIV-1 antigenic fragment/epitope.

<400> SEQUENCE: 11

Trp Lys Gly Ser Pro Ala Ile Phe Gln Ser Ser Met Thr Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: HIV-1 antigenic fragment/epitope.

<400> SEQUENCE: 12

Ala Val Arg His Phe Pro Arg Ile Trp Leu His Ser Leu
1               5                   10

<210> SEQ ID NO 13
<211> LENGTH: 13
<212> TYPE: PRT
<213> ORGANISM: Artificial Sequence
<220> FEATURE:
<223> OTHER INFORMATION: HIV-1 antigenic fragment/epitope.

<400> SEQUENCE: 13

Ala Val Arg His Phe Pro Arg Pro Trp Leu His Gly Leu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: HIV-1 antigenic fragment/epitope.

<400> SEQUENCE: 14

Glu Arg Tyr Leu Lys Asp Gln Gln Leu
1               5

<210> SEQ ID NO 15
<211> LENGTH: 16
<212> TYPE: PRT
<213> ORGANISM: Artificial Sequence
```

```
<220> FEATURE:
<223> OTHER INFORMATION: HIV-1 antigenic fragment/epitope.

<400> SEQUENCE: 15

Ile Pro Met Phe Ser Ala Leu Ser Glu Gly Ala Thr Pro Asp Gln Leu
1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: HIV-1 antigenic fragment/epitope.

<400> SEQUENCE: 16

Asn Pro Pro Ile Pro Val Gly Glu Ile Tyr Lys Arg Trp Ile Ile
1               5                  10                  15

<210> SEQ ID NO 17
<211> LENGTH: 13
<212> TYPE: PRT
<213> ORGANISM: Artificial Sequence
<220> FEATURE:
<223> OTHER INFORMATION: HIV-1 antigenic fragment/epitope.

<400> SEQUENCE: 17

Trp Lys Gly Ser Pro Ala Ile Phe Gln Ser Ser Met Thr
1               5                  10

<210> SEQ ID NO 18
<211> LENGTH: 9
<212> TYPE: PRT
<213> ORGANISM: Artificial Sequence
<220> FEATURE:
<223> OTHER INFORMATION: HIV-1 antigenic fragment/epitope.

<400> SEQUENCE: 18

Ala Ile Phe Gln Ser Ser Met Thr Lys
1               5

<210> SEQ ID NO 19
<211> LENGTH: 15
<212> TYPE: PRT
<213> ORGANISM: Artificial Sequence
<220> FEATURE:
<223> OTHER INFORMATION: HIV-1 antigenic fragment/epitope.

<400> SEQUENCE: 19

Val Gly Phe Pro Val Thr Pro Gln Val Pro Leu Arg Pro Met Thr
1               5                  10                  15

<210> SEQ ID NO 20
<211> LENGTH: 11
<212> TYPE: PRT
<213> ORGANISM: Artificial Sequence
<220> FEATURE:
<223> OTHER INFORMATION: HIV-1 antigenic fragment/epitope.

<400> SEQUENCE: 20

Arg Ile Arg Thr Thr Trp Lys Ser Leu Val Lys
1               5                  10

<210> SEQ ID NO 21
<211> LENGTH: 13
<212> TYPE: PRT
<213> ORGANISM: Artificial Sequence
<220> FEATURE:
```

```
<223> OTHER INFORMATION: HIV-1 antigenic fragment/epitope.

<400> SEQUENCE: 21

Ala Val Arg His Phe Pro Arg Ile Trp Leu His Ser Leu
1               5                   10

<210> SEQ ID NO 22
<211> LENGTH: 13
<212> TYPE: PRT
<213> ORGANISM: Artificial Sequence
<220> FEATURE:
<223> OTHER INFORMATION: HIV-1 antigenic fragment/epitope.

<400> SEQUENCE: 22

Ala Val Arg His Phe Pro Arg Pro Trp Leu His Gly Leu
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Control peptide.

<400> SEQUENCE: 23

Val Ser Asp Gly Gly Pro Asn Leu Tyr
1               5

<210> SEQ ID NO 24
<211> LENGTH: 9
<212> TYPE: PRT
<213> ORGANISM: Artificial Sequence
<220> FEATURE:
<223> OTHER INFORMATION: Control peptide.

<400> SEQUENCE: 24

Cys Thr Glu Leu Lys Leu Ser Asp Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: Control peptide.

<400> SEQUENCE: 25

Gly Leu Cys Thr Leu Val Ala Met Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Control peptide.

<400> SEQUENCE: 26

Gly Ile Leu Gly Phe Val Phe Thr Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Control peptide.
```

```
<400> SEQUENCE: 27

Asn Leu Val Pro Met Val Ala Thr Val
1               5

<210> SEQ ID NO 28
<211> LENGTH: 9
<212> TYPE: PRT
<213> ORGANISM: Artificial Sequence
<220> FEATURE:
<223> OTHER INFORMATION: Control peptide.

<400> SEQUENCE: 28

Ile Leu Arg Gly Ser Val Ala His Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Control peptide.

<400> SEQUENCE: 29

Arg Val Arg Ala Tyr Thr Tyr Ser Lys
1               5

<210> SEQ ID NO 30
<211> LENGTH: 9
<212> TYPE: PRT
<213> ORGANISM: Artificial Sequence
<220> FEATURE:
<223> OTHER INFORMATION: Control peptide.

<400> SEQUENCE: 30

Arg Leu Arg Ala Glu Ala Gln Val Lys
1               5

<210> SEQ ID NO 31
<211> LENGTH: 9
<212> TYPE: PRT
<213> ORGANISM: Artificial Sequence
<220> FEATURE:
<223> OTHER INFORMATION: Control peptide.

<400> SEQUENCE: 31

Ile Val Thr Asp Phe Ser Val Ile Lys
1               5

<210> SEQ ID NO 32
<211> LENGTH: 9
<212> TYPE: PRT
<213> ORGANISM: Artificial Sequence
<220> FEATURE:
<223> OTHER INFORMATION: Control peptide.

<400> SEQUENCE: 32

Ala Thr Ile Gly Thr Ala Met Tyr Lys
1               5

<210> SEQ ID NO 33
<211> LENGTH: 10
<212> TYPE: PRT
<213> ORGANISM: Artificial Sequence
<220> FEATURE:
<223> OTHER INFORMATION: Control peptide.
```

```
<400> SEQUENCE: 33

Asp Tyr Cys Asn Val Leu Asn Lys Glu Phe
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Control peptide.

<400> SEQUENCE: 34

Lys Thr Gly Gly Pro Ile Tyr Lys Arg
1               5

<210> SEQ ID NO 35
<211> LENGTH: 9
<212> TYPE: PRT
<213> ORGANISM: Artificial Sequence
<220> FEATURE:
<223> OTHER INFORMATION: Control peptide.

<400> SEQUENCE: 35

Arg Pro Pro Ile Phe Ile Arg Arg Leu
1               5

<210> SEQ ID NO 36
<211> LENGTH: 10
<212> TYPE: PRT
<213> ORGANISM: Artificial Sequence
<220> FEATURE:
<223> OTHER INFORMATION: Control peptide.

<400> SEQUENCE: 36

Thr Pro Arg Val Thr Gly Gly Gly Ala Met
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Control peptide.

<400> SEQUENCE: 37

Gln Ala Lys Trp Arg Leu Gln Thr Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Control peptide.

<400> SEQUENCE: 38

Phe Leu Arg Gly Arg Ala Tyr Gly Leu
1               5

<210> SEQ ID NO 39
<211> LENGTH: 8
<212> TYPE: PRT
<213> ORGANISM: Artificial Sequence
<220> FEATURE:
<223> OTHER INFORMATION: Control peptide.

<400> SEQUENCE: 39
```

Arg Ala Lys Phe Lys Gln Leu Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Control peptide.

<400> SEQUENCE: 40

Glu Leu Arg Ser Arg Tyr Trp Ala Ile
1               5

<210> SEQ ID NO 41
<211> LENGTH: 9
<212> TYPE: PRT
<213> ORGANISM: Artificial Sequence
<220> FEATURE:
<223> OTHER INFORMATION: Control peptide.

<400> SEQUENCE: 41

Ser Arg Tyr Trp Ala Ile Arg Thr Arg
1               5

<210> SEQ ID NO 42
<211> LENGTH: 9
<212> TYPE: PRT
<213> ORGANISM: Artificial Sequence
<220> FEATURE:
<223> OTHER INFORMATION: Control peptide.

<400> SEQUENCE: 42

Arg Arg Ile Tyr Asp Leu Ile Glu Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Control peptide.

<400> SEQUENCE: 43

Tyr Pro Leu His Glu Gln His Gly Met
1               5

<210> SEQ ID NO 44
<211> LENGTH: 10
<212> TYPE: PRT
<213> ORGANISM: Artificial Sequence
<220> FEATURE:
<223> OTHER INFORMATION: Control peptide.

<400> SEQUENCE: 44

Glu Glu Asn Leu Leu Asp Phe Val Arg Phe
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Control peptide.

<400> SEQUENCE: 45

```
Gln Glu Phe Phe Trp Asp Ala Asn Asp Ile Tyr Arg Ile Phe Ala
1               5                   10                  15

<210> SEQ ID NO 46
<211> LENGTH: 20
<212> TYPE: PRT
<213> ORGANISM: Artificial Sequence
<220> FEATURE:
<223> OTHER INFORMATION: HIV-1 antigenic fragment/epitope.

<400> SEQUENCE: 46

Pro Cys Asn Lys Cys Tyr Cys Lys Lys Cys Cys Tyr His Cys Gln Val
1               5                   10                  15

Cys Phe Ile Thr
            20

<210> SEQ ID NO 47
<211> LENGTH: 20
<212> TYPE: PRT
<213> ORGANISM: Artificial Sequence
<220> FEATURE:
<223> OTHER INFORMATION: HIV-1 antigenic fragment/epitope.

<400> SEQUENCE: 47

Ala Cys Ser Lys Cys Tyr Cys Lys Lys Cys Cys Trp His Cys Gln Leu
1               5                   10                  15

Cys Phe Leu Lys
            20

<210> SEQ ID NO 48
<211> LENGTH: 20
<212> TYPE: PRT
<213> ORGANISM: Artificial Sequence
<220> FEATURE:
<223> OTHER INFORMATION: HIV-1 antigenic fragment/epitope.

<400> SEQUENCE: 48

Pro Cys Thr Lys Cys Tyr Cys Lys Arg Cys Cys Phe His Cys Gln Trp
1               5                   10                  15

Cys Phe Ile Thr
            20

<210> SEQ ID NO 49
<211> LENGTH: 20
<212> TYPE: PRT
<213> ORGANISM: Artificial Sequence
<220> FEATURE:
<223> OTHER INFORMATION: HIV-1 antigenic fragment/epitope.

<400> SEQUENCE: 49

Ala Cys Ser Lys Cys Tyr Cys His Ile Cys Cys Trp His Cys Gln Leu
1               5                   10                  15

Cys Phe Leu Asn
            20

<210> SEQ ID NO 50
<211> LENGTH: 16
<212> TYPE: PRT
<213> ORGANISM: Artificial Sequence
<220> FEATURE:
<223> OTHER INFORMATION: HIV-1 antigenic fragment/epitope.

<400> SEQUENCE: 50

Arg Gln Arg Arg Arg Pro Pro Gln Gly Gly Gln Ala His Gln Asp Pro
1               5                   10                  15
```

```
<210> SEQ ID NO 51
<211> LENGTH: 16
<212> TYPE: PRT
<213> ORGANISM: Artificial Sequence
<220> FEATURE:
<223> OTHER INFORMATION: HIV-1 antigenic fragment/epitope.

<400> SEQUENCE: 51

Lys His Arg Arg Gly Thr Pro Gln Ser Ser Lys Asp His Gln Asn Pro
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: HIV-1 antigenic fragment/epitope.

<400> SEQUENCE: 52

Arg Arg Arg Arg Gly Thr Pro Gln Ser Arg Gln Asp His Gln Asn Pro
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: HIV-1 antigenic fragment/epitope.

<400> SEQUENCE: 53

Arg Gln Arg His Arg Thr Pro Gln Ser Ser Gln Ile His Gln Asp Pro
1               5                   10                  15

<210> SEQ ID NO 54
<211> LENGTH: 21
<212> TYPE: PRT
<213> ORGANISM: Artificial Sequence
<220> FEATURE:
<223> OTHER INFORMATION: HIV-1 antigenic fragment/epitope.

<400> SEQUENCE: 54

Asn Glu Lys Glu Leu Leu Glu Leu Asp Lys Trp Ala Ser Leu Trp Asn
1               5                   10                  15

Trp Phe Ser Ile Thr
            20

<210> SEQ ID NO 55
<211> LENGTH: 21
<212> TYPE: PRT
<213> ORGANISM: Artificial Sequence
<220> FEATURE:
<223> OTHER INFORMATION: HIV-1 antigenic fragment/epitope.

<400> SEQUENCE: 55

Asn Glu Gln Glu Leu Leu Ala Leu Asp Lys Trp Ala Ser Leu Trp Asn
1               5                   10                  15

Trp Phe Asp Ile Ser
            20

<210> SEQ ID NO 56
<211> LENGTH: 21
<212> TYPE: PRT
<213> ORGANISM: Artificial Sequence
<220> FEATURE:
<223> OTHER INFORMATION: HIV-1 antigenic fragment/epitope.
```

-continued

<400> SEQUENCE: 56

Asn Glu Gln Asp Leu Leu Ala Leu Asp Lys Trp Ala Ser Leu Trp Thr
1               5                   10                  15

Trp Phe Ser Ile Thr
            20

<210> SEQ ID NO 57
<211> LENGTH: 36
<212> TYPE: PRT
<213> ORGANISM: Artificial Sequence
<220> FEATURE:
<223> OTHER INFORMATION: HIV-1 antigenic fragment/epitope.

<400> SEQUENCE: 57

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
        35

<210> SEQ ID NO 58
<211> LENGTH: 15
<212> TYPE: PRT
<213> ORGANISM: Artificial Sequence
<220> FEATURE:
<223> OTHER INFORMATION: HIV-1 antigenic fragment/epitope.

<400> SEQUENCE: 58

Tyr Ala Ala Ala Gln Trp Asp Phe Gly Asn Thr Met Cys Gln Leu
1               5                   10                  15

<210> SEQ ID NO 59
<211> LENGTH: 20
<212> TYPE: PRT
<213> ORGANISM: Artificial Sequence
<220> FEATURE:
<223> OTHER INFORMATION: HIV-1 antigenic fragment/epitope.

<400> SEQUENCE: 59

Cys Ser Ser His Phe Pro Tyr Ser Gln Tyr Gln Phe Trp Lys Asn Phe
1               5                   10                  15

Gln Thr Leu Lys
            20

<210> SEQ ID NO 60
<211> LENGTH: 15
<212> TYPE: PRT
<213> ORGANISM: Artificial Sequence
<220> FEATURE:
<223> OTHER INFORMATION: HIV-1 antigenic fragment/epitope.

<400> SEQUENCE: 60

Ser Pro Val Ser Ile Leu Asp Ile Arg Gln Gly Pro Lys Glu Pro
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: HIV-1 antigenic fragment/epitope.

<400> SEQUENCE: 61

-continued

```
Gln Leu Leu Phe Ile His Phe Arg Ile Gly Cys Arg His Ser Arg
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: HIV-1 antigenic fragment/epitope.

<400> SEQUENCE: 62

Asp Glu Glu Leu Ile Arg Thr Val Arg Leu Ile Lys Leu Leu Tyr
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: HIV-1 antigenic fragment/epitope.

<400> SEQUENCE: 63

Arg Arg Arg Arg Trp Arg Glu Arg Gln Arg Gln Ile His Ser Ile Ser
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: HIV-1 antigenic fragment/epitope.

<400> SEQUENCE: 64

His Ile Pro Arg Arg Ile Arg Gln Gly Leu Glu Arg Ala Leu Leu
1               5                   10                  15
```